US012636274B2

(12) United States Patent
Marathi

(10) Patent No.: US 12,636,274 B2
(45) Date of Patent: May 26, 2026

(54) PHARMACEUTICAL COMPOSITIONS AND METHODS FOR SYSTEMIC TREATMENT OF SOLID TUMORS

(71) Applicant: 7 HILLS INTERESTS LLC, Houston, TX (US)

(72) Inventor: Upendra K. Marathi, Houston, TX (US)

(73) Assignee: 7 Hills Pharma Inc., Houston, TX (US)

( * ) Notice: Subject to any disclaimer, the term of this patent is extended or adjusted under 35 U.S.C. 154(b) by 618 days.

(21) Appl. No.: 16/516,978

(22) Filed: Jul. 19, 2019

(65) Prior Publication Data

US 2020/0054600 A1 Feb. 20, 2020

Related U.S. Application Data

(63) Continuation-in-part of application No. 14/754,931, filed on Jun. 30, 2015, now Pat. No. 11,484,524.

(60) Provisional application No. 62/701,300, filed on Jul. 20, 2018, provisional application No. 62/019,793, filed on Jul. 1, 2014.

(51) Int. Cl.

| | |
|---|---|
| ***A61K 31/381*** | (2006.01) |
| ***A61K 9/00*** | (2006.01) |
| ***A61K 45/06*** | (2006.01) |
| ***A61P 35/00*** | (2006.01) |

(52) U.S. Cl.

CPC .......... *A61K 31/381* (2013.01); *A61K 9/0053* (2013.01); *A61K 45/06* (2013.01); *A61P 35/00* (2018.01)

(58) Field of Classification Search

None

See application file for complete search history.

(56) References Cited

FOREIGN PATENT DOCUMENTS

WO WO-2012068251 A2 * 5/2012 ................ A61P 9/00

OTHER PUBLICATIONS

Khan et al.(FIM, 1:45, 1-11, 2014.*
Tame (J. Comput. Aided Mol. Des. Mar. 1999; 13 (2): 99-108).*
Lensink et al. (Proteins. 2007; 69: 704-718).*
Dixon (Proteins. 1997; Suppl 1: 198-204).*
Driessens et al.(JI, 32(2), 140-144, 2009).*
Oostendorp et al.(LL, 24:423-435, 1997),.*
Aravindaram et al.(GT, 21:457-467, 2014).*
BioLegend Recombinant Mouse GM-CSF, (accessed on Mar. 9, 2022, https://www.biolegend.com/en-us/products/recombinant-mouse-gm-csf-carrier-free-4852?GroupID=GROUP577, pp. 1-6).*

* cited by examiner

*Primary Examiner* — Brad Duffy
(74) *Attorney, Agent, or Firm* — Robert W. Strozier

(57) ABSTRACT

Pharmaceutical compositions including one or more integrin activators capable of capable of improving the anti-cancer activity of nature t-cells, wherein the integrin activators target integrins including, but not limited to, α4β1, α4β7, α5β1, αLβ2 and/or αVβ3 improving binding to their respective ligands including, but not limited to, VCAM-1, fibronectin, MAdCAM-1, ICAM-1, ICAM-2, and/or vitronectin, wherein the compositions treat, ameliorate, and/or reduce symptoms of diseases, maladies, and cancers, and methods for making and using for preventing, treating, ameliorating, and/or reducing symptoms of cancerous tumors, cancerous solid tumors, other cancerous growth, and/or other cancerous.

20 Claims, 9 Drawing Sheets

Study 3 – CD8+/CD4+ Cells Ratios Normalized Total Viable Cells in Tumor

Legend:
- Vehicle Control
- Compound 1 (1mpk (QD))
- Compound 1 (1 mpk (BID))
- PD-1 (J43_50µg/mouse)
- Compound 1 (1 mpk (QD)+ PD-1 ab)
- Compound 1 (1 mpk (BID)+ PD-1 ab)

p<0.05 Vs VC

Ratios Normalized Total Viable Cells in Tumor (1x10^6)

Administered Composition

PHARMACEUTICAL COMPOSITIONS AND METHODS FOR SYSTEMIC TREATMENT OF SOLID TUMORS

RELATED APPLICATIONS

This application claims priority to and the benefit of United State Patent Provisional Patent Application Serial No.: 62/701,300 filed 20 Jul. 2018 (Jul. 20, 2018) and is a continuation-in-part of U.S. patent application Ser. No. 14/754,931 file Jun. 30, 2015, which claims provisional priority to and the benefit of United State Patent Provisional Patent Application Serial No.: 62/019,793 filed 1 Jul. 2014 (Jul. 1, 2014).

This application is related to United States Patent Application Ser. Nos.: (a) Ser. No. 14/621,112 filed Feb. 12, 2015; (b) Ser. No. 15/140,711 filed Apr. 28, 2016, now U.S. Pat. No. 10,342,866 issued 9 Jul. 2019 (Jul. 9, 2019); (c) Ser. No. 16/394,277 filed 25 Apr. 2019 (Apr. 25, 2019), now U.S. Pat. No. 10,716,849 issued 20 Jul. 2020 (Jul. 20, 2020); (d) Ser. No. 16/394,270 filed 25 Apr. 2019 (Apr. 25, 2019), now U.S. Pat. No. 10,709,780 issued 13 Jul. 2019 (Jul. 13, 2020); and (e) Ser. No. 16/516,907 filed 19 Jul. 2019 (Jul. 19, 2019), now U.S. Pat. No. 10,342,866 issued 13 Jul. 2020 (Jul. 13, 2020).

This application is also related to United States Patent Application Ser. Nos.: (b) Ser. No. 13/885,537 filed May 15, 2013 now U.S. Pat. No. 9,512,109 issued 6 Dec. 2016 (Dec. 6, 2016); (c) Ser. No. 14/751,431 filed 26 Jun. 2015 (Jun. 26, 2015), now U.S. Pat. No. 10,071,980 issued 11 Sep. 2018 (Sep. 11, 2018); (d) Ser. No. 14/751,452 filed Jun. 26, 2015, now U.S. Pat. No. 10,035,784 issued 31 Jul. 2018 (Jul. 31, 2018); (e) Ser. No. 15/334,890 filed Oct. 26, 2016, now U.S. Pat. No. 10,287,264 issued 15 May 2019 (May 14, 2019); and (f) Ser. No. 16/354,011 filed 14 Mar. 2019 (Mar. 14, 2019).

BACKGROUND OF THE DISCLOSURE

1. Field of the Disclosure

Embodiments of the present disclosure relate to pharmaceutical compositions and methods for making and using same, wherein the pharmaceutical compositions treat, ameliorate, and/or reduce symptoms of diseases, maladies, cancers, or the like.

In particular, embodiments of the present disclosure relate to pharmaceutical compositions, wherein the compositions include one or more N,N-disubstituted amide compounds, N,N-disubstituted carbamate compounds, N,N-disubstituted urea compounds, and/or N,N-disubstituted sulfonamide compounds, in the presence or absence of one or more anti-cancer agents and methods for using the compounds to treat, ameliorate, and/or reduce symptoms of diseases, maladies, cancers, or the like and methods for making same.

2. Description of the Related Art

While there are many compositions to treat, ameliorate, or reduce symptoms of diseases, maladies, cancers, or the like, there is still a need in the art for new compositions and methods for treating, ameliorating, or reducing symptoms of diseases, maladies, cancers, or the like.

SUMMARY OF THE DISCLOSURE

Embodiments of this disclosure provide pharmaceutical compositions including an effective amount of one or more (one or a plurality of) integrin activators capable of improving the anti-cancer activity of nature t-cells, wherein the integrin activators target integrins including, but not limited to, α4β1, α4β7, α5β1, αLβ2 and/or αVβ3 improving binding to their respective ligands including, but not limited to, VCAM-1, fibronectin, MAdCAM-1, ICAM-1, ICAM-2, and/or vitronectin, wherein the compositions treat, ameliorate, and/or reduce symptoms of diseases, maladies, cancers, or the like. In certain embodiments, the compositions may also include one or more anti-cancer agents, wherein the compositions treat, ameliorate, and/or reduce symptoms of diseases, maladies, cancers, or the like. In other embodiments, the compositions may be formulated for enteral administration in a pharmaceutically acceptable enteral carrier or may be formulated for parenteral administration in a pharmaceutically acceptable parenteral carrier. In other embodiments, the compounds may be used in combination with one or more anti-cancer agents.

Embodiments of this disclosure also provide pharmaceutical compositions including an effective amount of one or more (one or a plurality of) integrin activator compounds comprising N,N-disubstituted amide compounds, N,N-disubstituted carbamate compounds, N,N-disubstituted urea compounds, and/or N,N-disubstituted sulfonamide compounds, in the absence or presence of one or more anti-cancer agents, wherein the compounds treat, ameliorate, and/or reduce symptoms of diseases, maladies, cancers, or the like. In certain embodiments, the compositions may be formulated for enteral administration in a pharmaceutically acceptable enteral carrier or may be formulated for parenteral administration in a pharmaceutically acceptable parenteral carrier. In other embodiments, the compounds may be used in combination with one or more anti-cancer agents.

In certain embodiments, the chemical compounds are compounds of the general Formula (I):

$$R^1\text{-}M\text{-}N(R^2)\text{-}M^2\text{-}M^3\text{-}M^4\text{-}M^5\text{-}M^6\text{-}R^3 \qquad (I)$$

wherein:

- $R^1$ is alkyl, aryl, aralkyl, cycloalkyl, cycloalkylalkyl, haloalkyl, heterocylcyl, or heterocyclylalkyl,
- $R^2$ is alkyl, aryl, aralkyl, cycloalkyl, cycloalkylalkyl, haloalkyl, heterocylcyl, or heterocyclylalkyl,
- $M^1$ is $CH_2$, CO, $SO_2$, or $(CR^4R^5)_l$,
- $M^2$ is absent, $CH_2$, CO, $SO_2$, or $(CR^4R^5)_l$,
- $M^3$ is absent, $CH_2$, O, S, $NR^6$, or $(CR^7R^8)_m$,
- $M^4$ is absent, $CH_2$, or $(CR^9R^{10})_n$,
- $M^5$ is absent, O,$(CR^{11}R^{12})$, or $(CR^{11}R^{12})_p$,
- $M^6$ is $(CH_2)_q$, $(CH_2)_q$—CH═CH—$(CH_2)_r$, $(CH_2)_q$-arylene-$(CH_2)_r$, $(CH_2CH_2O)_q$, or $NR^{34}(CH_2)_q$,
- $R^3$ is hydrogen, alkyl, aryl, aralkyl, aryloxyalkyl, alkoxyalkyl, cycloalkyl, cycloalkylalkyl, hydroxyl, hydroxyalkyl, heterocyclyl, guanadino, $CONR^{13}R^{14}$, $NR^{15}COOR^{16}$, $NR^{15}COR^{16}$, $NR^{15}CONR^{13}R^{14}$, $NR^{15}SO_2R^{16}$, $OCOR^{16}$, $COOR^{16}$, $OR^{16}$, or $SR^{16}$,
  - $R^4$, when present, is hydrogen, lower alkyl, or aralkyl,
  - $R^5$, when present, is hydrogen, lower alkyl, or aralkyl,
  - $R^6$, when present, is hydrogen, lower alkyl, or aralkyl,
  - $R^7$, when present, is hydrogen, lower alkyl, or aralkyl,
  - $R^8$, when present, is hydrogen, lower alkyl, or aralkyl,
  - $R^9$, when present, is hydrogen, lower alkyl, or aralkyl,
  - $R^{10}$, when present, is hydrogen, lower alkyl, or aralkyl,
  - $R^{11}$, when present, is hydrogen, lower alkyl, or aralkyl,
  - $R^{12}$, when present, is hydrogen, $NR^{21}CONR^{22}R^{23}$, $NR^{21}COR^{24}$, $NR^{21}SO_2R^{24}$, $NR^{21}COOR^{24}$, $OCOR^{24}$, $OR^{24}$, $O(CH_2CH_2O)_sR^{24}$, $COOR^{24}$, alkyl, and hydroxyalkyl, $R^{13}$, when present, is hydrogen, alkyl, aryl, aralkyl, cycloalkyl, cycloalkylalkyl, haloalkyl, heterocyclyl, heterocyclylalkyl, alkoxycarbonyl, or alkoxycarbonylalkyl, $R^{14}$, when present, is hydrogen, alkyl, aryl, aralkyl, cycloalkyl, cycloalkylalkyl, haloalkyl, heterocyclyl, heterocyclylalkyl, alkoxycarbonyl, or alkoxycarbonylalkyl, $R^{15}$, when present, is hydrogen, alkyl, aryl, aralkyl, cycloalkyl, cycloalkylalkyl, heterocyclyl, or heterocyclylalkyl, $R^{16}$, when present, is hydrogen, alkyl, aryl, aralkyl, cycloalkyl, cycloalkylalkyl, haloalkyl, heterocyclyl, heterocyclylalkyl, alkoxycarbonyl, or alkoxycarbonylalkyl, $R^{21}$, when present, is hydrogen, lower alkyl, or aralkyl, $R^{22}$, when present, is alkyl, aryl, aralkyl, cycloalkyl, cycloalkylalkyl, haloalkyl, heterocyclyl, heterocyclylalkyl, alkoxycarbonyl, alkoxycarbonylalkyl, $R^{23}$, when present, is hydrogen, alkyl, aryl, cycloalkyl, cycloalkylalkyl, heterocyclyl, heterocyclylalkyl, or aralkyl, $R^{24}$, when present, is hydrogen, alkyl, aryl, aralkyl, cycloalkyl, cycloalkylalkyl, heterocyclyl, heterocyclylalkyl, haloalkyl, alkoxycarbonyl, or alkoxycarbonylalkyl, $R^{34}$, when present, is alkyl, aralkyl, $COR^{35}$, or $SO_2R^{35}$, $R^{35}$, when present, is alkyl, aryl, or aralkyl l, m, n, and p are integers independently having values 0 and 1, q, r, and s, are integers independently having values ranging between 0 and 6 or any range therebetween, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{21}$, $R^{22}$, $R^{23}$, $R^{24}$, $R^{34}$ and $R^{35}$ when present may independently be either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, hydroxyalkyl, aryloxy, hydroxyaryl, alkoxyaryl, halo, haloalkyl, haloalkoxy, haloaryl, amino, alkylamino, dialkylamino, arylamino, diarylamino, alkoxycarbonyl, alkoxycarbonylalkyl, —NHCO(alkyl), —NHCO(aryl), —NHCO(aralkyl), —NHCO(haloalkyl), —$NHSO_2$(alkyl), —$NHSO_2$(aryl), —$NHSO_2$(aralkyl), —OCO(alkylamino), and —OCO(dialkylamino)

provided that, in certain embodiments, when $M^3$ is $NR^6$, $M^4$ is absent, and $R^{12}$ is $CONR^{22}R^{23}$, then $R^{23}$ is not 1-(1,3-benzodioxol-5-yl)-3-ethoxy-3-oxopropyl, provided that, in certain embodiments, when $M^3$ and $M^4$ are absent, $R^{12}$ is not of the formula AC(=J)EC(H)(MX)TLR$^{25}$ provided that, in certain embodiments, when $R^3$ is hydrogen, alkyl or aryl, $R^{12}$ is not hydrogen, provided that, in certain embodiments, when $R^1$ is phenyl, $R^3$ is benzyloxycarbonylamino, and $R^{12}$ is hydrogen, $R^2$ is not 2-methoxybenzyl, provided that, in certain embodiments, when $R^1$ is alkyl, $R^2$ is aralkyl, provided that, in certain embodiments, when $M^1$ is $SO_2$ and $R^1$ is phenyl, 4-methylphenyl or 2,4,6-trimethylphenyl, $R^2$ is not alkyl, 2-phenethyl, benzyl, or 2-methoxy-2-oxoethyl, provided that, in certain embodiments, when $M^1$ is CO and $R^1$ is 2-furyl, 4-pyridyl, or 3,5-dinitrophenyl, $R^2$ is not alkyl, benzyl or 2-(1H-indol-2-yl)ethyl, provided that, in certain embodiments, when $M^2$ is CO, then $M^6$ is $NR^{34}(CH_2)_q$, wherein q is not 0, provided that, in certain embodiments, when $M^2$ is CO, $M^3$ is O, S, $NR^6$ or $(CR^7R^8)_m$, or provided that, in certain embodiments, when $M^2$ is $SO_2$ or $(CR^4R^5)_l$, $M^3$ is $(CR^7R^8)_m$.

In certain embodiments, the pharmaceutical compositions further include a pharmaceutically acceptable carrier. In other embodiments, the compositions may be formulated for enteral administration in a pharmaceutically acceptable enteral carrier or may be formulated for parenteral administration in a pharmaceutically acceptable parenteral carrier. In other embodiments, the compounds may be used in combination with one or more anti-cancer agents.

Embodiments of this disclosure also provide methods for treating, ameliorating, and/or reducing symptoms of diseases, maladies, cancers, or the like including administering a pharmaceutical composition including an effective amount of one or more (one or a plurality of) integrin activators capable of improving the anti-cancer activity of nature t-cells, wherein the integrin activators target integrins including, but not limited to, α4β1, α4β7, α5β1, αLβ2 and/or αVβ3 improving binding to their respective ligands including, but not limited to, VCAM-1, fibronectin, MAdCAM-1, ICAM-1, ICAM-2, and/or vitronectin, wherein the compositions treat, ameliorate, and/or reduce symptoms of diseases, maladies, cancers, or the like. In certain embodiments, the compositions may also include one or more anti-cancer agents, wherein the compositions treat, ameliorate, and/or reduce symptoms of diseases, maladies, cancers, or the like. In other embodiments, the compositions may be formulated for enteral administration in a pharmaceutically acceptable enteral carrier or may be formulated for parenteral administration in a pharmaceutically acceptable parenteral carrier. In other embodiments, the compounds may be used in combination with one or more anti-cancer agents.

Embodiments of this disclosure provide methods for treating, ameliorating, and/or reducing symptoms of diseases, maladies, cancers, or the like including administering a pharmaceutical compositions including an effective amount of one or more compounds comprising N,N-disubstituted amides, N,N-disubstituted carbamate, N,N-disubstituted urea, and N,N-disubstituted sulfonamide compounds to an animal or human to treat, ameliorate, and/or reduce symptoms of diseases, maladies, cancers, or the like. In certain embodiments, the methods may be enteral administering the compositions and/or parenteral administering the compositions. In other embodiments, the compositions include one or more anti-cancer agents.

In certain embodiments, the chemical compounds are of the general Formula (I):

$$R^1\text{-}M^1\text{-}N(R^2)\text{-}M^2\text{-}M^3\text{-}M^4\text{-}M^5\text{-}M^6\text{-}R^3 \quad (I)$$

wherein:

$R^1$ is alkyl, aryl, aralkyl, cycloalkyl, cycloalkylalkyl, haloalkyl, heterocylcyl, or heterocyclylalkyl, $R^2$ is alkyl, aryl, aralkyl, cycloalkyl, cycloalkylalkyl, haloalkyl, heterocylcyl, or heterocyclylalkyl, $M^1$ is $CH_2$, CO, $SO_2$, or $(CR^4R^5)_l$, $M^2$ is absent, $CH_2$, CO, $SO_2$, or $(CR^4R^5)_l$, $M^3$ is absent, $CH_2$, O, S, $NR^6$, or $(CR^7R^8)_m$, $M^4$ is absent, $CH_2$, or $(CR^9R^{10})_n$, $M^5$ is absent, O,$(CR^{11}R^{12})$, or $(CR^{11}R^{12})_p$, $M^6$ is $(CH_2)_q$, $(CH_2)_q$—CH═CH—$(CH_2)_r$, $(CH_2)_q$-arylene-$(CH_2)_r$, $(CH_2CH_2O)_q$, or $NR^{34}(CH_2)_q$, $R^3$ is hydrogen, alkyl, aryl, aralkyl, aryloxyalkyl, alkoxyalkyl, cycloalkyl, cycloalkylalkyl, hydroxyl, hydroxyalkyl, heterocyclyl, guanadino, $CONR^{13}R^{14}$, $NR^{15}COOR^{16}$, $NR^{15}COR^{16}$, $NR^{15}CONR^{13}R^{14}$, $NR^{15}SO_2R^{16}$, $OCOR^{16}$, $COOR^{16}$, $OR^{16}$, or $SR^{16}$, $R^4$, when present, is hydrogen, lower alkyl, or aralkyl, $R^5$, when present, is hydrogen, lower alkyl, or aralkyl, $R^6$, when present, is hydrogen, lower alkyl, or aralkyl, $R^7$, when present, is hydrogen, lower alkyl, or aralkyl, $R^8$, when present, is hydrogen, lower alkyl, or aralkyl, $R^9$, when present, is hydrogen, lower alkyl, or aralkyl, $R^{10}$, when present, is hydrogen, lower alkyl, or aralkyl, $R^{11}$, when present, is hydrogen, lower alkyl, or aralkyl, $R^{12}$, when present, is hydrogen, $NR^{21}CONR^{22}R^{23}$, $NR^{21}COR^{24}$, $NR^{21}SO_2R^{24}$, $NR^{21}COOR^{24}$, $OCOR^{24}$, $OR^{24}$, $O(CH_2CH_2O)_sR^{24}$, $COOR^{24}$, alkyl, and hydroxyalkyl, $R^{13}$, when present, is hydrogen, alkyl, aryl, aralkyl, cycloalkyl, cycloalkylalkyl, haloalkyl, heterocyclyl, heterocyclylalkyl, alkoxycarbonyl, or alkoxycarbonylalkyl, $R^{14}$, when present, is hydrogen, alkyl, aryl, aralkyl, cycloalkyl, cycloalkylalkyl, haloalkyl, heterocyclyl, heterocyclylalkyl, alkoxycarbonyl, or alkoxycarbonylalkyl, $R^{15}$, when present, is hydrogen, alkyl, aryl, aralkyl, cycloalkyl, cycloalkylalkyl, heterocyclyl, or heterocyclylalkyl, $R^{16}$, when present, is hydrogen, alkyl, aryl, aralkyl, cycloalkyl, cycloalkylalkyl, haloalkyl, heterocyclyl, heterocyclylalkyl, alkoxycarbonyl, or alkoxycarbonylalkyl, $R^{21}$, when present, is hydrogen, lower alkyl, or aralkyl, $R^{22}$, when present, is alkyl, aryl, aralkyl, cycloalkyl, cycloalkylalkyl, haloalkyl, heterocyclyl, heterocyclylalkyl, alkoxycarbonyl, alkoxycarbonylalkyl, $R^{23}$, when present, is hydrogen, alkyl, aryl, cycloalkyl, cycloalkylalkyl, heterocyclyl, heterocyclylalkyl, or aralkyl, $R^{24}$, when present, is hydrogen, alkyl, aryl, aralkyl, cycloalkyl, cycloalkylalkyl, heterocyclyl, heterocyclylalkyl, haloalkyl, alkoxycarbonyl, or alkoxycarbonylalkyl, $R^{34}$, when present, is alkyl, aralkyl, $COR^{35}$, or $SO_2R^{35}$, $R^{35}$, when present, is alkyl, aryl, or aralkyl l, m, n, and p are integers independently having values 0 and 1, q, r, and s, are integers independently having values ranging between 0 and 6 or any range therebetween, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{21}$, $R^{22}$, $R^{23}$, $R^{24}$, $R^{34}$ and $R^{35}$ when present may independently be either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, hydroxyalkyl, aryloxy, hydroxyaryl, alkoxyaryl, halo, haloalkyl, haloalkoxy, haloaryl, amino, alkylamino, dialkylamino, arylamino, diarylamino, alkoxycarbonyl, alkoxycarbonylalkyl, —NHCO(alkyl), —NHCO(aryl), —NHCO(aralkyl), —NHCO(haloalkyl), —$NHSO_2$(alkyl), —$NHSO_2$(aryl), —$NHSO_2$(aralkyl), —OCO(alkylamino), and —OCO(dialkylamino)

provided that, in certain embodiments, when $M^3$ is $NR^6$, $M^4$ is absent, and $R^{12}$ is $CONR^{22}R^{23}$, then $R^{23}$ is not 1-(1,3-benzodioxol-5-yl)-3-ethoxy-3-oxopropyl, provided that, in certain embodiments, when $M^3$ and $M^4$ are absent, $R^{12}$ is not of the formula AC(=J)EC(H)(MX)TLR25 provided that, in certain embodiments, when $R^3$ is hydrogen, alkyl or aryl, $R^{12}$ is not hydrogen, provided that, in certain embodiments, when $R^1$ is phenyl, $R^3$ is benzyloxycarbonylamino, and $R^{12}$ is hydrogen, $R^2$ is not 2-methoxybenzyl, provided that, in certain embodiments, when $R^1$ is alkyl, $R^2$ is aralkyl, provided that, in certain embodiments, when $M^1$ is $SO_2$ and $R^1$ is phenyl, 4-methylphenyl or 2,4,6-trimethylphenyl, $R^2$ is not alkyl, 2-phenethyl, benzyl, or 2-methoxy-2-oxoethyl, provided that, in certain embodiments, when $M^1$ is CO and $R^1$ is 2-furyl, 4-pyridyl, or 3,5-dinitrophenyl, $R^2$ is not alkyl, benzyl or 2-(1H-indol-2-yl)ethyl, provided that, in certain embodiments, when $M^2$ is CO, then $M^6$ is $NR^{34}(CH_2)_q$, wherein q is not 0, provided that, in certain embodiments, when $M^2$ is CO, $M^3$ is O, S, $NR^6$ or $(CR^7R^8)_m$, or provided that, in certain embodiments, when $M^2$ is $SO_2$ or $(CR^4R^5)$, $M^3$ is $(CR^7R^8)_m$.

In certain embodiments, the pharmaceutical compositions further include a pharmaceutically acceptable carrier. In other embodiments, the compositions may be formulated for enteral administration in a pharmaceutically acceptable enteral carrier or may be formulated for parenteral administration in a pharmaceutically acceptable parenteral carrier.

BRIEF DESCRIPTION OF THE DRAWINGS OF THE DISCLOSURE

The disclosure may be better understood with reference to the following detailed description together with the appended illustrative drawings in which like elements are numbered the same:

DEFINITIONS USED IN THE DISCLOSURE

Figure 1:
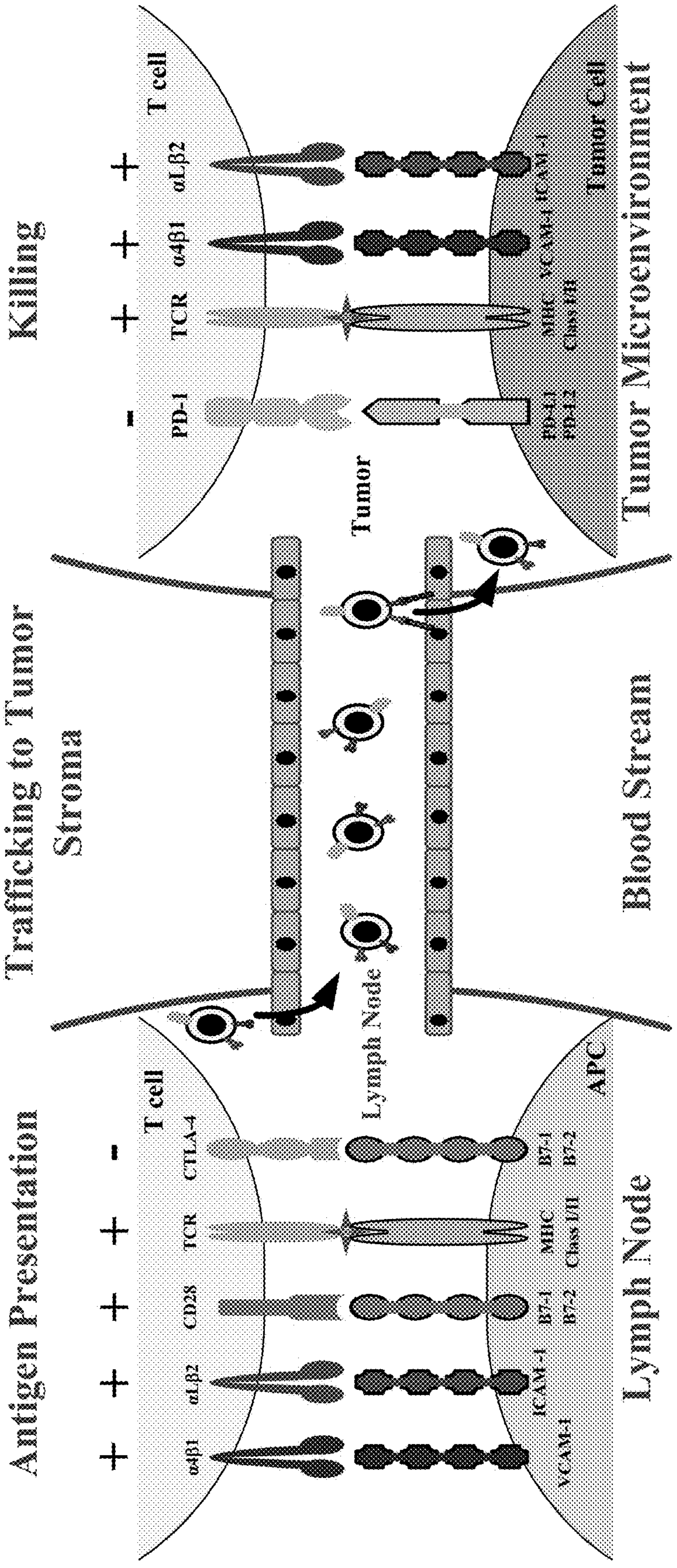
FIG. 1 depicts a schematic diagram of antigen presentation, trafficking to tumor stroma, and killing tumor cells.

In addition to having their customary and usual meaning, the following definitions apply where the context permits in the specification and claims:

The term "at least one" means one or more or one or a plurality, additionally, these three terms may be used interchangeably within this application. For example, at least one device means one or more devices or one device and a plurality of devices.

The term "one or a plurality" means one item or a plurality of items.

The term "about" means that a value of a given quantity is within ±20% of the stated value. In other embodiments, the value is within ±15% of the stated value. In other embodiments, the value is within ±10% of the stated value. In other embodiments, the value is within ±5% of the stated value. In other embodiments, the value is within ±2.5% of the stated value. In other embodiments, the value is within ±1% of the stated value.

The term "substantially" or "essentially" means that a value of a given quantity is within ±5% of the stated value. In other embodiments, the value is within ±2.5% of the stated value. In other embodiments, the value is within ±2% of the stated value. In other embodiments, the value is within ±1% of the stated value. In other embodiments, the value is within ±0.1% of the stated value.

The term "pharmaceutical composition" refers to a mixture of one or more chemicals, or pharmaceutically acceptable salts thereof, with a suitable carrier, for administration to a mammal as a medicine.

The term "therapeutically effective amount" refers to that amount of the compound being administered that will relieve at least to some extent one or more of the symptoms of the disorder being treated. For example, an amount of the compound effective to prevent, alleviate or ameliorate symptoms of disease or prolong the survival of the subject being treated. In certain embodiments, the therapeutically effective amount or simply effective amount of one or more compounds of Formula (I) is that which may result in a systemic plasma concentration that ranges between about 1 fM and about 500 μM. In other embodiments, the effective amount ranges between about 1 fM and about 400 μM. In other embodiments, the effective amount ranges between about 1 fM and about 300 μM. In other embodiments, the effective amount ranges between about 1 fM and about 200 μM. In other embodiments, the effective amount ranges between about 1 fM and about 100 μM. In other embodiments, the effective amount ranges between about 1 fM and about 75 μM. In other embodiments, the effective amount ranges between about 1 fM and about 50 μM. In other embodiments, the effective amount ranges between about 1 fM and about 25 μM. In other embodiments, the effective amount ranges between about 1 fM and about 10 μM. In other embodiments, the effective amount ranges between about 1 fM and about 1 μM. In other embodiments, the effective amount ranges between about 1 fM and about 750 nM. In other embodiments, the effective amount ranges between about 1 fM and about 500 nM. In other embodiments, the effective amount ranges between about 1 fM and about 250 nM. In other embodiments, the effective amount ranges between about 1 fM and about 100 nM. In other embodiments, the effective amount ranges between about 1 fM and about 75 nM. In other embodiments, the effective amount ranges between about 1 fM and about 50 nM. In other embodiments, the effective amount ranges between about 1 fM and about 25 nM. Of course, an ordinary artisan should recognize that all of the above ranges include all sub-ranges, e.g., 1 fM to 500 μM, would include any of the sub-ranges having a value between 1 fM and 500 μM.

The term "pharmaceutically acceptable carrier" means any carrier approved for or may later be approved for administration to humans or animals.

With respect to a disease or disorder, the term "treatment" refers to preventing, deterring the occurrence of the disease or disorder, arresting, regressing, or providing relief from symptoms or side effects of the disease or disorder and/or prolonging the survival of the subject being treated.

The term "halo" or "halogen" as used herein refers to I, Br, Cl or F.

The term "carbyl" or "hydrocarbyl" group means a group including carbon atoms with sufficient hydrogen atoms to satisfy the valency of the compounds, wherein one or more of the carbon atoms may be replaced by oxygen atoms and one or more of the hydrogen atoms may be replaced with F, Cl, amides, or other group often used to replace hydrogen atoms. The groups may be linear, branched, cyclical, aromatic, or including linear, branched, cyclical, and aromatic moieties. The groups broadly encompass all of the specific group listed below.

The term "alkyl" as used herein alone or in combination refers to $C_1$-$C_{12}$ straight or branched, substituted or unsubstituted saturated chain radicals derived from saturated hydrocarbons by the removal of one hydrogen atom. Representative examples of alkyl groups include methyl, ethyl, n-propyl, iso-propyl, n-butyl, sec-butyl, iso-butyl, and tert-butyl among others.

The term "alkenyl", alone or in combination, refers to a substituted or unsubstituted straight-chain or substituted or unsubstituted branched-chain alkenyl radical containing from 2 to 10 carbon atoms. Examples of such radicals include, but are not limited to, ethenyl, E- and Z-pentenyl, decenyl and the like.

The term "alkynyl", alone or in combination, refers to a substituted or unsubstituted straight or substituted or unsubstituted branched chain alkynyl radical containing from 2 to 10 carbon atoms. Examples of such radicals include, but are not limited to ethynyl, propynyl, propargyl, butynyl, hexynyl, decynyl and the like.

The term "lower" modifying "alkyl", "alkenyl", "alkynyl" or "alkoxy" refers to a $C_1$-$C_6$ unit for a particular functionality. For example lower alkyl means $C_1$-$C_6$ alkyl.

The term "cycloalkyl" as used herein alone or in combination refers to a substituted or unsubstituted aliphatic ring system having 3 to 10 carbon atoms and 1 to 3 rings, including, but not limited to cyclopropyl, cyclopentyl, cyclohexyl, norbornyl, and adamantyl among others. Cycloalkyl groups can be unsubstituted or substituted with one, two or three substituents independently selected from lower alkyl, haloalkyl, alkoxy, thioalkoxy, amino, alkylamino, dialkylamino, hydroxy, halo, mercapto, nitro, carboxaldehyde, carboxy, alkoxycarbonyl and carboxamide. This term is meant to encompass cycloalkenyl and cycloalkynyl groups. "Cycloalkyl" includes cis or trans forms. Furthermore, the substituents may either be in endo or exo positions in the bridged bicyclic systems.

The term "cycloalkenyl" as used herein alone or in combination refers to a cyclic carbocycle containing from 4 to 8 carbon atoms and one or more double bonds. Examples of such cycloalkenyl radicals include, but are not limited to, cyclopentenyl, cyclohexenyl, cyclopentadienyl and the like.

The term "cycloalkylalkyl" as used herein refers to a cycloalkyl group appended to a lower alkyl radical, including, but not limited to cyclohexyl methyl.

The term "haloalkyl" as used herein refers to a lower alkyl radical, to which is appended at least one halogen substituent, for example chloromethyl, fluoroethyl, trifluoromethyl and pentafluoroethyl among others.

The term “alkoxy”, alone or in combination, refers to an alkyl ether radical, wherein the term “alkyl” is as defined above. Examples of suitable alkyl ether radicals include, but are not limited to, methoxy, ethoxy, n-propoxy, iso-propoxy, n-butoxy, iso-butoxy, sec-butoxy, tert-butoxy and the like.

The term “alkenoxy”, alone or in combination, refers to a radical of formula alkenyl-O—, provided that the radical is not an enol ether, wherein the term “alkenyl” is as defined above. Examples of suitable alkenoxy radicals include, but are not limited to, allyloxy, E- and Z-3-methyl-2-propenoxy and the like.

The term “alkynoxy”, alone or in combination, refers to a radical of formula alkynyl-O—, provided that the radical is not an -ynol ether. Examples of suitable alkynoxy radicals include, but are not limited to, propargyloxy, 2-butynyloxy and the like.

The term “carboxyl” as used herein refers to —$CO_2H$.

The term “thioalkoxy”, refers to a thioether radical of formula alkyl-S—, wherein “alkyl” is as defined above.

The term “carboxaldehyde” as used herein refers to —C(O)R wherein R is hydrogen.

The term “carboxamide” as used herein refers to —C(O)$NR_2$ wherein R is hydrogen, alkyl or any other suitable substituent.

The term “alkoxyalkoxy” as used herein refers to $R_bO$—$R_cO$— wherein $R_b$ is lower alkyl as defined above and $R_c$ is alkylene wherein alkylene is —$(CH_2)_{n'}$— wherein n' is an integer from 1 to 6. Representative examples of alkoxyalkoxy groups include methoxymethoxy, ethoxymethoxy, and t-butoxymethoxy among others.

The term “alkylamino” as used herein refers to $R_dNH$— wherein $R_d$ is a lower alkyl group, for example, ethylamino, butylamino, among others.

The term “alkenylamino” alone or in combination, refers to a radical of formula alkenyl-NH— or $(alkenyl)_2N$—, wherein the term “alkenyl” is as defined above, provided that the radical is not an enamine. An example of such alkenylamino radicals is the allylamino radical.

The term “alkynylamino”, alone or in combination, refers to a radical of formula alkynyl-NH— or $(alkynyl)_2N$— wherein the term “alkynyl” is as defined above, provided that the radical is not an amine. An example of such alkynylamino radicals is the propargyl amino radical.

The term “dialkylamino” as used herein refers to $R_eR_fN$— wherein $R_e$ and $R_f$ are independently selected from lower alkyl, for example diethylamino, and methyl propylamino, among others.

The term “amino” as used herein refers to $H_2N$—.

The term “alkoxycarbonyl” as used herein refers to an alkoxyl group as previously defined appended to the parent molecular moiety through a carbonyl group. Examples of alkoxycarbonyl include methoxycarbonyl, ethoxycarbonyl, and isopropoxycarbonyl among others.

The term “aryl” or “aromatic” as used herein alone or in combination refers to a substituted or unsubstituted carbocyclic aromatic group having about 6 to 12 carbon atoms such as phenyl, naphthyl, indenyl, indanyl, azulenyl, fluorenyl and anthracenyl; or a heterocyclic aromatic group selected from the group consisting of furyl, thienyl, pyridyl, pyrrolyl, oxazolyl, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, isoquinolinyl, cinnolinyl, phthalazinyl, quinazolinyl, quinoxalinyl, 1,8-naphthridinyl, pteridinyl, carbazolyl, acridinyl, phenazinyl, phenothiazinyl, phenoxyazinyl, pyrazolo[1,5-c]triazinyl and the like. “Arylalkyl” and “alkylaryl” employ the term “alkyl” as defined above. Rings may be multiply substituted. Aromatic rings may be fused with other aromatic or non-aromatic rings to form multicyclic rings, and are also encompassed by the term “aromatic,” as used herein.

The term “aralkyl”, alone or in combination, refers to an aryl substituted alkyl radical, wherein the terms “alkyl” and “aryl” are as defined above. Examples of suitable aralkyl radicals include, but are not limited to, phenylmethyl, phenethyl, phenylhexyl, diphenylmethyl, pyridylmethyl, tetrazolyl methyl, furylmethyl, imidazolyl methyl, indolylmethyl, thienylpropyl and the like.

The term “aralkenyl”, alone or in combination, refers to an aryl substituted alkenyl radical, wherein the terms “aryl” and “alkenyl” are as defined above.

The term “arylamino”, alone or in combination, refers to a radical of formula aryl-NRg-, wherein “aryl” is as defined above. Rg may be selected from the group consisting of H, lower alkyl, aryl and aralkyl among others. Examples of arylamino radicals include, but are not limited to, phenylamino(anilido), naphthlamino, 2-, 3-, and 4-pyridylamino and the like.

The term “biaryl”, alone or in combination, refers to a radical of formula aryl-aryl, wherein the term “aryl” is as defined above.

The term “thioaryl”, alone or in combination, refers to a radical of formula aryl-S—, wherein the term “aryl” is as defined above. An example of a thioaryl radical is the thiophenyl radical.

The term “aroyl”, alone or in combination, refers to a radical of formula aryl-CO—, wherein the term “aryl” is as defined above. Examples of suitable aromatic acyl radicals include, but are not limited to, benzoyl, 4-halobenzoyl, 4-carboxybenzoyl, naphthoyl, pyridylcarbonyl and the like.

The term “heterocyclyl”, alone or in combination, refers to a non-aromatic 3- to 10-membered ring containing at least one endocyclic N, O, or S atom. The heterocycle may be optionally aryl-fused. The heterocycle may also optionally be substituted with at least one substituent which is independently selected from the group consisting of hydrogen, halogen, hydroxyl, amino, nitro, trifluoromethyl, trifluoromethoxy, alkyl, aralkyl, alkenyl, alkynyl, aryl, cyano, carboxyl, alkoxycarbonyl, carboxyalkyl, oxo, arylsulfonyl and aralkylaminocarbonyl among others.

The term “alkylheterocyclyl” as used herein refers to an alkyl group as previously defined appended to the parent molecular moiety through a heterocyclyl group.

The term “heterocyclylalkyl” as used herein refers to a heterocyclyl group as previously defined appended to the parent molecular moiety through an alkyl group.

The term “aminal” as used herein refers to a hemi-acetal of the structure $RCH(NH_2)(OH)$.

The terms “electron-withdrawing” or “electron-donating” substituents refer to the ability of a substituent to withdraw or donate electrons relative to that of hydrogen if hydrogen occupied the same position in the molecule. These terms are well-understood by one skilled in the art and are discussed in ADVANCED ORGANIC CHEMISTRY by J. March, 1985, pp. 16-18, incorporated herein by reference. Electron withdrawing groups include halo, nitro, carboxyl, lower alkenyl, lower alkynyl, carboxaldehyde, carboxyamido, aryl, quaternary ammonium, trifluoromethyl, and aryl lower alkanoyl among others. Electron donating groups include such groups as hydroxy, lower alkyl, amino, lower alkylamino, di(lower alkyl)amino, aryloxy, mercapto, lower alkylthio, lower alkylmercapto, and disulfide among others. One skilled in the art will appreciate that the aforesaid substituents may have electron donating or electron withdrawing properties under different chemical conditions. Moreover, the present disclosure contemplates any combination of substituents selected from the above-identified groups.

In certain embodiments, the electron donating or electron withdrawing substituents are halo, nitro, alkanoyl, carboxaldehyde, arylalkanoyl, aryloxy, carboxyl, carboxamide, cyano, sulfonyl, sulfoxide, heterocyclyl, guanidine, quaternary ammonium, lower alkenyl, lower alkynyl, sulfonium salts, hydroxy, lower alkoxy, lower alkyl, amino, lower alkylamino, di(lower alkyl)amino, amine lower alkyl mercapto, mercaptoalkyl, alkylthio and alkyldithio.

Use of the above terms is meant to encompass substituted and unsubstituted moieties. Substitution may be by one or more groups such as alcohols, ethers, esters, amides, sulfones, sulfides, hydroxyl, nitro, cyano, carboxy, amines, heteroatoms, lower alkyl, lower alkoxy, lower alkoxycarbonyl, alkoxyalkoxy, acyloxy, halogens, trifluoromethoxy, trifluoromethyl, alkyl, aralkyl, alkenyl, alkynyl, aryl, cyano, carboxy, carboalkoxy, carboxyalkyl, cycloalkyl, cycloalkylalkyl, heterocyclyl, alkylheterocyclyl, heterocyclylalkyl, oxo, arylsulfonyl and aralkylaminocarbonyl or any of the substituents of the preceding paragraphs or any of those substituents either attached directly or by suitable linkers. The linkers are typically short chains of 1-3 atoms containing any combination of —C—, —C(O)—, —NH—, —S—, —S(O)—, —O—, —C(O)O— or —S(O)O—. Rings may be substituted multiple times.

The term "mammals" includes humans and other animals.

The term "heteroatom" as used herein encompasses nitrogen, sulfur and oxygen.

The term "alpha" as used herein indicates the position immediately adjacent to the position described.

The term "pharmaceutically acceptable pro-drugs" as used herein represents those pro-drugs of the disclosed compounds which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the disclosed compounds. Pro-drugs according to certain embodiments may be rapidly transformed in vivo to the parent compound of the above formula, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987), hereby incorporated by reference.

The term "excipient" as used herein means any substance other than the active drug or product which has been appropriately evaluated for safety and is included in a drug delivery system to either aid the processing of the drug delivery system during its manufacture; protect, support, or enhance stability, bioavailability, or patient acceptability; assist in product identification; or enhance any other attribute of the overall safety and effectiveness of the drug delivery system during storage or use (40 CFR 63.1251).

The term "solid tumor" as used herein means an abnormal mass of tissue that usually does not contain cysts or liquid areas. Solid tumors may be benign (not cancer), or malignant (cancer). Different types of solid tumors are named for the type of cells that form them. Examples of solid tumors are sarcomas, carcinomas, and lymphomas.

The term "effector cell" as used herein means a cell that has been activated by their cognate tumor-antigen, and involved in eliminating a cancer cell.

The term "adoptive T-cell" is a effector cell that is derived from a naive T-cell or activated T-cell capable of effector functions.

The term "agonist" or "activator", which may be used interchangeably, means a substance that initiates a physiological response when combined with a receptor. In the present invention, the terms mean one or more compounds of Formula (I), which activate integrins such as $\alpha4\beta1$, $\alpha4\beta7$, $\alpha5\beta1$, $\alpha L\beta2$ and/or $\alpha V\beta3$.

The term "enteral administration" means administration modes via a human, a mammal, or an animal gastrointestinal tract. Enteral administration involves the esophagus, stomach, and small and large intestines (i.e., the gastrointestinal tract) and include, without limitation, oral administration, sublingual administration (dissolving the drug under the tongue), and rectal administration.

The term "parenteral administration" means administration modes to a human, a mammal, or an animal via injection, indwelling catheter, or administration to non-GI tract areas of the human, mammal or animal. Modes of parenteral administration include, without limitation, epidural (synonym: peridural) administration (i.e., injection or infusion into the epidural space), intracerebral administration (i.e., direct injection into the brain), intracerebroventricular administration, transdermal administration, e.g., a patch, epicutaneous administration, sublingual and buccal administration, extra-amniotic administration, nasal administration, intra-arterial administration, intra-articular administration, intracardiac administration, intracavernous injection administration, intradermal administration, intralesional administration, intramuscular administration, intraocular administration, intraosseous infusion administration, intraperitoneal administration, intrathecal administration, intrauterine administration, intravaginal administration, intravenous administration, intravesical infusion administration, intravitreal administration, subcutaneous administration, perivascular administration, transmucosal administration, or other non-GI administration modes.

Abbreviations Used in the Disclosure

The following abbreviations are used herein: Ac acetyl AcOH, acetic acid 6-Ahx-OH 6-aminohexanoic acid, Bz benzyl, Boc tert-butyloxycarbonyl, nBu n-butyl, nBuLi n-butyllithium, 1.6M in hexanes (unless other concentration noted), BzOCO benzyloxycarbonyl, CDI N,N'-carbonyldiimidazole, COMU (1-cyano-2-ethoxy-2-oxoethylidenaminooxy) dimethylamino-morpholino-carbenium hexafluorophosphate, DAB 2,4-diaminobutyryl, DBU 1,8-diazabicyclo[5.4.0]undec-7-ene, DCE 1,2-dichloroethane, DCHA dicyclohexylamine, DCM dichloromethane (methlyene chloride) dioxane 1,4-dioxane, DIPEA N,N-diisopropylethylamine DMED N,N'-dimethylethylene diamine, DMF N,N-dimethylformamide, DMSO dimethylsulfoxide, Et ethyl, EtOH ethanol, Fmoc 9H-fluoren-9-ylmethyloxycarbonyl, Glu glutamic acid, Gly glycine HBTU O-(Benzotriazol-1-yl)-N,N,N',N'-tetramethyluronium hexafluorophosphate, HMDS hexamethyldisilazane, iPr isopropyl, KHMDS potassium bis(trimethylsilyl)amide, Lys lysine, LHMDS lithium bis(trimethylsilyl)amide, Me methyl, MeOH methanol, Nle norleucine, NMM 4-methylmorpholine, NSMC N-succinimidyl-N-methylcarbamate, OAc acetate, Orn Ornithine, pTsOH para-toluenesulfonic acid, Ph phenyl, Bz benzyl, RT room temperature, tBu tert-butyl, TEA triethylamine, Tfa trifluoroacetyl, THF tetrahydrofuran, Tol toluene, and Tyr tyrosine.

DETAILED DESCRIPTION OF THE DISCLOSURE

The inventors have found that one or more N,N-disubstituted amide compounds, N,N-disubstituted carbamate compounds, N,N-disubstituted urea compounds, and/or N,N-disubstituted sulfonamide compounds may be administered to a human or an animal to treat, ameliorate, and/or reduce symptoms of diseases, maladies, cancers, cancerous growths, solid tumors, or other cancerous maladies. The compounds are known to enhance integrin-mediated adhesion, are known to enhance the activity of integrin-expressing cells, and are known to enhance adoptive cell therapies, wherein the integrins targeted by these compounds include, but are not limited to, α4β1, α4β7, α5β1, αLβ2 and βVβ3 and their corresponding ligands include, but are not limited to, VCAM-1, fibronectin, MAdCAM-1, ICAM-1, ICAM-2, and/or vitronectin. However, there is no teaching that the compounds themselves found be capable of broad spectrum anti-cancer activity, which the inventors have now discovered. In other embodiments, the compounds may be used in combination with one or more anti-cancer agents.

The inventors have found that one or more N,N-disubstituted amide compounds, N,N-disubstituted carbamate compounds, N,N-disubstituted urea compounds, and/or N,N-disubstituted sulfonamide compounds may be effective for prompting an immune response to cancer antigens, for priming and activating antigen presenting cells and T-cells, for trafficking nature and activated T-cells into tumor, for prompting the infiltration of nature and activated T-cells into tumors, for prompting the recognition of cancer cells by natural and activated T-cells, and for prompting cancer cell killing via natural and activated T-cells.

Embodiments of the disclosure broadly relate to pharmaceutical compositions including an effective amount of one or more compounds comprising N,N-disubstituted amide compounds, N,N-disubstituted carbamate compounds, N,N-disubstituted urea compounds, and/or N,N-disubstituted sulfonamide compounds, wherein the compounds treat, ameliorate, and/or reduce symptoms of diseases, maladies, cancers, cancerous growths, solid tumors, or other cancerous maladies, or the like. In certain embodiments, the compositions may be formulated for enteral administration or may be formulated for parenteral administration. In other embodiments, the compositions may be formulated for enteral administration in a pharmaceutically acceptable enteral carrier or may be formulated for parenteral administration in a pharmaceutically acceptable parenteral carrier. In other embodiments, the compounds may be used in combination with one or more anti-cancer agents.

In certain embodiments, the chemical compounds have the general Formula (I):

$$R^1\text{-}M^1\text{-}N(R^2)\text{-}M^2\text{-}M^3\text{-}M^4\text{-}M^5\text{-}M^6\text{-}R^3 \quad \text{(I)}$$

wherein:

$R^1$ is alkyl, aryl, aralkyl, cycloalkyl, cycloalkylalkyl, haloalkyl, heterocylcyl, or heterocyclylalkyl, $R^2$ is alkyl, aryl, aralkyl, cycloalkyl, cycloalkylalkyl, haloalkyl, heterocylcyl, or heterocyclylalkyl, $M^1$ is $CH_2$, CO, $SO_2$, or $(CR^4R^5)_l$, $M^2$ is absent, $CH_2$, CO, $SO_2$, or $(CR^4R^5)_l$, $M^3$ is absent, $CH_2$, O, S, $NR^6$, or $(CR^7R^8)_m$, $M^4$ is absent, $CH_2$, or $(CR^9R^{10})_n$, $M^5$ is absent, O,$(CR^{11}R^{12})$, or $(CR^{11}R^{12})_p$, $M^6$ is $(CH_2)_q$, $(CH_2)_q$—CH═CH—$(CH_2)_r$, $(CH_2)_q$-arylene-$(CH_2)_r$, $(CH_2CH_2O)_q$, or $NR^{34}(CH_2)_q$, $R^3$ is hydrogen, alkyl, aryl, aralkyl, aryloxyalkyl, alkoxyalkyl, cycloalkyl, cycloalkylalkyl, hydroxyl, hydroxyalkyl, heterocyclyl, guanadino, $CONR^{13}R^{14}$, $NR^{15}COOR^{16}$, $NR^{15}COR^{16}$, $NR^{15}CONR^{13}R^{14}$, $NR^{15}SO_2R^{16}$, $OCOR^{16}$, $COOR^{16}$, $OR^{16}$, or $SR^{16}$, $R^4$, when present, is hydrogen, lower alkyl, or aralkyl, $R^5$, when present, is hydrogen, lower alkyl, or aralkyl, $R^6$, when present, is hydrogen, lower alkyl, or aralkyl, $R^7$, when present, is hydrogen, lower alkyl, or aralkyl, $R^8$, when present, is hydrogen, lower alkyl, or aralkyl, $R^9$, when present, is hydrogen, lower alkyl, or aralkyl, $R^{10}$, when present, is hydrogen, lower alkyl, or aralkyl, $R^{11}$, when present, is hydrogen, lower alkyl, or aralkyl, $R^{12}$, when present, is hydrogen, $NR^{21}CONR^{22}R^{23}$, $NR^{21}COR^{24}$, $NR^{21}SO_2R^{24}$, $NR^{21}COOR^{24}$, $OCOR^{24}$, $OR^{24}$, $O(CH_2CH_2O)_sR^{24}$, $COOR^{24}$, alkyl, and hydroxyalkyl, $R^{13}$, when present, is hydrogen, alkyl, aryl, aralkyl, cycloalkyl, cycloalkylalkyl, haloalkyl, heterocyclyl, heterocyclylalkyl, alkoxycarbonyl, or alkoxycarbonylalkyl, $R^{14}$, when present, is hydrogen, alkyl, aryl, aralkyl, cycloalkyl, cycloalkylalkyl, haloalkyl, heterocyclyl, heterocyclylalkyl, alkoxycarbonyl, or alkoxycarbonylalkyl, $R^{15}$, when present, is hydrogen, alkyl, aryl, aralkyl, cycloalkyl, cycloalkylalkyl, heterocyclyl, or heterocyclylalkyl, $R^{16}$, when present, is hydrogen, alkyl, aryl, aralkyl, cycloalkyl, cycloalkylalkyl, haloalkyl, heterocyclyl, heterocyclylalkyl, alkoxycarbonyl, or alkoxycarbonylalkyl, $R^{21}$, when present, is hydrogen, lower alkyl, or aralkyl, $R^{22}$, when present, is alkyl, aryl, aralkyl, cycloalkyl, cycloalkylalkyl, haloalkyl, heterocyclyl, heterocyclylalkyl, alkoxycarbonyl, alkoxycarbonylalkyl, $R^{23}$, when present, is hydrogen, alkyl, aryl, cycloalkyl, cycloalkylalkyl, heterocyclyl, heterocyclylalkyl, or aralkyl, $R^{24}$, when present, is hydrogen, alkyl, aryl, aralkyl, cycloalkyl, cycloalkylalkyl, heterocyclyl, heterocyclylalkyl, haloalkyl, alkoxycarbonyl, or alkoxycarbonylalkyl, $R^{34}$, when present, is alkyl, aralkyl, $COR^{35}$, or $SO_2R^{35}$, $R^{35}$, when present, is alkyl, aryl, or aralkyl l, m, n, and p are integers independently having values 0 and 1, q, r, and s, are integers independently having values ranging between 0 and 6 or any range therebetween, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{21}$, $R^{22}$, $R^{23}$, $R^{24}$, $R^{34}$ and $R^{35}$ when present may independently be either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, hydroxyalkyl, aryloxy, hydroxyaryl, alkoxyaryl, halo, haloalkyl, haloalkoxy, haloaryl, amino, alkylamino, dialkylamino, arylamino, diarylamino, alkoxycarbonyl, alkoxycarbonylalkyl, —NHCO(alkyl), —NHCO(aryl), —NHCO(aralkyl), —NHCO(haloalkyl), —$NHSO_2$(alkyl), —$NHSO_2$(aryl), —$NHSO_2$(aralkyl), —OCO(alkylamino), and —OCO(dialkylamino)

provided that, in certain embodiments, when $M^3$ is $NR^6$, $M^4$ is absent, and $R^{12}$ is $CONR^{22}R^{23}$, then $R^{23}$ is not 1-(1,3-benzodioxol-5-yl)-3-ethoxy-3-oxopropyl, provided that, in certain embodiments, when $M^3$ and $M^4$ are absent, $R^{12}$ is not of the formula AC(=J)EC(H)(MX)TL$R^{25}$, provided that, in certain embodiments, when $R^3$ is hydrogen, alkyl or aryl, $R^{12}$ is not hydrogen, provided that, in certain embodiments, when $R^1$ is phenyl, $R^3$ is benzyloxycarbonylamino, and $R^{12}$ is hydrogen, $R^2$ is not 2-methoxybenzyl, provided that, in certain embodiments, when $R^1$ is alkyl, $R^2$ is aralkyl, provided that, in certain embodiments, when $M^1$ is $SO_2$ and $R^1$ is phenyl, 4-methylphenyl or 2,4,6-trimethylphenyl, $R^2$ is not alkyl, 2-phenethyl, benzyl, or 2-methoxy-2-oxoethyl, provided that, in certain embodiments, when $M^1$ is CO and $R^1$ is 2-furyl, 4-pyridyl, or 3,5-dinitrophenyl, $R^2$ is not alkyl, benzyl or 2-(1H-indol-2-yl)ethyl, provided that, in certain embodiments, when $M^2$ is CO, then $M^6$ is $NR^{34}(CH_2)_q$, wherein q is not 0, provided that, in certain embodiments, when $M^2$ is CO, $M^3$ is O, S, $NR^6$ or $(CR^7R^8)_m$, or provided that, in certain embodiments, when $M^2$ is $SO_2$ or $(CR^4R^5)$, $M^3$ is $(CR^7R^8)_m$.

In other embodiments, the chemical compounds are given by general Formula (II):

$$R^1\text{-}M^1\text{-}N(R^2)\text{-}M^2\text{-}M^3\text{-}M^4\text{-}M^5\text{-}M^6\text{-}R^3 \quad \text{(II)}$$

wherein:

$R^1$ is selected from the group consisting of aryl and aralkyl, $R^2$ is alkyl, aryl, or aralkyl, $M^1$ is $CH_2$, $M^2$ is CO, $M^3$ is O, S, or $NR^6$, $R^6$ when present is hydrogen or lower alkyl, $M^4$ is absent or $CH_2$, $M^5$ is $(CR^{11}R^{12})$, $R^{11}$ is hydrogen, $R^{12}$ is selected from the group consisting of hydrogen, $NR^{21}CONR^{22}R^{23}$, $NR^{21}COR^{24}$, $NR^{21}SO_2R^{24}$, $NR^{21}COOR^{24}$, $OCOR^{24}$, $OR^{24}$, $O(CH_2CH_2O)_sR^{24}$, $COOR^{24}$, alkyl, and hydroxyalkyl, s is an integer of 1 to 6, $R^{21}$ and $R^{22}$ when present are independently selected from the group consisting of hydrogen or lower alkyl, $R^{23}$ when present is selected from the group consisting of hydroxyalkyl, alkoxyalkyl, alkyl, aryl, aralkyl and alkoxycarbonylalkyl, provided that when $M^3$ is $NR^6$, $M^4$ is absent, and $R^{12}$ is $CONR^{22}R^{23}$, then $R^{23}$ is not 1-(1,3-benzodioxol-5-yl)-3-ethoxy-3-oxopropyl, $R^{24}$ when present is selected from the group consisting of alkyl, aryl, aralkyl, heterocyclyl, cycloalkyl, cycloalkylalkyl, and heterocyclylalkyl, $M^6$ is $(CH_2)_q$, q is an integer from 0 to 6, $R^3$ is selected from the group consisting of hydrogen, $CONR^{13}R^{14}$, $NR^{15}COOR^{16}$, $NR^{15}COR^{16}$, $NR^{15}CO NR^{13}R^{14}$, $NR^{15}SO_2R^{16}$, $OCOR^{16}$, $COOR^{16}$, $OR^{16}$, $SR^{16}$, heterocyclyl, hydroxyl, hydroxyalkyl, guanadino, alkyl and aryl, $R^{13}$ and $R^{15}$ when present are independently hydrogen or lower alkyl, $R^{14}$ and $R^{16}$ when present are independently selected from the group consisting of hydrogen, alkyl, aryl, aralkyl, cycloalkyl, heterocyclyl, cycloalkylalkyl, and heterocyclylalkyl, $R^1$, $R^2$, $R^3$, $R^{12}$, $R^{14}$, $R^{16}$, $R^{23}$ and $R^{24}$ when present may independently be either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(aralkyl), —NHCO(haloalkyl), —$NHSO_2$(alkyl), —$NHSO_2$(aryl), —$NHSO_2$(aralkyl), alkoxycarbonyl, alkoxycarbonylalkyl, —OCO(alkylamino), and —OCO(dialkylamino).

In other embodiments, the compounds are given by the general Formula (III):

$$R^1\text{-}M^1\text{-}N(R^2)\text{-}M^2\text{-}M^3\text{-}M^4\text{-}M^5\text{-}M^6\text{-}R^3 \quad \text{(III)}$$

wherein:

$R^1$ is aryl or aralkyl, $R^2$ is alkyl, aryl or aralkyl, $M^1$ is $CH_2$, $M^2$ is CO, $M^3$ is absent, $M^4$ is absent or is $CH_2$, $M^5$ is $(CR^{11}R^{12})$, $M^6$ is $(CH_2)_q$, q is an integer of 0 to 6, $R^{11}$ is hydrogen, and $R^{12}$ is selected from the group consisting of hydrogen, $NR^{21}CONR^{22}R^{23}$, $NR^{21}COR^{24}$, $NR^{21}SO_2R^{24}$, $NR^{21}COOR^{24}$, $OCOR^{24}$, $OR^{24}$, $SCOR^{24}$, $SR^{24}$, $N_3$, CN, and $O(CH_2CH_2O)_sR^{24}$, s is an integer of 1 to 6, $R^{21}$ and $R^{22}$ when present are independently selected from the group consisting of hydrogen, lower alkyl, or aralkyl, $R^{23}$ when present is selected from the group consisting of hydroxyalkyl, alkoxyalkyl, alkyl, aryl, aralkyl, and alkoxycarbonylalkyl, $R^{24}$ when present is selected from the group consisting of alkyl, aryl, aralkyl, heterocyclyl, cycloalkyl, cycloalkylalkyl and heterocyclylalkyl, provided that when $M^3$ and $M^4$ are absent, $R^{12}$ is not of the formula:

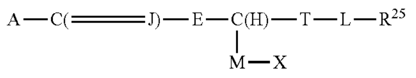

A is selected from the group consisting of —O—, —S—, and —$NR^{26}$—,

E is selected from the group consisting of —$CH_2$—, —O—, —S—, and —$NR^{27}$—,

J is selected from the group consisting of —O—, —S—, and —$NR^{28}$—,

T is selected from the group consisting of CO and $(CH_2)_2$ b is an integer of zero to three, L is selected from the group consisting of —$(CH_2)_n$—, —O—, —S—, and —$NR^{29}$— n is an integer of zero to three,

M is selected from the group consisting of $CR^{30}R^{31}$ and $(CH_2)_u$ u is an integer of zero or one, X is selected from the group consisting of $CO_2B$, $PO_3H_2$, $SO_3H$, $OPO_3H_2$, $CONHCOR^{32}$, $CONHSO_2R^{33}$, oxazolyl, tetrazolyl and hydrogen, B, $R^{25}$, $R^{26}$, $R^{27}$, $R^{28}$, $R^{29}$, $R^{30}$, $R^{31}$, $R^{32}$ and $R^{33}$ are independently selected from the group consisting of hydrogen, halogen alkyl, alkenyl, alkynyl, alkoxy, alkenoxy, alkynoxy, thioalkoxy, aliphatic acyl, —$CF_3$, nitro, amino, cyano, $N(C_1$-$C_3$ alkyl)$CO(C_1$-$C_3$ alkyl), $C_1$-$C_3$ alkylamino, alkenylamino, alkynylamino, di($C_1$-$C_3$ alkyl)amino, $CO_2(C_1$-$C_3$ alkylamino), CONH($C_1$-$C_3$ alkylamino), CH═NOH, $PO_3H_2$, $OPO_3H_2$, $CON(C_1$-$C_3$ alkyl$)_2$, haloalkyl, alkoxycarbonyl, alkoxyalkoxy, carboxaldehyde, carboxamide, cycloalkyl, cycloalkenyl, cycloalkynyl, aryl, aroyl, aryloxy, arylamino, biaryl, thioaryl, heterocyclyl, heterocycloyl, alkylaryl, aralkenyl, aralkyl, alkylheterocyclyc, heterocyclycalkyl, sulfonyl, sulfonamide, carbamate, aryloxyalkyl, carboxyl and CONH(benzyl), B, X, $R^{25}$, $R^{26}$, $R^{27}$, $R^{28}$, $R^{29}$, $R^{30}$, $R^{31}$ and $R^{32}$ are unsubstituted or substituted with at least one electron donating or electron withdrawing group, $R^3$ is selected from the group of hydrogen, $NR^{15}COOR^{16}$, $NR^{15}COR^{16}$, $NR^{15}CONR^{13}R^{14}$, $NR^{15}SO_2R^{16}$, $OCOR^{16}$, $COOR^{16}$, alkyl, $SR^{16}$, heterocyclyl, hydroxyl, hydroxyalkyl, guanadino and aryl, $R^{13}$ and $R^{15}$ when present are independently hydrogen, lower alkyl, or aralkyl, $R^{14}$ and $R^{16}$ when present are independently selected from the group consisting of hydrogen, alkyl, aralkyl, cycloalkyl, cycloalkylalkyl, heterocyclyl and heterocyclylalkyl provided that when $R^3$ is hydrogen, alkyl or aryl, $R^{12}$ is not hydrogen, and provided that when $R^1$ is phenyl, $R^3$ is benzyloxycarbonylamino, and $R^{12}$ is hydrogen, $R^2$ is not 2-methoxybenzyl, and $R^1$, $R^2$, $R^3$, $R^{12}$, $R^{13}$, $R^{14}$, $R^{15}$, $R^{16}$, $R^{21}$, $R^{22}$, $R^{23}$ and $R^{24}$ when present may independently be either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, hydroxyalkyl, aryloxy, hydroxyaryl, alkoxyaryl, halo, haloalkyl, haloaryl, haloalkoxy, amino, alkylamino, dialkylamino, arylamino, diarylamino, —NHCO(alkyl), —NHCO(aryl), —NHCO(aralkyl), —NHCO(haloalkyl), —$NHSO_2$(alkyl), —$NHSO_2$(aryl), —$NHSO_2$(aralkyl), alkoxycarbonyl, alkoxycarbonylalkyl, —OCO(alkylamino), —OCO(dialkylamino).

In other embodiments, the compounds are given by the general Formula (IV):

$$R^1\text{-}M^1\text{-}N(R^2)\text{-}M^2\text{-}M^3\text{-}M^4\text{-}M^5\text{-}M^6\text{-}R^3 \quad \text{(IV)}$$

wherein:

$R^1$ is alkyl, aryl or aralkyl, $R^2$ is aralkyl or alkyl, provided that when $R^1$ is alkyl, $R^2$ is aralkyl, $M^1$ is CO or $SO_2$, provided that when $M^1$ is $SO_2$ and $R^1$ is phenyl, 4-methylphenyl or 2,4,6-trimethylphenyl, $R^2$ is not alkyl, 2-phenethyl, benzyl, or 2-methoxy-2-oxoethyl, and provided that when $M^1$ is CO and $R^1$ is 2-furyl, 4-pyridyl, or 3,5-dinitrophenyl, $R^2$ is not alkyl, benzyl or 2-(1H-indol-2-yl)ethyl, $M^2$ is absent or $CH_2$, $M^3$ and $M^4$ are absent, $M^5$ is $(CR^{11}R^{12})$, $R^{11}$ is hydrogen, $R^{12}$ is selected from the group consisting of hydrogen, $NR^{21}CONR^{22}R^{23}$, $NR^{21}COR^{24}$, $NR^{21}SO_2R^{24}$, $NR^{21}COOR^{24}$, $CONR^{22}R^{23}$, $COOR^{24}$, $O(CH_2CH_2O)_sR^{24}$, hydroxyalkyl and alkoxyalkyl, s is an integer of 1 to 6, $M^6$ is $(CH_2)_q$ q is an integer of 0 to 6, $R^3$ is selected from the group consisting of $NR^{15}COOR^{16}$, $NR^{15}COR^{16}$, $NR^{15}CONR^{13}R^{14}$, and $NR^{15}SO_2R^{16}$, and $R^{13}$, $R^{21}$ and $R^{22}$, when present, are independently selected from the group consisting of hydrogen and lower alkyl, and $R^{14}$, $R^{15}$, $R^{16}$, $R^{23}$ and $R^{24}$, each of which when present, is independently selected from the group consisting of hydrogen, alkyl, aryl, cycloalkyl, cycloalkylalkyl, heterocyclyl, heterocyclylalkyl and aralkyl, and $R^1$, $R^2$, $R^3$, $R^{12}$, $R^{14}$, $R^{15}$, $R^{16}$, $R^{23}$ and $R^{24}$ when present may independently be either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(aralkyl), —NHCO(haloalkyl), —$NHSO_2$(alkyl), —$NHSO_2$(aryl), —$NHSO_2$(aralkyl), alkoxycarbonyl, alkoxycarbonylalkyl, —OCO(alkylamino) and —OCO(dialkylamino).

In some embodiments, the compounds are given by the general Formula (V):

$$R^1\text{-}M^1\text{-}N(R^2)\text{-}M^2\text{-}M^3\text{-}M^4\text{-}M^5\text{-}M^6\text{-}R^3 \quad \text{(V)}$$

wherein:

$R^1$ is aryl or aralkyl, $R^2$ is alkyl or aralkyl, $M^1$ is $CH_2$, $M^2$ is CO, $M^3$ is absent or is O or $CH_2$, $M^4$ is absent or is $CH_2$, $M^5$ is absent or is O or $(CR^{11}R^{12})$, $R^{11}$ is hydrogen, $R^{12}$ is selected from the group consisting of hydrogen, $NR^{21}CONR^{22}R^{23}$, $NR^{21}COR^{24}$, $NR^{21}SO_2R^{24}$ and $NR^{21}COOR^{24}$, $M^6$ is selected from the group consisting of $(CH_2)_q$, $(CH_2)_q$—CH═CH—$(CH_2)_r$, $(CH_2)_q$-arylene-$(CH_2)_r$ and $(CH_2CH_2O)_q$, q and r are independently integers from 0 to 6, $R^3$ is $CONR^{13}R^{14}$, $R^{21}$ and $R^{22}$ each of which, when present is independently selected from the group of hydrogen and lower alkyl, $R^{13}$, $R^{14}$, $R^{23}$ and $R^{24}$, each of which, when present is independently selected from the group consisting of hydrogen, alkyl, aryl, cycloalkyl, cycloalkylalkyl, heterocyclyl, heterocyclylalkyl and aralkyl, and $R^1$, $R^2$, $R^{13}$, $R^{14}$, $R^{23}$ and $R^{24}$ when present may be either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(aralkyl), —NHCO(haloalkyl), —$NHSO_2$(alkyl), —$NHSO_2$(aryl), —$NHSO_2$(aralkyl), alkoxycarbonyl, alkoxycarbonylalkyl, —OCO(alkylamino), and —OCO(dialkylamino).

In other embodiments, the compounds are given by the general Formula (VI):

$$R^1\text{-}M^1\text{-}N(R^2)\text{-}M^2\text{-}M^3\text{-}M^4\text{-}M^5\text{-}M^6\text{-}R^3 \quad \text{(VI)}$$

wherein:

$R^1$ is aryl or aralkyl, $R^2$ is alkyl or aralkyl, $M^1$ is $CH_2$, $M^2$ is $SO_2$ or CO, $M^3$ is absent or is $CH_2$, $M^4$ is absent or is $CH_2$, $M^5$ is absent or is $(CR^{11}R^{12})$, $R^{11}$, when present, is hydrogen, $R^{12}$, when present, is selected from the group consisting of hydrogen, alkyl, $NR^{21}CONR^{22}R^{23}$, $NR^{21}COR^{24}$, $NR^{21}SO_2R^{24}$ and $NR^{21}COOR^{24}$, $M^6$ is $(CH_2)_q$, or $NR^{34}(CH_2)_q$, q is an integer from 0 to 6, $R^3$ is selected from the group consisting of $CONR^{13}R^{14}$, $SO_2NR^{13}R^{14}$, $NR^{15}COOR^{16}$, $NR^{15}COR^{16}$, $NR^{15}CONR^{13}R^{14}$, and $NR^{15}SO_2R^{16}$, $R^{15}$, $R^{16}$, $R^{21}$ and $R^{22}$, each of which when present, is independently selected from the group of hydrogen, lower alkyl, and aralkyl, $R^{13}$, $R^{14}$, $R^{23}$ and $R^{24}$, each of which, when present is independently selected from the group consisting of hydrogen, alkyl, aryl, cycloalkyl, cycloalkylalkyl, heterocyclyl, heterocyclylalkyl and aralkyl, $R^{34}$, when present, is selected form the group consisting of alkyl, aralkyl, $COR^{35}$, and $SO_2R^{35}$, $R^{35}$, when present, is selected form the group consisting of alkyl, aryl, and aralkyl, and $R^1$, $R^2$, $R^{13}$, $R^{14}$, $R^{15}$, $R^{16}$, $R^{23}$, $R^{24}$, $R^{34}$ and $R^{35}$, when present, may be either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(aralkyl), —NHCO(haloalkyl), —$NHSO_2$(alkyl), —$NHSO_2$(aryl), —$NHSO_2$(aralkyl), alkoxycarbonyl, alkoxycarbonylalkyl, —OCO(alkylamino), and —OCO(dialkylamino), with the proviso that when $M^2$ is CO, then $M^6$ is $NR^{34}(CH_2)_q$, and q is not 0.

In other embodiments, the compounds are given by the general Formula (VII):

$$R^1\text{-}M^1\text{-}N(R^2)\text{-}M^2\text{-}M^3\text{-}M^4\text{-}M^5\text{-}M^6\text{-}R^3 \quad \text{(VII)}$$

wherein:

$R^1$ and $R^2$ are independently selected from the group consisting of alkyl, aryl, aralkyl, cycloalkyl, cycloalkylalkyl, haloalkyl, heterocylcyl and heterocyclylalkyl, one of $M^1$ and $M^2$ is CO or $SO_2$ and the other is $(CR^4R^5)_l$, provided that when $M^2$ is CO, $M^3$ is O, S, $NR^6$ or $(CR^7R^8)_m$, and provided that when $M^2$ is $SO_2$ or $(CR^4R^5)_l$, $M^3$ is $(CR^7R^8)_m$, $M^4$ is absent or $(CR^9R^{10})_n$, $M^5$ is absent or is O or $(CR^{11}R^{12})_p$, $M^6$ is absent or is selected from the group consisting of $(CH_2)_q$, $(CH_2)_q$—CH═CH—$(CH_2)_r$, $(CH_2)_q$-arylene-$(CH_2)_r$, $(CH_2CH_2O)_q$, and $NR^{34}(CH_2)_q$, and $R^3$ is selected from the group consisting of hydrogen, alkyl, aryl, aralkyl, hydroxyl (OH), heterocyclyl, hydroxyalkyl, guanadino $OR^{16}$, $CONR^{13}R^{14}$, $NR^{15}COOR^{16}$, $NR^{15}COR^{16}$, $NR^{15}CONR^{13}R^{14}$, $NR^{15}SO_2R^{16}$, $OCOR^{16}$, $COOR^{16}$, and $SR^{16}$.

$R^{34}$, when present, is selected form the group consisting of alkyl, aralkyl, $COR^{35}$, and $SO_2R^{35}$, $R^{35}$, when present, is selected form the group consisting of alkyl, aryl, and aralkyl, and $R^{12}$, when present, is selected from the group consisting of hydrogen, alkyl, OH, $N_3$, CN, $NR^{21}CONR^{22}R^{23}$, $NR^{21}COR^{24}$, $NR^{21}COOR^{24}$, $NR^{21}SO_2R^{24}$, $CONR^{22}R^{23}$, $COOR^{24}$, $OCOR^{24}$, $OR^{24}$, $SCOR^{24}$, $SR^{24}$, azido, CN, and $O(CH_2CH_2O)R^{24}$, $R^4$, $R^5$, $R^6$, $R^7$, $R^8$, $R^9$, $R^{10}$, $R^{11}$, $R^{15}$, and $R^{21}$, each of which when present, is independently selected from the group consisting of hydrogen, lower alkyl and aralkyl, $R^{13}$, $R^{14}$, $R^{16}$, $R^{22}$, $R^{23}$ and $R^{24}$, each of which when present, is independently selected from the group consisting of alkyl, aryl, aralkyl, cycloalkyl, cycloalkylalkyl, haloalkyl, heterocyclyl, heterocyclylalkyl, alkoxycarbonyl, alkoxycarbonylalkyl, l, m, n and p are independently integers from 0 to 1, q, r and s are independently integers from 0 to 6, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{21}$, $R^{22}$, $R^{23}$, $R^{24}$, $R^{34}$ and $R^{35}$, each of which when present, is independently either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxyl, alkoxy, haloalkoxy, azido, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(haloalkyl), —$NHSO_2$(alkyl), —$NHSO_2$(aryl), alkoxycarbonyl, alkoxycarbonylalkyl, —OCO(alkylamino), —OCO(dialkylamino).

In other embodiments, the compounds are given by the general Formula (VIII):

$$R^1\text{-}M^1\text{-}N(R^2)\text{-}M^2\text{-}M^3\text{-}M^4\text{-}M^5\text{-}M^6\text{-}R^3 \quad \text{(VIII)}$$

wherein:

$R^1$ is selected from the group consisting of alkyl, aryl, and aralkyl, $R^2$ is selected from the group consisting of alkyl, aryl, aralkyl, alkoxyalkyl and hydroxyalkyl, $M^1$ is $CH_2$, $M^2$ is $SO_2$;

$M^3$, $M^4$, $M^5$, and $M^6$ independently are absent or are $CH_2$;

$R^3$ is selected from the group consisting of alkyl, aryl, aralkyl, aryloxyalkyl, alkoxyalkyl, cycloalkyl and cycloalkylalkyl;

$R^1$, $R^2$ and $R^3$ are independently either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxyl, alkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(haloalkyl), —$NHSO_2$(alkyl), —$NHSO_2$(aryl), alkoxycarbonyl, alkoxycarbonylalkyl, —OCO(alkylamino), —OCO(dialkylamino).

In other embodiments, the compounds are defined by:

$R^1$ is aryl, $R^2$ is aralkyl, $M^1$ is $CH_2$, $M^2$ is CO, $M^3$ is absent, $M^4$ is absent, $M^5$ is absent, $M^6$ is $(CH_2)_q$, q is an integer from 1 to 6, $R^3$ is $CONR^{13}R^{14}$, and $R^{13}$ and $R^{14}$ are independently aralkyl.

In other embodiments, $R^1M^1$, $R^2$, $R^{13}$, and $R^{14}$ are independently selected from the group consisting of 2-thienylmethyl, 3-methoxybenzyl, 4-methoxybenzyl, 2-(2-thienyl)ethyl, pyridin-4-ylmethyl, pyridin-3-ylmethyl, and 4-dimethylaminobenzyl.

In other embodiments, the compounds are defined by:

$R^1$ is aryl, $R^2$ is aralkyl, $M^1$ is $CH_2$, $M^2$ is CO, $M^3$ is O, $M^4$ is absent, $M^5$ is absent, $M^6$ is $(CH_2CH_2O)_q$, q is an integer from 1 to 6, $R^3$ is $CONR^{13}R^{14}$, and $R^{13}$ and $R^{14}$ are independently aralkyl.

In other embodiments, $R^1M^1$, $R^2$, $R^{13}$, and $R^{14}$ are independently selected from the group consisting of 2-thienylmethyl, 3-methoxybenzyl, 4-methoxybenzyl, 2-(2-thienyl)ethyl, pyridin-4-ylmethyl, and pyridin-3-ylmethyl.

In other embodiments, the compounds are defined by:

$R^1$ is aryl, $R^2$ is aralkyl, $M^1$ is $CH_2$, $M^2$ is CO, $M^3$ is O, $M^4$ is $CH_2$, $M^5$ is $CR^{11}R^{12}$, $R^{11}$ is hydrogen and $R^{12}$ is alkyl, $M^6$ is absent, $R^3$ is $NR^{15}CONR^{13}R^{14}$, $R^{13}$ and $R^{15}$ are hydrogen, and $R^{14}$ is heterocyclylalkyl.

In other embodiments, $R^1M^1$, $R^2$, $R^{13}$, and $R^{14}$ are independently selected from the group consisting of 2-thienylmethyl, 3-methoxybenzyl, 4-methoxybenzyl, 2-(2-thienyl)ethyl, pyridin-4-ylmethyl, pyridin-3-ylmethyl, and 4-dimethylaminobenzyl.

In other embodiments, the one or more compounds are defined by:

$R^1$ is aryl, $R^2$ is aralkyl, $M^1$ is $CH_2$, $M^2$ is CO or $SO_2$, $M^3$ is $CH_2$, $M^4$ is $CH_2$, $M^5$ is absent or $CH_2$, $M^6$ is $NR^{34}(CH_2)_q$, q is an integer from 2 to 6, $R^{34}$ is alkyl, $R^3$ is $CONR^{13}R^{14}$, and $R^{13}$ and $R^{14}$ are independently aralkyl.

In other embodiments, $R^1M^1$, $R^2$, $R^{13}$, and $R^{14}$ are independently selected from the group consisting of 2-thienylmethyl, 3-methoxybenzyl, 4-methoxybenzyl, 2-(2-thienyl)ethyl, pyridin-4-ylmethyl, pyridin-3-ylmethyl, and 4-dimethylaminobenzyl.

In other embodiments, the one or more compounds are defined by:

$R^1$ is aryl, $R^2$ is aralkyl, $M^1$ is $CH_2$, $M^2$ is CO or $SO_2$, $M^3$ is absent, O, or $CH_2$, $M^4$ is absent, $M^5$ is absent, $M^6$ is $(CH_2)_q$—CH═CH—$(CH_2)_r$, q and r are integer having a value between 1 and 6, and $R^3$ is $CONR^{13}R^{14}$, and $R^{13}$ and $R^{14}$ are independently aralkyl.

In other embodiments, $R^1M^1$, $R^2$, $R^{13}$, and $R^{14}$ are independently selected from the group consisting of 2-thienylmethyl, 3-methoxybenzyl, 4-methoxybenzyl, 2-(2-thienyl)ethyl, pyridin-4-ylmethyl, pyridin-3-ylmethyl, and 4-dimethylaminobenzyl.

In other embodiments, the one or more compounds are defined by:

$R^1$ is aryl, $R^2$ is aralkyl, $M^1$ is $CH_2$, $M^2$ is CO or $SO_2$, $M^3$ is absent, O, or $CH_2$, $M^4$ is absent, $M^5$ is absent, $M^6$ is $(CH_2)_q$-arylene-$(CH_2)_r$, q and r are integer having a value between 1 and 6, and $R^3$ is $CONR^{13}R^{14}$, and $R^{13}$ and $R^{14}$ are independently aralkyl.

In other embodiments, $R^1M^1$, $R^2$, $R^{13}$, and $R^{14}$ are independently selected from the group consisting of 2-thienylmethyl, 3-methoxybenzyl, 4-methoxybenzyl, 2-(2-thienyl)ethyl, pyridin-4-ylmethyl, pyridin-3-ylmethyl, and 4-dimethylaminobenzyl.

In other embodiments, the pharmaceutical compositions further include a pharmaceutically acceptable carrier for the one or more compounds. In other embodiments, the compounds may be used in combination with one or more anti-cancer agents.

Embodiments of this disclosure broadly relate to methods for treating cancers, wherein the methods include administering to a human, a mammal, or an animal a pharmaceutical composition including one or more one or more N,N-disubstituted amide compounds, N,N-disubstituted carbamate compounds, N,N-disubstituted urea compounds, and/or N,N-disubstituted sulfonamide compounds etenerally or parenterally, wherein parenterally may include direct injection of the composition into a target tissue site.

List of Specific Compounds

In some embodiments, the compounds are selected from the group consisting of methyl(6S,10S)-10-(1,3-benzodioxol-5-yl)-6-butyl-3,8-dioxo-1-(2-thieny-1)-2-(2-thienylmethyl)-4-oxa-2,7,9-triazadodecan-12-oate; methyl(6S,10R)-10-(1,3-benzodioxol-5-yl)-6-butyl-3,8-dioxo-1-(2-thienyl)-2-(2-thienylmethyl)-4-oxa-2,7,9-triazadodecan-12-oate; methyl(6S,10S)-10-(1,3-benzodioxol-5-yl)-6-butyl-7-methyl-3,8-dioxo-1-(2-thienyl)-2-(2-thienylmethyl)-4-oxa-2,7,9-triazadodecan-12-oate; methyl(6S,10S)-10-(1,3-benzodioxol-5-yl)-6-butyl-9-methyl-3,8-dioxo-1-(2-thienyl)-2-(2-thienyl)-2-(2-thienylmethyl)-4-oxa-2,7,9-triazadodecan-12-oate; ethyl(6S,10R)-10-(1,3-benzodioxol-5-yl)-6-butyl-7-methyl-3,8-dioxo-1-(-2-thienyl)-2-(2-thienylmethyl)-4-oxa-2,7,9-triazadodecan-12-oate; methyl(10S)-10-(1,3-benzodioxol-5-yl)-3,8-dioxo-1-(2-thienyl)-2-(2-thienylmethyl)-4-oxa-2,7,9-triazadodecan-12-oate; methyl 3,8-dioxo-1-(2-thienyl)-2-(2-thienylmethyl)-4-oxa-2,7,9-triazadodecan-12-oate; methyl(6S,10S)-10-(1,3-benzodioxol-5-yl)-6-butyl-2-methyl-3,8-dioxo-1-(2-thienyl)-4-oxa-2,7,9-triazadodecan-12-oate; methyl(6S)-6-butyl-3,8-dioxo-1-(2-thienyl)-2-(2-thienylmethyl)-4-oxa-2,7,-9-triazadodecan-12-oate; (2S)-2-{[(1,3-benzodioxol-5-ylmethyl)carbamoyl]amino}hexylbis(2-thienylmethyl) carbamate; methyl(6S,10S)-6-butyl-3,8-dioxo-10-phenyl-1-(2-thienyl)-2-(2-thienylmethyl)-4-oxa-2,7,9-triazadodecan-12-oate; (2S)-2-({[(1S)-1-(1,3-benzodioxol-5-yl)-3-hydroxypropyl]carbamoyl}amino)hexyl bis(2-thienylmethyl)carbamate; (2S)-2-[(benzylcarbamoyl)amino]hexyl bis(2-thienylmethyl)carbamate; (2S)-2-[(morpholin-4-ylcarbonyl)amino]hexyl bis(2-thienylmethyl)carbamate; (2S)-2-{[(3-methoxypropyl)carbamoyl]amino}hexyl bis(2-thienylmethyl)carbamate; (2S)-2-{[(2-methoxyethyl)carbamoyl]amino}hexyl bis(2-thienylmethyl)carbamate; tert-butyl[(2S)-1-{[bis(2-thienylmethyl)carbamoyl]oxy}hexan-2-yl]carbamate; (2S)-2-[(tert-butylcarbamoyl)amino]hexyl bis(2-thienylmethyl) carbamate; (2S)-2-[(isopropylcarbamoyl)amino]hexylbis(2-thienylmethyl)carbamate; (2S)-2-[(methylcarbamoyl)amino]hexylbis(2-thienylmethyl)carbamate; tert-butyl [(2R)-1-{[bis(2-thienylmethyl)carbamoyl]oxy}hexan-2-yl] carbamate; benzyl{(5S)-6-{[bis(2-thienylmethyl)carbamoyl]oxy}-5-[(tert-butoxycarbonyl)amino]hexyl}carbamate; methyl(9S,13S)-13-(1,3-benzodioxol-5-yl)-9-({[bis(2-thienylmethyl)carbamoyl]oxy}methyl)-3,11- dioxo-1-phenyl-2-oxa-4,10,12-triazapentadecan-15-oate; (2S)-2-acetamidohexylbis(2-thienylmethyl)carbamate; methyl(3R)-3-(1,3-benzodioxol-5-yl)-3-{[(2S)-2-{[bis(2-thienylmethyl)carbamoyl]amino}hexanoyl]amino}propanoate; methyl(3R)-3-(1,3-benzodioxol-5-yl)-3-{[(2R)-2-{[bis(2-thienylmethyl)carbamoyl]amino}hexanoyl]amino}propanoate; methyl(3S)-3-(1,3-benzodioxol-5-yl)-3-{[(2R)-2-{[bis(2-thienylmethyl)carbamoyl]amino}hexanoyl]amino}propanoate; methyl(6R,10S)-10-(1,3-benzodioxol-5-yl)-6-butyl-3,8-dioxo-1-(2-thienyl)-2-(2-thienylmethyl)-4-oxa-2,7,9-triazadodecan-12-oate; methyl(6R,10R)-10-(1,3-benzodioxol-5-yl)-6-butyl-3,8-dioxo-1-(2-thienyl)-2-(2-thienylmethyl)-4-oxa-2,7,9-triazadodecan-12-oate; methyl(2S)-2-{[bis(2-thienylmethyl)-carbamoyl]amino}hexanoate; methyl(2R)-2-{[bis(2-thienylmethyl)carbamoyl]amino}hexanoate; 3-[(2S)-1-hydroxyhexan-2-yl]-1,1-bis(2-thienylmethyl)urea; 3-[(2R)-1-hydroxyhexan-2-yl]-1,1-bis(2-thienylmethyl)urea; methyl(2S)-6-{[(benzyloxy)carbonyl]amino}-2-{[bis(2-thienylmethyl)carbamoyl]amino}hexanoate; methyl{[bis(2-thienylmethyl)carbamoyl](methyl)amino}acetate; methyl{[bis(2-thienylmethyl)carbamoyl]amino}acetate; methyl{[bis(2-thienylmethyl)carbamoyl](butyl)amino}acetate; 3-(3-hydroxypropyl)-1,1-bis(2-thienylmethyl)urea; methyl(2R)-{[bis(2-thienylmethyl)carbamoyl]amino}(phenyl)acetate; tert-butyl{[bis(2-thienylmethyl)carbamoyl]amino}acetate; tert-butyl{[bis(2-thienylmethyl) carbamoyl](butyl)amino}acetate; benzyl {(5S)-6-{[bis(4-methoxybenzyl) carbamoyl]oxy}-5-[(tert-butoxycarbonyl)amino]hexyl}carbamate; tert-butyl[(2S)-1-{[bis(4-methoxybenzyl)carbamoyl]oxy}hexan-2-yl]carbamate; methyl(6S,10S)-10-(1,3-benzodioxol-5-yl)-6-butyl-2-(4-methoxybenzyl)-1-(4-methoxyphenyl)-3,8-dioxo-4-oxa-2,7,9-triazadodecan-12-oate; (2S)-2-({[(1S)-1-(1,3-benzodioxol-5-yl)-3-hydroxypropyl]carbamoyl}amino)hexyl bis(4-methoxybenzyl)carbamate; (2S)-2-[(tert-butoxycarbonyl)amino]hexyldibenzylcarbamate; methyl(6S,10S)-10-(1,3-benzodioxol-5-yl)-2-benzyl-6-butyl-3,8-dioxo-1-phenyl-4-oxa-2,7,9-triazadodecan-12-oate; tert-butyl[(2S)-1-{[bis(4-methylbenzyl)carbamoyl]oxy}hexan-2-yl]carbamate; methyl(6S,10S)-10-(1,3-benzodioxol-5-yl)-6-butyl-2-(4-methylbenzyl)-1-(4-methylphenyl)-3,8-dioxo-4-oxa-2,7,9-triazadodecan-12-oate; tert-butyl[(2S)-1-{[bis(4-chlorobenzyl)carbamoyl]oxy}hexan-2-yl]carbamate; methyl(6S,10S)-10-(1,3-benzodioxol-5-yl)-6-butyl-2-(4-chlorobenzyl)-1-(4-chlorophenyl)-3,8-dioxo-4-oxa-2,7,9-triazadodecan-12-oate; (2S)-2-[(tert-butoxycarbonyl)amino]hexyl (4-bromobenzyl)(2-thienylmethyl)carbamate; methyl(6S,10S)-10-(1,3-benzodioxol-5-yl)-2-(4-bromobenzyl)-6-butyl-3,8-dioxo-1-(2-thienyl)-4-oxa-2,7,9-triazadodecan-12-oate; methyl(6S,1 S)-2-(4-azidoobenzyl)-10-(1,3-benzodioxol-5-yl)-6-butyl-3,8-dioxo-1-(2-thienyl)-4-oxa-2,7,9-triazadodecan-12-oate; (2S)-2-[(tert-butoxycarbonyl)amino]hexylphenyl(2-thienylmethyl)carbamate; methyl(6S,10S)-10-(1,3-benzodioxol-5-yl)-6-butyl-3,8-dioxo-2-phenyl-1-(2-thienyl)-4-oxa-2,7,9-triazadodecan-12-oate; tert-butyl[(2S)-1-{[bis(3-thienylmethyl) carbamoyl]oxy}hexan-2-yl]carbamate; methyl(6S,10S)-10-(1,3-benzodioxol-5-yl)-6-butyl-3,8-dioxo-1-(3-thienyl)-2-(3-thienylmethyl)-4-oxa-2,7,9-triazadodecan-12-oate; benzyl[(5S)-5-[(tert-butoxycarbonyl)amino]-6-{[butyl(2-thienylmethyl)carbamoyl]oxy}hexyl]carbamate; (2S)-2-[(tert-butoxycarbonyl)amino]hexyl butyl(2-thienylmethyl)carbamate; methyl(3S,7S)-3-(1,3-benzodioxol-5-yl)-7-butyl-5,10-dioxo-11-(2-thienylmethyl)-9-oxa-4,6,11-triazapentadecan-1-oate; benzyl[(5S)-5-[(tert-butoxycarbonyl)amino]-6-{[(2-methoxyethyl)(2-thienylmethyl)carbamoyl]oxy}hexyl]carbamate; (2S)-2-[(tert-butoxycarbonyl)amino]hexyl(2-methoxyethyl)(2-thienylmethyl)carbamate; methyl(9S,13S)-13-(1,3-benzodioxol-5-yl)-9-butyl-6,11-dioxo-5-(-2-thienylmethyl)-2,7-dioxa-5,10,12-triazapentadecan-15-oate; (2S)-2-[({3-[(methylsulfonyl)amino]benzyl}carbamoyl)amino]hexyl(2-methoxyl)(2-thienyl methyl)carbamate; (2S)-2-{[(4-bromobenzyl)carbamoyl]amino}hexyl bis(2-thienylmethyl)carbamate; (2S)-2-{[(4-azidobenzyl)carbamoyl]amino}hexylbis (2-thienylmethyl)carbamate; tert-butyl [(2S)-1-{[bis(2-thienylmethyl) carbamoyl]thio}hexan-2-yl]carbamate; methyl(6S,10S)-10-(1,3-benzodioxol-5-yl)-6-butyl-3,8-dioxo-1-(2-thienyl)-2-(2-thienylmethyl)-4-thia-2,7,9-triazadodecan-12-oate; and mixtures or combinations thereof.

In some embodiments, the compounds are selected from the group consisting of (2R)-2-({[(1 S)-1-(1,3-benzodioxol-5-yl)-3-hydroxypropyl]carbamoyl}amino)-N,N-bis (2-thienylmethyl)hexanamide; methyl(3S)-3-(1,3-benzodioxol-5-yl)-3-[({3-[bis(2-thienylmethyl)amino]-3-oxopropyl}carbamoyl)amino]propanoate; (2S)-2-[(tert-butylcarbamoyl)amino]-N,N-bis(2-thienylmethyl)hexanamide; tert-butyl{(2S)-1-[bis(2-thienylmethyl)amino]-1-oxohexan-2-yl}carbamate; benzyl{(5S)-6-[bis(2-thienylmethyl)amino]-5-[(tert-butoxycarbonyl)(methyl)amino]-6-oxohexyl}carbamate; benzyl{(5S)-6-[bis(2-thienylmethyl)amino]-5-[(tert-butoxycarbonyl)amino]-6-oxohexyl}carbamate; benzyl{(5R)-6-[bis(2-thienylmethyl)amino]-5-[(tert-butoxycarbonyl)amino]-6-oxohexyl}carbamate; tert-butyl{(2R)-1-[bis(2-thienylmethyl) amino]-1-oxohexan-2-yl}carbamate; (2S)-2-acetamido-N,N-bis(2-thienylmethyl)hexanamide; benzyl {(5S)-5-acetamido-6-[bis(2-thienylmethyl)amino]-6-oxohexyl}carbamate; (2R)-2-acetamido-N,N-bis (2-thienylmethyl)hexanamide; benzyl{(5S)-5-(benzoylamino)-6-[bis (2-thienylmethyl) amino]-6-oxohexyl}carbamate; (2S)-2-[(phenylsulfonyl)amino]-N,N-bis(2-thienylmethyl)hexanamide; (2S)-2-[methyl(phenylsulfonyl)amino]-N,N-bis(2-thienylmethyl)hexanamide; 2-[(phenylsulfonyl)amino]-N,N-bis(2-thienylmethyl)acetamide; 2-[methyl(phenylsulfonyl) amino]-N,N-bis(2-thienylmethyl)acetamide; (2S)-2-[(methylsulfonyl)amino]-N,N-bis (2-thienylmethyl)hexanamide; (2S)-2-({[3-(4-methoxyphenoxy)propyl]sulfonyl}amino)-N,N-bis(2-thienylmethyl)hexanamide; benzyl{(5S)-6-[bis(2-thienylmethyl)amino]-6-oxo-5-[(2-thienylsulfonyl)amino]hexyl}carbamate; benzyl{(5S)-5-[(tert-butoxycarbonyl)amino]-6-[(3-methoxybenzyl)(2-thienylmethyl)amino]-6-oxohexyl}carbamate; benzyl{(5S)-6-[bis(3-methoxybenzyl)amino]-5-[(tert-butoxycarbonyl)amino]-6-oxohexyl}carbamate; benzyl{(5R)-5-[(tert-butoxycarbonyl)amino]-6-[(3-methoxybenzyl)(2-thienylmethyl)amino]-6-oxohexyl}carbamate; benzyl{(5R)-6-[bis(3-methoxybenzyl)amino]-5-[(tert-butoxycarbonyl)amino]-6-oxohexyl}carbamate; benzyl[(5S)-5-[(tert-butoxycarbonyl)amino]-6-oxo-6-{[2-(2-thienyl)ethyl](-2-thienylmethyl)amino}hexyl]carbamate; benzyl[(5R)-5-[(tert-butoxycarbonyl)amino]-6-oxo-6-{[2-(2-thienyl)ethyl](-2-thienylmethyl)amino}hexyl]carbamate; benzyl[(5S)-5-[(tert-butoxycarbonyl)amino]-6-(dibenzylamino)-6-oxohexyl]carbamate; benzyl{(5S)-5-[(tert-butoxycarbonyl)amino]-6-[(4-nitrobenzyl)(2-thienylmethyl)amino]-6-oxohexyl}carbamate; benzyl{(5R)-5-[(tert-butoxycarbonyl)amino]-6-[(4-nitrobenzyl)(2-thienylmethyl)amino]-6-oxohexyl}carbamate; tert-butyl[(2R)-1-[(4-aminobenzyl)(2-thienylmethyl)amino]-6-{[(benzyloxy)-carbonyl]amino}-1- oxohexan-2-yl]carbamate; tert-butyl[(2S)-1-[(4-aminobenzyl)(2-thienylmethyl)amino]-6-{[(benzyloxy)-carbonyl]amino}-1-oxohexan-2-yl]carbamate; benzyl{(5S)-5-[(tert-butoxycarbonyl)amino]-6-[methyl(2-thienylmethyl) amino]-6-oxohexyl}carbamate; benzyl{(5S)-5-[(tert-butoxycarbonyl) amino]-6-[butyl(2-thienylmethyl)amino]-6-oxohexyl}carbamate; benzyl{(5S)-6-[bis(4-methoxybenzyl)amino]-5-[(tert-butoxycarbonyl)amino]-6-oxohexyl}carbamate; benzyl{(5S)-5-[(tert-butoxycarbonyl) amino]-6-oxo-6-[(pyridin-4-ylmethyl)(-2-thienylmethyl) amino]hexyl}carbamate; benzyl{(5S)-5-[(tert-butoxycarbonyl)amino]-6-oxo-6-[(pyridin-3-ylmethyl)(-2-thienylmethyl)amino]hexyl}carbamate; benzyl{(5S)-6-[bis(pyridin-4-ylmethyl)amino]-5-[(tert-butoxycarbonyl)amino]-6-oxohexyl}carbamate; tert-butyl{(2S)-1-[bis(2-thienylmethyl)amino]-1-oxo-6-[(2-thienylsulfonyl)amino] hexan-2-yl}carbamate; tert-butyl{(2S)-6-acetamido-1-[bis (2-thienylmethyl)amino]-1-oxohexan-2-yl}carbamate; tert-butyl{(2S)-1-[bis(2-thienylmethyl)amino]-1-oxo-6-[(trifluoroacetyl)amino]hexan-2-yl}carbamate; tert-butyl {(2S)-1-[bis(2-thienylmethyl)amino]-6-[(methylsulfonyl) amino]-1-oxohexan-2-yl}carbamate; tert-butyl{(2S)-1-[bis (2-thienylmethyl)amino]-1-oxo-6-[(2-thienylcarbonyl) amino]hexan-2-yl}carbamate; tert-butyl{(2S)-1-[bis(2-thienylmethyl) amino]-1-oxo-6-[(phenylsulfonyl)amino]hexan-2-yl}carbamate; tert-butyl{(2S)-1-[bis(2-thienylmethyl) amino]-1-oxo-6-[(pyridin-3-ylcarbonyl)amino]hexan-2-yl}carbamate; tert-butyl{(2S)-1-[bis(2-thienylmethyl) amino]-1-oxo-6-[(2-thienylacetyl)amino]hexan-2-yl}carbamate; tert-butyl{(2S)-1-[bis(2-thienylmethyl) amino]-6-hydroxy-1-oxohexan-2-yl}carbamate; tert-butyl [(2S)-1-[bis(2-thienylmethyl) amino]-1-oxo-6-{[(trifluoromethyl)sulfonyl]amino}hexan-2-yl]carbamate; tert-butyl{(2S)-6-[(benzylsulfonyl)amino]-1-[bis(2-thienylmethyl)amino]-1-oxohexan-2-yl}carbamate; tert-butyl {(2S)-6-[benzyl(trifluoroacetyl) amino]-1-[bis(2-thienylmethyl)amino]-1-oxohexan-2-yl}carbamate; tert-butyl[(1R)-2-[bis(2-thienylmethyl)amino]-1-(4-hydroxyphenyl)-2-oxoethyl]carbamate; methyl(4S)-5-[bis(2-thienylmethyl) amino]-4-[(tert-butoxycarbonyl)amino]-5-oxopentanoate; benzyl{(3S)-4-[bis(thiophen-2-ylmethyl)amino]-3-[(tert-butoxycarbonyl)amino]-4-oxobutyl}carbamate; benzyl {(4S)-5-[bis(2-thienylmethyl)amino]-4-[(tert-butoxycarbonyl)amino]-5-oxopentyl}carbamate; tert-butyl{2-[bis(2-thienylmethyl)amino]-2-oxoethyl}carbamate; tert-butyl{2-[bis(2-thienylmethyl)amino]-2-oxoethyl}methylcarbamate; N,N-bis(2-thienylmethyl)-6-[(2-thienylsulfonyl)amino] hexanamide; N-{6-[bis(2-thienylmethyl)amino]-6-oxohexyl}thiophene-2-carboxamide; N-{6-[bis(2-thienylmethyl)amino]-6-oxohexyl}-N-(2-thienylmethyl)thiophene-2-carboxamide; N-benzyl-N-{6-[bis(2-thienylmethyl) amino]-6-oxohexyl}thiophene-2-carboxamide; 6-[benzyl(2-thienylsulfonyl)amino]-N,N-bis(2-thienylmethyl) hexanamide; 6-[methyl(2-thienylsulfonyl)amino]-N,N-bis (2-thienylmethyl)hexanamide; 6-[(benzylsulfonyl)amino]-N,N-bis(2-thienylmethyl)hexanamide; 6-[(2-thienylacetyl) amino]-N,N-bis(2-thienylmethyl)hexanamide; N-{6-[bis(2-thienylmethyl)amino]-6-oxohexyl}-N-(3-methoxybenzyl) thiophene-2-carboxamide; 6-[(3-methoxybenzyl)(2-thienylsulfonyl)amino]-N,N-bis(2-thienylmethyl) hexanamide; 6-[(benzylsulfonyl)(3-methoxybenzyl)amino]-N,N-bis(2-thienylmethyl)hexanamide; benzyl{6-[bis(2-thienylmethyl)amino]-6-oxohexyl}carbamate; tert-butyl {6-[bis(thiophen-2-ylmethyl)amino]-6-oxohexyl}carbamate; tert-butyl[(2S)-1-[bis(2-thienylmethyl)amino]-3-(4-hydroxyphenyl)-1-oxopropan-2-yl]carbamate; methyl(5S)-6-[bis(2-thienylmethyl)amino]-5-[(tert-butoxycarbonyl) amino]-6-oxohexanoate; (2S)-2-[acetyl(methyl)amino]-N,N-bis(2-thienylmethyl)hexanamide; benzyl{(5S)-5-[acetyl (methyl)amino]-6-[bis(2-thienylmethyl)amino]-6-oxohexyl}carbamate; (2S)-6-{[(benzyloxy)carbonyl] amino}-1-[bis(2-thienylmethyl)amino]-1-oxohexan-2-yl acetate; tert-butyl{(2S)-6-[benzyl(2-thienylsulfonyl) amino]-1-[bis(2-thienylmethyl)amino]-1-oxohexan-2-yl}carbamate; benzyl{(5S)-6-{bis[4-(trifluoromethoxy)benzyl]amino}-5-[(tert-butoxycarbonyl) amino]-6-oxohexyl}carbamate; benzyl[(5S)-5-[(tert-butoxycarbonyl) amino]-6-oxo-6-{(2-thienylmethyl)[2-(trifluoromethyl) benzyl]amino}hexyl]carbamate; benzyl[(5S)-5-[(tert-butoxycarbonyl)amino]-6-oxo-6-{(2-thienylmethyl) [2-(trifluoromethoxy)benzyl]amino}hexyl]carbamate; benzyl [(5S)-5-[(tert-butoxycarbonyl)amino]-6-{[2-(difluoromethoxy)benzyl]-(2-thienylmethyl)amino}-6-oxohexyl]carbamate; tert-butyl{6-[bis(4-methoxybenzyl) amino]-6-oxohexyl}carbamate; N-{6-[bis(4-methoxybenzyl) amino]-6-oxohexyl}-4-methoxybenzamide; N-{6-[bis(4-methoxybenzyl)amino]-6-oxohexyl}-4-methoxy-N-(4-methoxybenzyl)benzamide; N-{6-[bis(2-thienylmethyl)amino]-6-oxohexyl}-N-methyl-thiophene-2-carboxamide; 6-[(3-methoxybenzyl)(2-thienylacetyl) amino]-N,N-bis(2-thienylmethyl)hexanamide; tert-butyl{4-[bis(2-thienylmethyl) amino]-4-oxobutyl}carbamate; methyl(3S)-3-(1,3-benzodioxol-5-yl)-3-[({4-[bis(2-thienylmethyl)amino]-4-oxobutyl}carbamoyl) amino]propanoate; 6-{[(3-chloropropyl)sulfonyl]amino}-N,N-bis(4-methoxybenzyl)hexanamide; 6-(1,1-dioxido-1,2-thiazolidin-2-yl)-N,N-bis(4-methoxybenzyl)hexanamide; N,N-bis(4-methoxybenzyl)-6-({[2-(morpholin-4-yl)ethyl] sulfonyl}amino)hexanamide; 3-{[bis(2-thienylmethyl)carbamoyl]amino}-N,N-bis(2-thienylmethyl)propanamide; tert-butyl{3-[bis(2-thienylmethyl)amino]-3-oxopropyl}butylcarbamate; 3-{[bis(2-thienylmethyl)carbamoyl](butyl)amino}-N,N-bis(2-thienylmethyl)propanamide; 3-{butyl[(2-thienylmethyl)carbamoyl]amino}-N,N-bis(2-thienylmethyl)propanamide; 4-(1,1-dioxido-1,2-thiazolidin-2-yl)-N,N-bis(2-thienylmethyl)butanamide; N,N-bis(2-thienylmethyl)-3-{[(2-thienylmethyl)carbamoyl] amino}propanamide; benzyl{(5S)-6-[bis(2-thienylmethyl) amino]-5-hydroxy-6-oxohexyl}carbamate; benzyl{(5S)-6-[bis(2-thienylmethyl)amino]-5-cyano-6-oxohexyl}carbamate; benzyl{(5R)-5-azido-6-[bis(2-thienylmethyl)amino]-6-oxohexyl}carbamate; S-{(2R)-6-{[(benzyloxy)carbonyl]amino}-1-[bis(2-thienylmethyl) amino]-1-oxohexan-2-yl}ethanethioate; tert-butyl[(2S)-1-[bis(2-thienylmethyl)amino]-6-({[(4-bromobenzyl)oxy] carbonyl}amino)-1-oxohexan-2-yl]carbamate; 4-azidobenzyl {(5S)-6-[bis(2-thienylmethyl)amino]-5-[(tert-butoxycarbonyl)-amino]-6-oxohexyl}carbamate; benzyl{(5S)-6-[(4-bromobenzyl)(2-thienylmethyl)amino]-5-[(tert-butoxycarbonyl)amino]-6-oxohexyl}carbamate; tert-butyl[(2S)-1-[(4-azidobenzyl) (2-thienylmethyl)amino]-6-{[(benzyloxy)carbonyl]amino}-1-oxohexan-2-yl]carbamate; tert-butyl{(2S)-1-[(4-bromobenzyl)(2-thienylmethyl) amino]-1-oxohexan-2-yl}carbamate; benzyl{(5S)-6-[bis(3-thienylmethyl)amino]-5-[(tert-butoxycarbonyl)amino]-6-oxohexyl}carbamate; benzyl{(5S)-5-[(tert-butoxycarbonyl) amino]-6-[(cyclopropylmethyl)(2-thienylmethyl)amino]-6-oxohexyl}carbamate; and mixtures or combinations thereof.

In some embodiments, the compounds are selected from the group consisting of methyl(2S)-6-{[(benzyloxy)carbonyl]amino}-2-[benzyl(2-thienylsulfonyl)amino]hexanoate; methyl(2S)-6-{[(benzyloxy)carbonyl]amino}-2-[benzyl (phenylsulfonyl)amino]hexanoate; methyl(2S)-6-{[(benzyloxy)carbonyl]amino}-2-[(2-thienylcarbonyl)(2-thienylmethyl)amino]hexanoate; methyl(2S)-6-{[(benzyloxy) carbonyl]amino}-2-[(2-thienylacetyl) (2-thienylmethyl) amino]hexanoate; methyl(2S)-2-[benzyl(isobutylsulfonyl) amino]-6-{[(benzyloxy)carbonyl]amino}hexanoate; benzyl{(5S)-5-[(tert-butoxycarbonyl)amino]-6-[(2-thienylmethyl)(2-thienylsulfonyl)amino]hexyl}carbamate; benzyl {(5S)-5-[(tert-butoxycarbonyl)amino]-6-[(2-thienylacetyl) (2-thienylmethyl)amino]hexyl}carbamate; benzyl{(5S)-5-[(tert-butoxycarbonyl)amino]-6-[(methylsulfonyl)(2-thienylmethyl)amino]hexyl}carbamate; benzyl{(5S)-5-[(tert-butoxycarbonyl)amino]-6-[(phenylsulfonyl) (2-thienylmethyl)amino]hexyl}carbamate; benzyl{(5S)-5-[(tert-butoxycarbonyl)amino]-6-[(2-thienylcarbonyl)(2-thienylmethyl)amino]hexyl}carbamate; N,N'-heptane-1,7-diyl bis[N-(2-thienylmethyl)benzamide]; N,N'-heptane-1,7-diylbis[N-(2-thienylmethyl) thiophene-2-carboxamide]; benzyl[(5S)-5-[(tert-butoxycarbonyl)amino]-6-{[(4-methoxyphenyl)sulfonyl]-(2-thienylmethyl)amino}hexyl] carbamate; benzyl{(5S)-5-[(tert-butoxycarbonyl)amino]-6-[(4-methoxybenzoyl)(2-thienylmethyl)amino] hexyl}carbamate; N,N'-hexane-1,6-diylbis[N-(2-thienylmethyl)thiophene-2-carboxamide]; N,N'-hexane-1,6-diylbis[N-(3-methoxybenzyl)thiophene-2-carboxamide]; tert-butyl{5-[(4-methoxybenzyl)(2-thienylsulfonyl)amino] pentyl}carbamate; N,N'-pentane-1,5-diylbis[N-(3-methoxybenzyl)thiophene-2-sulfonamide]; N-(3-methoxybenzyl)-N-{5-[(2-thienylsulfonyl)amino]pentyl}thiophene-2-sulfonamide; tert-butyl{5-[(2-thienylcarbonyl)(2-thienylmethyl)amino]pentyl}carbamate; N-(3-methoxybenzyl)-N-{5-[(2-thienylcarbonyl)amino] pentyl}thiophene-2-carboxamide; N,N'-pentane-1,5-diylbis [N-(3-methoxybenzyl)thiophene-2-carboxamide]; and mixtures or combinations thereof.

In some embodiments, the compounds are selected from the group consisting of N,N,N',N'-tetrakis(2-thienylmethyl) pentanediamide; N-(3-methoxybenzyl)-N,N',N'-tris(2-thienylmethyl)pentanediamide; N,N,N'-tris(2-thienylmethyl) pentanediamide; N'-[2-(2-thienyl)ethyl]-N,N-bis(2-thienylmethyl)pentanediamide; N-[2-(2-thienyl)ethyl]-N,N',N'-tris(2-thienylmethyl)pentanediamide; N,N-bis(pyridin-4-ylmethyl)-N',N'-bis(2-thienylmethyl)pentanediamide; N,N-bis(pyridin-3-ylmethyl)-N',N'-bis(2-thienylmethyl) pentanediamide; N,N-bis(3-methoxybenzyl)-N',N'-bis(2-thienylmethyl)pentanediamide; N,N,N',N'-tetrakis(4-methoxybenzyl)pentanediamide; N,N,N',N'-tetrakis(2-thienylmethyl)hexanediamide; N,N,N',N'-tetrakis (4-methoxybenzyl)hexanediamide; N,N,N',N'-tetrakis(3-methoxybenzyl)hexanediamide; N,N,N',N'-tetrakis(2-thienylmethyl)heptanediamide; 2,2'-(1,3-phenylene) bis[N,N-bis(2-thienylmethyl)acetamide]; N,N,N',N'-tetrakis(4-methoxybenzyl)heptanediamide; N,N,N',N'-tetrakis(2-thienylmethyl)octanediamide; (3E)-N,N,N',N'-tetrakis (2-thienylmethyl)hex-3-enediamide; 2,2'-oxybis[N,N-bis(2-thienylmethyl)acetamide]; 3-oxo-1-(2-thienyl)-2-(2-thienylmethyl)-4,7,10-trioxa-2-azadodecan-12-yl bis(2-thienylmethyl)carbamate; N,N,N',N'-tetrakis(4-methoxybenzyl) succinamideethane-1,2-diyl bis[bis(2-thienylmethyl) carbamate]; N,N,N',N'-tetrakis(4-methoxybenzyl) octanediamide; N,N,N',N'-tetrakis(2-thienylmethyl) pyridine-3,5-dicarboxamide; N,N,N',N'-tetrakis(2-thienylmethyl) pyridine-2,6-dicarboxamide; N,N,N',N'-tetrakis(2-thienylmethyl)pyridine-2,4-dicarboxamide; 2,2'-(1,4-phenylene)bis[N,N-bis(2-thienylmethyl)acetamide]; 8-{2-[bis(2-thienylmethyl)amino]-2-oxoethoxy}-N,N-bis (2-thienylmethyl)quinoline-2-carboxamide; N,N'-bis(4-methoxybenzyl)-N,N'-bis(2-thienylmethyl)hexanediamide; tert-butyl{(2S)-1,6-bis[bis(2-thienylmethyl) amino]-1,6-dioxohexan-2-yl}carbamate; and mixtures or combinations thereof.

In some embodiments, the compounds are selected from the group consisting of N-{2-[bis(2-thienylmethyl)sulfamoyl]ethyl}-N-(2-thienylmethyl)thiophene-2-sulfonamide; N-{2-[bis(2-thienylmethyl)sulfamoyl]ethyl}-N-(2-thienylmethyl)thiophene-2-carboxamide; 2-{butyl[(2-thienylmethyl)carbamoyl]amino}-N,N-bis(2-thienylmethyl)ethanesulfonamide; 2-{[bis(2-thienylmethyl)carbamoyl](butyl) amino}-N,N-bis(2-thienylmethyl)ethanesulfonamide; N-{3-[bis(2-thienylmethyl)sulfamoyl]propyl}-N-(2-thienylmethyl)thiophene-2-sulfonamide; 2-[(methylsulfonyl)(2-thienylmethyl)amino]-N,N-bis(2-thienylmethyl)ethanesulfonamide; 2-{[bis(2-thienylmethyl) carbamoyl]amino}-N,N-bis(2-thienylmethyl)ethanesulfonamide; N-{2-[bis(2-thienylmethyl)sulfamoyl] ethyl}thiophene-2-sulfonamide; N-{2-[bis(2-thienylmethyl) sulfamoyl]ethyl}-2-(2-thienyl)acetamide; N-{2-[bis(2-thienylmethyl)sulfamoyl]ethyl}thiophene-2-carboxamide; N,N-bis(2-thienylmethyl)-2-{[(2-thienylmethyl)carbamoyl] amino}ethanesulfonamide; 2-({2-[bis(2-thienylmethyl)sulfamoyl]ethyl}amino)-N,N-bis(2-thienylmethyl)acetamide; 3-[{2-[bis(2-thienylmethyl)amino]-2-oxoethyl}(butyl) amino]-N,N-bis(2-thienylmethyl)propanamide; 2-[{2-[bis (2-thienylmethyl)sulfamoyl]ethyl}(methyl)amino]-N,N-bis (2-thienylmethyl)acetamide; 2-[{2-[bis(2-thienylmethyl) sulfamoyl]ethyl}(butyl)amino]-N,N-bis(2-thienylmethyl) acetamide; 3-({2-[bis(2-thienylmethyl)sulfamoyl] ethyl}amino)-N,N-bis(2-thienylmethyl)propanamide; 3-({2-[bis(2-thienylmethyl)sulfamoyl]ethyl}amino)-N,N-bis(4-methoxybenzyl)propanamide; 3-({2-[bis(4-methoxybenzyl)sulfamoyl]ethyl}amino)-N,N-bis(2-thienylmethyl) propanamide; 3-[{2-[bis(2-thienylmethyl)sulfamoyl]ethyl} (methyl)amino]-N,N-bis(2-thienylmethyl)propanamide; 3-[{2-[bis(4-methoxybenzyl)sulfamoyl]ethyl}(methyl) amino]-N,N-bis(2-thienylmethyl)propanamide; (2S)-2-({2-[bis(2-thienylmethyl) sulfamoyl]ethyl}amino)-N,N-bis(2-thienylmethyl)hexanamide; (2S)-2-({2-[bis(4-methoxybenzyl) sulfamoyl]ethyl}amino)-N,N-bis(2-thienylmethyl)hexanamide; 2-(acetyl{2-[bis(2-thienylmethyl) sulfamoyl]ethyl}amino)-N,N-bis(2-thienylmethyl)acetamide; 2-(acetyl{2-[bis(4-methoxybenzyl) sulfamoyl]ethyl}amino)-N,N-bis(2-thienyl-methyl)acetamide; and mixtures or combinations thereof.

In some embodiments, the compounds are selected from the group consisting of: tert-butyl[(2S)-1-{[bis(cyclopropylmethyl)carbamoyl]oxy}hexan-2-yl]carbamate; (2S)-2-[(tert-butoxycarbonyl)amino]hexyldiisobutylcarbamate; methyl(8S,12S)-12-(1,3-benzodioxol-5-yl)-8-butyl-4-isobutyl-2-methyl-5,10-dioxo-6-oxa-4,9,11-triazatetradecan-14-oate; benzyl{(5S)-6-[bis(cyclopropylmethyl) amino]-5-[(tert-butoxycarbonyl)amino]-6-oxohexyl}carbamate; and mixtures or combinations thereof.

In some embodiments, the compounds are selected from the group consisting of: methyl(3R)-3-(1,3-benzodioxol-5-yl)-3-[({(2R)-1-[bis(2-thienylmethyl)amino]-1-oxohexan-2-yl}carbamoyl)amino]propanoate; methyl(3S)-3-(1,3-benzodioxol-5-yl)-3-[({(2R)-6-{[(benzyloxy)carbonyl]amino}-1-[bis(thiophen-2-ylmethyl)amino]-1-oxohexan-2-yl}carbamoyl) amino]propanoate; methyl(3S)-3-(1,3-benzodioxol-5-yl)-3-[({(2R)-1-[bis(thiophen-2-yl-methyl) amino]-1-oxohexan-2-yl}carbamoyl)amino]propanoate; methyl(3R)-3-(1,3-benzodioxol-5-yl)-3-[({(2S)-1-[bis(2-thienylmethyl)amino]-1-oxohexan-2-yl}carbamoyl)amino] propanoate; methyl(3S)-3-(1,3-benzodioxol-5-yl)-3-[({2-

[bis(2-thienylmethyl)amino]-2-oxoethyl}carbamoyl)amino] propanoate; methyl(3S)-3-(1,3-benzodioxol-5-yl)-3-[({2-[bis(2-thienylmethyl)amino]-2-oxoethyl}carbamoyl)amino] propanoate; methyl(3S)-3-(1,3-benzodioxol-5-yl)-3-{[{2-[bis(2-thienylmethyl)amino]-2-oxoethyl}(methyl) carbamoyl]amino}propanoate; methyl(3R)-3-(1,3-benzodioxol-5-yl)-3-{[{2-[bis(2-thienylmethyl)amino]-2-oxoethyl}(methyl)carbamoyl]amino}propanoate; methyl (3R)-3-(1,3-benzodioxol-5-yl)-3-[({2-[bis(2-thienylmethyl) amino]-2-oxoethyl}carbamoyl)amino]propanoate; methyl (2R)—[({(2S)-1-[bis(thiophen-2-ylmethyl)amino]-1-oxo-hexan-2-yl}carbamoyl)amino](phenyl)ethanoate; methyl 3-[({(2S)-1-[bis(2-thienylmethyl)amino]-1-oxohexan-2-yl}carbamoyl)amino]propanoate; (2S)-2-[(isopropylcarbamoyl)amino]—N,N-bis(2-thienylmethyl)hexanamide; (2S)-2-[(methylcarbamoyl)amino]-N,N-bis(2-thienylmethyl)hexanamide; (2S)-2-[(benzylcarbamoyl)amino]-N,N-bis(2-thienylmethyl)hexanamide; (2R)-2-[(benzylcarbamoyl)amino]-N,N-bis(2-thienylmethyl)hexanamide; benzyl {(5S)-5-[(benzylcarbamoyl)amino]-6-[bis(2-thienylmethyl) amino]-6-oxohexyl}carbamate; (2S)-2-{[(1,3-benzodioxol-5-ylmethyl) carbamoyl]amino}-N,N-bis(2-thienylmethyl) hexanamide; benzyl[(5S)-6-[bis(2-thienylmethyl) amino]-6-oxo-5-{[(pyridin-3-ylmethyl)carbamoyl]amino}hexyl] carbamate; (2S)-2-{[(pyridin-3-ylmethyl)carbamoyl] amino}-N,N-bis(2-thienylmethyl)hexanamide; (2S)-2-({[(6-methoxypyridin-3-yl)methyl]carbamoyl}amino)-N,N-bis(-2-thienylmethyl) hexanamide; (2S)-2-({[3-(morpholin-4-yl)benzyl]carbamoyl}amino)-N,N-bis(2-thienylmethyl) hexanamide; (2S)-2-{[(4-hydroxybenzyl)carbamoyl] amino}-N,N-bis(2-thienylmethyl)hexanamide; (2S)-2-({[4-(dimethylamino)benzyl]carbamoyl}amino)-N,N-bis(2-thienylmethyl)hexanamide; benzyl[(5S)-6-[bis(2-thienylmethyl)amino]-5-({[3-(morpholin-4-yl)benzyl] carbamoyl}amino)-6-oxohexyl]carbamate; benzyl{(5S)-6-[bis(2-thienylmethyl)amino]-5-[({3-[(methylsulfonyl) amino]benzyl}carbamoyl)amino]-6-oxohexyl}carbamate; benzyl{(2S)-6-{[(benzyloxy)carbonyl]amino}-1-[bis(2-thienylmethyl)amino]-1-oxohexan-2-yl}carbamate; benzyl {(2S)-1-[bis(2-thienylmethyl) amino]-1-oxohexan-2-yl}carbamate; benzyl{(5S)-6-[bis(2-thienylmethyl)amino]-5-[(ethoxycarbonyl)amino]-6-oxohexyl}carbamate; benzyl [(5S)-6-[bis(2-thienylmethyl)amino]-5-(butyrylamino)-6-oxohexyl]carbamate; benzyl{(5S)-6-[bis(2-thienylmethyl) amino]-6-oxo-5-[(3-phenoxypropanoyl)amino] hexyl}carbamate; and mixtures or combinations thereof.

In some embodiments, the compounds are selected from the group consisting of: N-bis(2-thienylmethyl)benzenesulfonamide; N,N-bis(2-thienylmethyl)acetamide; 1-phenyl-N,N-bis(2-thienylmethyl)methanesulfonamide; 2-methyl-N,N-bis(2-thienylmethyl) propane-1-sulfonamide; N-(3-methoxybenzyl)-N-(2-thienylmethyl)benzenesulfonamide; N-(3-methoxybenzyl)-N-(2-thienylmethyl)propane-2-sulfonamide; N-(3-methoxybenzyl)-2-methyl-N-(2-thienylmethyl)propane-1-sulfonamide; N-(4-hydroxybenzyl)-3-methoxy-N-(2-thienylmethyl)benzenesulfonamide; N-[2-(2-thienyl)ethyl]-N-(2-thienylmethyl) benzenesulfonamide; N,N-dibenzylbenzenesulfonamide; N-(pyridin-3-ylmethyl)-N-(2-thienylmethyl)benzenesulfonamide; N-butyl-N-(2-thienylmethyl)benzenesulfonamide; N-(3-hydroxypropyl)-N-(2-thienylmethyl)benzenesulfonamide; N-(2-methoxyethyl)-N-(2-thienylmethyl)benzenesulfonamide; N-(2-methoxyethyl)-N-(2-thienylmethyl)thiophene-2-sulfonamide; N,N-bis(3-methoxybenzyl)benzenesulfonamide; N,N-bis(4-methoxybenzyl)thiophene-2-sulfonamide; 2-chloro-N,N-bis(2-thienylmethyl) benzenesulfonamide; 3-chloro-N,N-bis(2-thienylmethyl)benzenesulfonamide; 4-chloro-N,N-bis(2-thienylmethyl)benzenesulfonamide; 3-methoxy-N,N-bis(2-thienylmethyl) benzenesulfonamide; 4-methoxy-N,N-bis(2-thienylmethyl)benzenesulfonamide; N,N-bis(pyridin-4-ylmethyl)benzenesulfonamide; N,N-bis (pyridin-3-ylmethyl)benzenesulfonamide; N-(2-furylmethyl)-N-(2-thienylmethyl)benzenesulfonamide; N,N-bis(2-furylmethyl) benzenesulfonamide; N,N-bis(3-methoxybenzyl)thiophene-2-sulfonamide; methyl 3-[bis(3-methoxybenzyl)sulfamoyl]thiophene-2-carboxylate; 2-(hydroxymethyl)-N,N-bis(3-methoxybenzyl)thiophene-3-sulfonamide; N,N-bis(4-methoxybenzyl)-3-methylbenzenesulfonamide; N-phenyl-N-(2-thienylmethyl)benzenesulfonamide; N-phenyl-N-(2-thienylmethyl)thiophene-2-sulfonamide; N-(3-methoxybenzyl)-N-phenylthiophene-2-sulfonamide; N-(3-methoxybenzyl)-N-phenylbenzenesulfonamide; 3-(4-methoxyphenoxy)-N,N-bis(2-thienylmethyl)propane-1-sulfonamide; 4-methyl-N,N-bis(2-thienylmethyl)benzenesulfonamide; 2-methyl-N,N-bis(2-thienylmethyl) benzenesulfonamide; 3-methyl-N,N-bis(2-thienylmethyl) benzenesulfonamide; and mixtures or combinations thereof.

In some embodiments, the compounds are selected from the group consisting of: methyl(6S,10S)-1-(1,3-benzodioxol-5-yl)-6-butyl-3,8-dioxo-1-(2-thienyl)-2-(2-thienylmethyl)-4-oxa-2,7,9-triazadodecan-12-oate; methyl(6S,10S)-10-(1,3-benzodioxol-5-yl)-6-butyl-7-methyl-3,8-dioxo-1-(2-thienyl)-2-(2-thienylmethyl)-4-oxa-2,7,9-triazadodecan-12-oate; tert-butyl[(2S)-1-{[bis(2-thienylmethyl)carbamoyl] oxy}hexan-2-yl]carbamate; (2S)-2-{[(1,3-benzodioxol-5-ylmethyl)carbamoyl]amino}hexylbis(2-thienylmethyl) carbamate; methyl(6S,10S)-6-butyl-3,8-dioxo-10-phenyl-1-(2-thienyl)-2-(2-thienylmethyl)-4-oxa-2,7,9-triazadodecan-12-oate; (2S)-2-[(benzylcarbamoyl)amino]hexyl bis(2-thienylmethyl) carbamate; (2S)-2-({[(1S)-1-(1,3-benzodioxol-5-yl)-3-hydroxypropyl]carbamoyl}amino) hexyl bis(2-thienylmethyl)carbamate; methyl(6S,10R)-10-(1,3-benzodioxol-5-yl)-6-butyl-3,8-dioxo-1-(2-thienyl)-2-(2-thienylmethyl)-4-oxa-2,7,9-triazadodecan-12-oate; benzyl{(5S)-6-{[bis(2-thienylmethyl)carbamoyl]oxy}-5-[(tert-butoxycarbonyl)amino]hexyl}carbamate; methyl(9S, 13S)-13-(1,3-benzodioxol-5-yl)-9-({[bis(2-thienylmethyl) carbamoyl]oxy}methyl)-3,11-dioxo-1-phenyl-2-oxa-4,10, 12-triazapentadecan-15-oate; tert-butyl[(2R)-1-{[bis(2-thienylmethyl)carbamoyl]oxy}hexan-2-yl]carbamate; tert-butyl{[bis(2-thienylmethyl)carbamoyl](butyl) amino}acetate; benzyl{(5S)-6-{[bis(4-methoxybenzyl) carbamoyl]oxy}-5-[(tert-butoxycarbonyl)amino] hexyl}carbamate; tert-butyl[(2S)-1-{[bis(4-methoxybenzyl) carbamoyl]oxy}hexan-2-yl]carbamate; methyl(6S,10S)-10-(1,3-benzodioxol-5-yl)-6-butyl-2-(4-methoxybenzyl)-1-(4-methoxyphenyl)-3,8-dioxo-4-oxa-2,7,9-triazadodecan-12-oate; (2S)-2-({[(1S)-1-(1,3-benzodioxol-5-yl)-3-hydroxypropyl]carbamoyl}amino)hexylbis(4-methoxybenzyl)carbamate; (2S)-2-[(tert-butoxycarbonyl) amino]hexyldibenzylcarbamate; methyl(6S,10S)-10-(1,3-benzodioxol-5-yl)-2-benzyl-6-butyl-3,8-dioxo-1-phenyl-4-oxa-2,7,9-triazadodecan-12-oate; tert-butyl[(2S)-1-{[bis(4-methylbenzyl) carbamoyl]oxy}hexan-2-yl]carbamate; methyl(6S,10S)-10-(1,3-benzodioxol-5-yl)-6-butyl-2-(4-methylbenzyl)-1-(4-methylphenyl)-3,8-dioxo-4-oxa-2,7,9-triazadodecan-12-oate; tert-butyl[(2S)-1-{[bis(4-chlorobenzyl)carbamoyl]oxy}hexan-2-yl]carbamate; methyl(6S,10S)-10-(1,3-benzodioxol-5-yl)-6-butyl-2-(4-chlorobenzyl)-1-(4-chlorophenyl)-3,8-dioxo-4-oxa-2,7,9-triazadodecan-12-oate; methyl(6S,10S)-10-(1,3-benzodioxol-5-yl)-2-(4-bromobenzyl)-6-butyl-3,8-dioxo-1-(2-thienyl)-4-oxa-2,7,9-triazadodecan-12-oate; methyl(6S,10S)-2-(4-azidoobenzyl)-

10-(1,3-benzodioxol-5-yl)-6-butyl-3,8-dioxo-1-(2-thienyl)-4-oxa-2,7,9-triazadodecan-12-oate; (2S)-2-[(tert-butoxycarbonyl)amino]hexyl phenyl(2-thienylmethyl)carbamate; methyl(6S,10S)-10-(1,3-benzodioxol-5-yl)-6-butyl-3,8-dioxo-2-phenyl-1-(2-thienyl)-4-oxa-2,7,9-triazadodecan-12-oate; tert-butyl[(2S)-1-{[bis(3-thienylmethyl)carbamoyl]oxy}hexan-2-yl]carbamate; methyl(6 S,10S)-10-(1,3-benzodioxol-5-yl)-6-butyl-3,8-dioxo-1-(3-thienyl)-2-(3-thienylmethyl)-4-oxa-2,7,9-triazadodecan-12-oate; benzyl [(5S)-5-[(tert-butoxycarbonyl)amino]-6-{[butyl(2-thienylmethyl)carbamoyl]oxy}hexyl]carbamate; (2S)-2-[(tert-butoxycarbonyl) amino]hexyl butyl(2-thienylmethyl) carbamate; methyl(3S,7S)-3-(1,3-benzodioxol-5-yl)-7-butyl-5,10-dioxo-11-(2-thienylmethyl)-9-oxa-4,6,11-triazapentadecan-1-oate; benzyl[(5S)-5-[(tert-butoxycarbonyl)amino]-6-{[(2-methoxyethyl)(2-thienylmethyl)carbamoyl]oxy}hexyl]carbamate; (2S)-2-{[(4-bromobenzyl)carbamoyl]amino}hexyl bis(2-thienylmethyl) carbamate; (2S)-2-{[(4-azidobenzyl)carbamoyl] amino}hexyl bis(2-thienylmethyl)carbamate; tert-butyl [(2S)-1-{[bis(2-thienylmethyl)carbamoyl]thio}hexan-2-yl] carbamate; and methyl(6S,10S)-10-(1,3-benzodioxol-5-yl)-6-butyl-3,8-dioxo-1-(2-th-ienyl)-2-(2-thienylmethyl)-4-thia-2,7,9-triazadodecan-12-oate.

In some embodiments, the compounds are selected from the group consisting of: benzyl{(5R)-5-[(tert-butoxycarbonyl)amino]-6-[(3-methoxybenzyl)(2-thienylmethyl)amino]-6-oxohexyl}carbamate; benzyl{(5R)-6-[bis(3-methoxybenzyl)amino]-5-[(tert-butoxycarbonyl)amino]-6-oxohexyl}carbamate; benzyl{(5S)-6-[bis(4-methoxybenzyl) amino]-5-[(tert-butoxycarbonyl)amino]-6-oxohexyl}carbamate; benzyl{(5S)-5-[(tert-butoxycarbonyl) amino]-6-oxo-6-[(pyridin-3-ylmethyl)(-2-thienylmethyl) amino]hexyl}c arbamate; benzyl{(5S)-5-[(tert-butoxycarbonyl)amino]-6-oxo-6-[(pyridin-4-ylmethyl)(-2-thienylmethyl)amino]hexyl}carbamate; (2S)-2-[methyl (phenylsulfonyl)amino]-N,N-bis(2-thienylmethyl) hexanamide; (2S)-2-({[3-(4-methoxyphenoxy)propyl] sulfonyl}amino)-N,N-bis(2-thienylmethyl)hexanamide; benzyl{(5R)-6-[bis(2-thienylmethyl)amino]-5-[(tert-butoxycarbonyl)amino]-6-oxohexyl}carbamate; benzyl{(5S)-6-[bis(2-thienylmethyl)amino]-5-[(tert-butoxycarbonyl) amino]-6-oxohexyl}carbamate; benzyl{(5S)-6-[bis(2-thienylmethyl)amino]-6-oxo-5-[(2-thienylsulfonyl)amino] hexyl}carbamate; tert-butyl{(2S)-1-[bis(2-thienylmethyl) amino]-1-oxo-6-[(2-thienylsulfonyl)amino]hexan-2-yl}carbamate; 6-[methyl(2-thienylsulfonyl) amino]-N,N-bis (2-thienylmethyl)hexanamide; 6-[(2-thienylacetyl)amino]-N,N-bis(2-thienylmethyl)hexanamide; benzyl{(4S)-5-[bis (2-thienylmethyl)amino]-4-[(tert-butoxycarbonyl)amino]-5-oxopentyl}carbamate; benzyl[(5S)-5-[(tert-butoxycarbonyl) amino]-6-oxo-6-{(2-thienylmethyl)[2-(trifluoromethyl)benzyl]amino}hexyl]carbamate; benzyl[(5S)-5-[(tert-butoxycarbonyl)amino]-6-oxo-6-{(2-thienylmethyl) [2-(trifluoromethoxy) benzyl]amino}hexyl]carbamate; benzyl[(5S)-5-[(tert-butoxycarbonyl) amino]-6-{[2-(difluoromethoxy) benzyl]-(2-thienylmethyl)amino}-6-oxohexyl]carbamate; tert-butyl{6-[bis(4-methoxybenzyl)amino]-6-oxohexyl}carbamate; N-{6-[bis(4-methoxybenzyl) amino]-6-oxohexyl}-4-methoxy-N-(4-methoxybenzyl)benzamide; N-{6-[bis(2-thienylmethyl)amino]-6-oxohexyl}-N-methyl-thiophene-2-carboxamide; 6-[(3-methoxybenzyl)(2-thienylacetyl)amino]-N,N-bis(2-thienylmethyl)hexanamide; methyl(3S)-3-(1,3-benzodioxol-5-yl)-3-[({4-[bis(2-thienylmethyl)amino]-4-oxobutyl}carbamoyl)amino]propanoate; 6-{[(3-chloropropyl) sulfonyl]amino}-N,N-bis(4-methoxybenzyl)hexanamide; 3-{[bis(2-thienylmethyl)carbamoyl] amino}-N,N-bis(2-thienylmethyl)propanamide; 3-{butyl [(2-thienylmethyl)carbamoyl]amino}—N,N-bis(2-thienylmethyl)propanamide; benzyl{(5S)-6-[bis(2-thienylmethyl)amino]-5-cyano-6-oxohexyl}carbamate; benzyl{(5R)-5-azido-6-[bis(2-thienylmethyl)amino]-6-oxohexyl}carbamate; and benzyl{(5S)-6-[bis(3-thienylmethyl)amino]-5-[(tert-butoxycarbonyl) amino]-6-oxohexyl}carbamate.

In some embodiments, the compounds are selected from the group consisting of: N-(3-methoxybenzyl)-N,N',N'-tris (2-thienylmethyl)pentanediamide; N-[2-(2-thienyl)ethyl]-N,N',N'-tris(2-thienylmethyl)pentanediamide; N,N-bis(3-methoxybenzyl)-N',N'-bis(2-thienylmethyl) pentanediamide; N,N-bis(pyridin-4-ylmethyl)-N',N'-bis(2-thienylmethyl)pentanediamide; N,N,N',N'-tetrakis(2-thienylmethyl)hexanediamide; N,N,N',N'-tetrakis(3-methoxybenzyl)hexanediamide; N,N,N',N'-tetrakis(4-methoxybenzyl) hexanediamide; (3E)-N,N,N',N'-tetrakis(2-thienylmethyl)hex-3-enediamide; N,N,N',N'-tetrakis (2-thienylmethyl)pentanediamide; N,N,N',N'-tetrakis(4-methoxybenzyl)pentanediamide; 2,2'-oxybis[N,N-bis(2-thienylmethyl)acetamide]; N,N,N',N'-tetrakis(2-thienylmethyl)octanediamide; N,N,N',N'-tetrakis(2-thienylmethyl) heptanediamide; 3-oxo-1-(2-thienyl)-2-(2-thienylmethyl)-4,7,10-trioxa-2-azadodecan-12-yl bis(2-thienylmethyl) carbamate; 2,2'-(1,3-phenylene)bis[N,N-bis(2-thienylmethyl)acetamide]; N,N,N',N'-tetrakis (4-methoxybenzyl)heptanediamide; N,N,N',N'-tetrakis(4-methoxybenzyl) succinamideethane-1,2-diyl bis[bis(2-thienylmethyl)carbamate]; N,N,N',N'-tetrakis (4-methoxybenzyl)octanediamide; N,N,N',N'-tetrakis(2-thienylmethyl) pyridine-3,5-dicarboxamide; N,N,N',N'-tetrakis(2-thienylmethyl)pyridine-2,6-dicarboxamide; N,N,N',N'-tetrakis(2-thienylmethyl) pyridine-2,4-dicarboxamide; 2,2'-(1,4-phenylene)bis[N,N-bis(2-thienylmethyl)acetamide]; and N,N'-bis(4-methoxybenzyl)-N,N'-bis(2-thienylmethyl) hexanediamide.

In some embodiments, the compounds are selected from the group consisting of: methyl(2S)-6-{[(benzyloxy)carbonyl]amino}-2-[benzyl(phenylsulfonyl)amino]hexanoate; methyl(2S)-6-{[(benzyloxy)carbonyl]amino}-2-[benzyl(2-thienylsulfonyl)amino]hexanoate; methyl(2S)-6-{[(benzyloxy)carbonyl]amino}-2-[(2-thienylacetyl)(2-thienylmethyl)amino]hexan oate; methyl(2S)-6-{[(benzyloxy) carbonyl]amino}-2-[(2-thienylcarbonyl)(2-thienylmethyl) amino]hexanoate; benzyl{(5S)-5-[(tert-butoxycarbonyl) amino]-6-[(2-thienylmethyl) (2-thienylsulfonyl)amino] hexyl}carbamate; benzyl{(5S)-5-[(tert-butoxycarbonyl) amino]-6-[(phenylsulfonyl)(2-thienylmethyl)amino] hexyl}carbamate; benzyl{(5S)-5-[(tert-butoxycarbonyl) amino]-6-[(2-thienylacetyl)(2-thienylmethyl)amino] hexyl}carbamate; benzyl{(5S)-5-[(tert-butoxycarbonyl) amino]-6-[(methylsulfonyl)(2-thienylmethyl) amino] hexyl}carbamate; benzyl{(5S)-5-[(tert-butoxycarbonyl) amino]-6-[(2-thienylcarbonyl) (2-thienylmethyl)amino] hexyl}carbamate; benzyl[(5S)-5-[(tert-butoxycarbonyl) amino]-6-{[(4-methoxyphenyl)sulfonyl]-(2-thienylmethyl) amino}hexyl]carbamate; benzyl{(5S)-5-[(tert-butoxycarbonyl)amino]-6-[(4-methoxybenzoyl)(2-thienylmethyl)amino]hexyl}carbamate; N,N'-heptane-1,7-diylbis[N-(2-thienylmethyl)thiophene-2-carboxamide]; N,N'-heptane-1,7-diylbis[N-(2-thienylmethyl)benzamide; N,N'-hexane-1,6-diylbis [N-(2-thienylmethyl)thiophene-2-carboxamide]; N,N'-hexane-1,6-diylbis[N-(3-methoxybenzyl) thiophene-2-carboxamide]; tert-butyl{5-[(4-methoxybenzyl)(2-thienylsulfonyl) amino]pentyl}carbamate; N-(3-methoxybenzyl)-N-{5-[(2-thienylsulfonyl)amino]

pentyl}thiophene-2-sulfonamide; tert-butyl{(2S)-1,6-bis[bis(2-thienylmethyl)amino]-1,6-dioxohexan-2-yl}carbamate; tert-butyl{5-[(2-thienylcarbonyl)(2-thienylmethyl)amino]pentyl}carbamate; N-(3-methoxybenzyl)-N-{5-[(2-thienylcarbonyl)amino]pentyl}thiophenthophene-2-carboxamide; and N,N'-pentane-1,5-diylbis[N-(3-methoxybenzyl)thiophene-2-carboxamide].

In some embodiments, the compounds are selected from the group consisting of: N-{2-[bis(2-thienylmethyl)sulfamoyl]ethyl}-N-(2-thienylmethyl)thiophene-2-carboxamide; 2-{butyl[(2-thienylmethyl)carbamoyl]amino}-N,N-bis(2-thienylmethyl)ethanesulfonamide; 2-[(methylsulfonyl)(2-thienylmethyl)amino]-N,N-bis(2-thienylmethyl)ethanesulfonamide; 2-{[bis(2-thienylmethyl)carbamoyl]amino}-N,N-bis(2-thienylmethyl)ethanesulfonamide; N-{2-[bis(2-thienylmethyl)sulfamoyl]ethyl}thiophene-2-sulfonamide; N-{2-[bis(2-thienylmethyl) sulfamoyl]ethyl}-2-(2-thienyl) acetamide; N-{2-[bis(2-thienylmethyl)sulfamoyl] ethyl}thiophene-2-carboxamide; N,N-bis(2-thienylmethyl)-2-{[(2-thienylmethyl)carbamoyl] amino}ethanesulfonamide; 2-({2-[bis(2-thienylmethyl) sulfamoyl]ethyl}amino)-N,N-bis(2-thienylmethyl) acetamide; 3-[{2-[bis(2-thienylmethyl)amino]-2-oxoethyl}(butyl)amino]-N,N-bis(2-thienylmethyl)propanamide; 2-[{2-[bis(2-thienylmethyl)sulfamoyl]ethyl}(methyl) amino]-N,N-bis(2-thienylmethyl)acetamide; 3-({2-[bis(2-thienylmethyl)sulfamoyl]ethyl}amino)-N,N-bis(2-thienylmethyl)propanamide; 3-({2-[bis(2-thienylmethyl) sulfamoyl]ethyl}amino)-N,N-bis(4-methoxybenzyl) propanamide; 2-(acetyl{2-[bis(2-thienylmethyl)sulfamoyl] ethyl}amino)-N,N-bis(2-thienylmethyl)acetamide; and 2-(acetyl{2-[bis(4-methoxybenzyl)sulfamoyl] ethyl}amino)-N,N-bis(2-thienylmethyl)acetamide.

In some embodiments, the compounds are selected from the group consisting of: tert-butyl[(2S)-1-{[bis(cyclopropylmethyl)carbamoyl]oxy}hexan-2-yl]carbamate; (2S)-2-[(tert-butoxycarbonyl)amino]hexyldiisobutylcarbamate; methyl(8S,12S)-12-(1,3-benzodioxol-5-yl)-8-butyl-4-isobutyl-2-methyl-5,10-dioxo-6-oxa-4,9,11-triazatetradecan-14-oate; and benzyl{(5S)-6-[bis(cyclopropylmethyl) amino]-5-[(tert-butoxycarbonyl)amino]-6-oxohexyl}carbamate.

While many embodiments of compounds of Formulas (I-VIII) are in the form in vivo, some compounds may be precursor compounds to a disclosed compounds. For example, a disclosed compound may exist as a stereoisomer wherein asymmetric or chiral centers are present. These stereoisomers are "R" or "S" depending on the configuration of substituents around the chiral carbon atom. The present disclosure contemplates various stereoisomers and mixtures thereof. Stereoisomers include enantiomers and diastereomers, and mixtures of enantiomers or diastereomers. Individual stereoisomers of some activator compounds may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Various embodiments of the disclosed compounds may exist in unsolvated or solvated forms, including hydrated forms, such as hemi-hydrates. In general, the solvated forms, with pharmaceutically acceptable solvents such as water and ethanol among others are equivalent to the unsolvated forms for the purposes of this disclosure. Pharmaceutical compositions containing the disclosed compounds are described below.

Pharmaceutical Compositions

The compounds described herein may be used to form pharmaceutically acceptable salts derived from inorganic or organic acids. The phrase "pharmaceutically acceptable salt" means those salts which are, within the scope of sound medical judgment, suitable for use in contact with the tissues of humans, mammals, or animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in J. Pharmaceutical Sciences, 1977, 66: 1 et seq. The salts may be prepared in situ during the final isolation and purification of the compounds or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphor sulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, nicotinate, 2-naphthalene sulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

In some embodiments, basic addition salts are prepared in situ during the final isolation and purification of a disclosed compound by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

Dosage forms for topical administration of a disclosed compounds include powders, sprays, ointments, and inhalants. The active compound or compounds may be mixed under sterile conditions with a pharmaceutically acceptable carrier and any needed preservatives, buffers or propellants which may be required. Opthalmic formulations, eye ointments, powders and solutions are also contemplated in some embodiments.

Actual dosage levels of active ingredients in the pharmaceutical compositions of this disclosure may be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used for various therapeutic treatments, a therapeutically effective amount of one or more of the disclosed compounds be employed in pure form or, where such forms exist, in pharmaceutically acceptable salt, ester or pro-drug form. In some cases, the compound is administered as a pharmaceutical composition containing the compound of interest in combination with one or more pharmaceutically acceptable excipients. The phrase "therapeutically effective amount" of a disclosed activator compound means a sufficient amount of the compound to treat disorders, at a reasonable benefit/risk ratio applicable to any medical treatment. It will be understood, however, that the total daily usage of the disclosed compounds and compositions will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the disclosed compounds administered to a human or lower animal may range from about 1 ng/kg/day to about 1000 mg/kg/day and any range in between these extremes. For purposes of oral administration, in some embodiments doses are in the range of from about 100 ng/kg/day to about 5 mg/kg/day. If desired, the effective daily dose can be divided into multiple doses for purposes of administration; consequently, single dose compositions may contain such amounts or submultiples thereof to make up the daily dose.

In some instances, a pharmaceutical composition comprises one or more of the disclosed compounds formulated together with one or more non-toxic pharmaceutically acceptable carriers. The pharmaceutical compositions may be specially formulated for oral administration in solid or liquid form, for parenteral injection or for rectal administration.

A disclosed pharmaceutical compositions may be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion. In some implementations, a pharmaceutical composition comprises a disclosed compound and a physiologically tolerable or acceptable diluent, carrier, adjuvant or vehicle, which are collectively referred to herein as diluents, for parenteral injection, for intranasal delivery, for oral administration in solid or liquid form, for rectal or topical administration, or the like.

In some instances, a composition is delivered through a catheter for local delivery at a target site, via an intracoronary stent (a tubular device composed of a fine wire mesh), or via a biodegradable polymer. In some embodiments, an activator compound is complexed to a ligand such as an antibody, for targeted delivery.

Compositions suitable for parenteral injection may comprise physiologically acceptable, sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof. These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like. Proper fluidity can be maintained, for example, by the use of coating materials such as lecithin, by the maintenance of the required particle size in the case of dispersions and by the use of surfactants.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline foam. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and I) lubricants such as talc, calcium stearate, magnesium stearate, solid polyethylene glycols, sodium lauryl sulfate and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes. The active compounds can also be in micro-encapsulated form, if appropriate, with one or more of the above-mentioned excipients. Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents. Compositions for rectal or vaginal administration are generally suppositories which may be prepared by mixing one or more of the disclosed compounds with suitable non-irritating excipients or carriers such as cocoa butter, polyethylene glycol or a suppository wax which are solid at room temperature but liquid at body temperature and therefore melt in the rectum or vaginal cavity and release the active compound.

For some applications, a disclosed compound is administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. In some embodiments, a composition in liposome form contains, in addition to a disclosed activator compound, stabilizers, preservatives, excipients and the like. In certain embodiments, the lipids are natural and synthetic phospholipids and phosphatidyl cholines (lecithins) used separately or together. Methods of forming liposomes are known in the art. See, for example, Prescott, Ed., Methods in Cell Biology, Volume XIV, Academic Press, New York, N.Y. (1976), p. 33 et seq.

Suitable Components for Use in the Disclosure

Suitable integrins targeted by these compounds include, without limitation, β4β1, α4β7, β5β1, αLβ2 and/or αVβ3.

Suitable ligands include, without limitation, VCAM-1, fibronectin, MAdCAM-1, ICAM-1, ICAM-2, and/or vitronectin.

Suitable acid addition salts derived from their corresponding acids include, without limitation, acetate, adipate, alginate, citrate, aspartate, benzoate, benzenesulfonate, bisulfate, butyrate, camphorate, camphor sulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, nicotinate, 2-naphthalene sulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Exemplary examples of corresponding inorganic acids include, without limitation, hydrochloric acid, hydrobromic acid, sulphuric acid, phosphoric acid, or mixtures and combinations thereof. Exemplary examples of corresponding organic acids include, without limitation, oxalic acid, maleic acid, adipic acid, succinic acid, citric acid, or mixtures and combinations thereof.

Suitable alkylating agents include, without limitation, lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Such alkylated compounds of Formula (I) may be used to form water-soluble or oil-soluble or dispersible products are thereby obtained.

Suitable pharmaceutically acceptable metal salts including, without limitation, group 1 metals, group 2 metals, group 13 metals, transition metals (e.g., groups 3-30), Ge, Sn, Bi, Sb, Se, lanthanide metals, actinide metals or mixtures and combinations thereof. Exemplary examples of metals include, without limitation, lithium, sodium, potassium, magnesium, calcium, aluminum, or mixtures and combinations thereof.

Suitable quaternary ammonium salts and amine cation salts include, without limitation, ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

Suitable cancer or cancerous growth treatable with one or more of the compounds of Formula (I) include, without limitation, any cancer or cancerous growth evidenced by the present of a solid tumor or stroma or related cancerous structures.

Suitable cytotoxic T lymphocyte cells (CTLs) include, without limitation, tumor infiltrating lymphocytes, lymphocytes expanded in an antigen specific manner, lymphocytes engineered to express chimeric antigen receptors).

Suitable effector cells for use in the compositions of this disclosure include, without limitation, any cell that may be activated by their cognate tumor-antigen, and that may be involved in eliminating cancer cells. Exemplary examples of effector cell types may include, without limitation, 1) Tumor Infiltrating Lymphocytes (TIL) are lymphocytes isolated from tumors and expanded ex vivo that possess cells surface markers including but not limited CD8 or CD4, 2) T-cell clones reactive to one or plurality of tumor antigens that possess cells surface markers including but not limited CD8 or CD4, 3) T-cells genetically engineered with tumor specific-T-cell receptors or -chimeric antigen receptors that possess cells surface markers including but not limited CD8 or CD4, and/or 4) natural killer cells reactive to a specific or plurality of tumor antigens.

Suitable anti-cancer drugs or agents that may be used in combination with the compounds of this disclosure include, without limitation, any drug that activates an anti-tumor immune T cell response through activatoric targets such as CD137 and OX40, or by exposing immune cells to antigens through vaccines and oncolytic viruses. Suitable drugs also including drugs that prevent immune suppression by targeting inhibitory receptors such as PD-1, CTLA-4, LAG-3, TIM-3, and/or BLTA as well as inhibiting myeloid derived suppressor cells, tumor associated macrophages, and/or regulatory T cells are in development. Exemplary commercial products include, without limitation, ABVD, AC, ACE, Abiraterone (Zytiga), Abraxane, Abstral, Actinomycin D, Actiq, Adriamycin, Afatinib (Giotrif), Afinitor, Aflibercept (Zaltrap), Aldara, Aldesleukin (IL-2, Proleukin or interleukin 2), Alemtuzumab (MabCampath), Alkeran, Amsacrine (Amsidine, m-AMSA), Amsidine, Anastrozole (Arimidex), Ara C, Aredia, Arimidex, Aromasin, Arsenic trioxide (Trisenox, ATO), Asparaginase (Crisantaspase, Erwinase), Atezolizumab (MPDL3280A), Axitinib (Inlyta), Azacitidine (Vidaza), BEACOPP, BEAM, Bendamustine (Levact), Bevacizumab (Avastin), Bexarotene (Targretin), Bicalutamide (Casodex), Bleomycin, Bleomycin, etoposide and platinum (BEP), Bortezomib (Velcade), Bosulif, Bosutinib (Bosulif), Brentuximab (Adcetris), Brufen, Buserelin (Suprefact), Busilvex, Busulfan (Myleran, Busilvex), CAPE-OX, CAPOX, CAV, CAVE, CCNU, CHOP, CMF, CMV, CTD, CVP, Cabazitaxel (Jevtana), Cabozantinib (Cometriq), Caelyx, Calpol, Campto, Capecitabine (Xeloda), Caprelsa, Carbo MV, CarboTaxol, Carboplatin, Carboplatin and etoposide, Carboplatin and paclitaxel, Carmustine (BCNU, Gliadel), Casodex, Ceritinib (Zykadia), Cerubidin, Cetuximab (Erbitux), ChlVPP, Chlorambucil (Leukeran), Cisplatin, Cisplatin and Teysuno, Cisplatin and capecitabine (CX), Cisplatin, etoposide and ifosfamide (PEI), Cisplatin, fluorouracil (5-FU) and trastuzumab, Cladribine (Leustat, LITAK), Clasteon, Clofarabine (Evoltra), Co-codamol (Kapake, Solpadol, Tylex), Cometriq, Cosmegen, Crisantaspase, Crizotinib (Xalkori), Cyclophosphamide, Cyprostat, Cyproterone acetate (Cyprostat), Cytarabine (Ara C, cytosine arabinoside), Cytarabine into spinal fluid, Cytosine arabinoside, DHAP, DTIC, Dabrafenib (Tafinlar), Dacarbazine (DTIC), Dacogen, Dactinomycin (actinomycin D, Cosmegen), Dasatinib (Sprycel), Daunorubicin, De Gramont, Decapeptyl SR, Decitabine (Dacogen), Degarelix (Firmagon), Denosumab (Prolia, Xgeva), Depocyte, Dexamethasone, Diamorphine, Disodium pamidronate, Disprol, Docetaxel (Taxotere), Docetaxel, cisplatin and fluorouracil (TPF), Doxifos, Doxil, Doxorubicin (Adriamycin), Doxorubicin and ifosfamide (Doxifos), Drogenil, Durogesic, E-CMF (Epi-CMF), EC, ECF, EOF, EOX, EP, ESHAP, Effentora, Efudix, Eldisine, Eloxatin, Enzalutamide (Xtandi), Epirubicin (Pharmorubicin), Epirubicin, carboplatin and capecitabine (ECarboX), Epirubicin, cisplatin and capecitabine (ECX), Eposin, Erbitux, Eribulin (Halaven), Erlotinib (Tarceva), Erwinase, Estracyt, Etopophos, Etoposide (Eposin, Etopophos, Vepesid), Etoposide, leucovorin and fluorouracil (ELF), Everolimus (Afinitor), Evoltra, Exemestane (Aromasin), FAD, FC, FEC, FEC-T chemotherapy, FMD, FOLFIRINOX, Faslodex, Femara, Fentanyl, Firmagon, Fludara, Fludarabine (Fludara), Fludarabine, cyclophosphamide and rituximab (FCR), Fluorouracil (5FU), Flutamide, Folinic acid, fluorouracil and irinotecan (FOLFIRI), Folinic acid, fluorouracil and oxaliplatin (FOLFOX), Fulvestrant (Faslodex), G-CSF, Gefitinib (Iressa), GemCarbo (gemcitabine and carboplatin), GemTaxol, Gemcitabine (Gemzar), Gemcitabine and capecitabine (GemCap), Gemcitabine and cisplatin (GC), Gemcitabine and paclitaxel (GemTaxol), Gemzar, Giotrif, Gliadel, Glivec, Gonapeptyl Depot, Goserelin (Zoladex), Goserelin (Zoladex, Novgos), Granulocyte colony stimulating factor (G-CSF), Halaven, Herceptin, Hycamtin, Hydrea, Hydroxycarbamide (Hydrea), Hydroxyurea, I-DEX, ICE, IL-2, IPE, Ibandronic acid, Ibritumomab (Zevalin), Ibuprofen (Brufen, Nurofen), Iclusig, Idarubicin (Zavedos), Idarubicin and dexamethasone, Idelalisib (Zydelig), Ifosfamide (Mitoxana), Imatinib (Glivec), Imiquimod cream (Aldara), Imnovid, Instanyl, Interferon (Intron A), Interleukin, Intron A, Ipilimumab (Yervoy), Iressa, Irinotecan (Campto), Irinotecan and capecitabine (XELIRI), Irinotecan de Gramont, Irinotecan modified de Gramont, Javlor, Jevtana, Kadcyla, Kapake, Keytruda, Lanvis, Lapatinib (Tyverb), Lenalidomide (Revlimid), Letrozole (Femara), Leukeran, Leuprorelin (Prostap, Lutrate), Leustat, Levact, Liposomal doxorubicin, Litak, Lomustine (CCNU), Lynparza, Lysodren, MIC, MM, MMM, MST Continus, MVAC, MVP, MabCampath, Mabthera, Maxtrex, Medroxyprogesterone acetate (Provera), Megace, Megestrol acetate (Megace), Melphalan (Alkeran), Melphalan, prednisolone and thalidomide (MPT), Mepact, Mercaptopurine (Xaluprine), Methotrexate (Maxtrex), Methyl prednisolone, Mifamurtide (Mepact), Mitomycin C, Mitotane, Mitoxana, Mitoxantrone (Mitozantrone), Morphgesic SR, Morphine, Myleran, Myocet, Nab-paclitaxel, Nab-paclitaxel (Abraxane), Navelbine, Nelarabine (Atriance), Nexavar, Nilotinib (Tasigna), Nintedanib (Vargatef), Nipent, Nivolumab (Opdivo), Novgos, Nurofen, Ofatumumab (Arzerra), Olaparib (Lynparza), Oncovin, Onkotrone, Opdivo, Oramorph, Oxaliplatin (Eloxatin), Oxaliplatin and capecitabine (XELOX), PAD, PC (paclitaxel and carboplatin, CarboTaxol), PCV, PE, PMitCEBO, POMB/ACE, Paclitaxel (Taxol), Paclitaxel and carboplatin, Pamidronate, Panadol, Panitumumab (Vectibix), Paracetamol, Pazopanib (Votrient), Pembrolizumab (Keytruda), Pemetrexed (Alimta), Pemetrexed and carboplatin, Pemetrexed and cisplatin, Pentostatin (Nipent), Perjeta, Pertuzumab (Perjeta), Pixantrone (Pixuvri), Pixuvri, Pomalidomide (Imnovid), Ponatinib (Iclusig), Potactasol, Prednisolone, Procarbazine, Proleukin, Prolia, Prostap, Provera, Purinethol, R—CHOP, R—CVP, R-DHAP, R-ESHAP, R-GCVP, RICE, Raloxifene, Raltitrexed (Tomudex), Regorafenib (Stivarga), Revlimid, Rituximab (Mabthera), Sevredol, Sodium clodronate (Bonefos, Clasteon), Solpadol, Sorafenib (Nexavar), Stanford V, Steroids (dexamethasone, prednisolone, methylprednisolone), Streptozocin (Zanosar), Sunitinib (Sutent), Sutent, TAC, TIP, Tafinlar, Tamoxifen, Tarceva, Targretin, Tasigna, Taxol, Taxotere, Taxotere and cyclophosphamide (TC), Temodal, Temozolomide (Temodal), Temsirolimus (Torisel), Tepadina, Teysuno, Thalidomide, Thiotepa (Tepadina), Tioguanine (thioguanine, 6-TG, 6-tioguanine), Tomudex, Topotecan (Hycamtin, Potactasol), Torisel, Trabectedin (Yondelis), Trastuzumab (Herceptin), Trastuzumab emtansine (Kadcyla), Treosulfan, Tretinoin (Vesanoid, ATRA), Triptorelin (Decapeptyl SR, Gonapeptyl Depot), Trisenox, Tylex, Tyverb, VIDE, Vandetanib (Caprelsa), Vargatef, VeIP, Vectibix, Velbe, Velcade, Vemurafenib (Zelboraf), Vepesid, Vesanoid, Vidaza, Vinblastine (Velbe), Vincristine, Vincristine, actinomycin D (dactinomycin) and cyclophosphamide (VAC), Vincristine, actinomycin and ifosfamide (VAI), Vincristine, doxorubicin and dexamethasone (VAD), Vindesine (Eldisine), Vinflunine (Javlor), Vinorelbine (Navelbine), Vismodegib (Erivedge), Votrient, XELOX, Xalkori, Xeloda, Xgeva, Xtandi, Yervoy, Yondelis, Z-DEX, Zaltrap, Zanosar, Zavedos, Zelboraf, Zevalin, Zoladex (breast cancer), Zoladex (prostate cancer), Zoledronic acid (Zometa), Zometa, Zomorph, Zydelig, Zytiga, and mixtures thereof.

Experiments of the Disclosure

Background

Referring now to FIG. 1, a schematic diagram showing stages involved in activating and trafficking killer T-cells into a tumor stroma. Stage 1 (①) depicts antigen presentation and T-cell activation. Stage 2 (②) depicts trafficking of activated T-cells through the circulatory system to a tumor stroma. Stage 3 (③) depicts infiltration of the activated T-cells into the tumor stroma from the circulatory system.

Figure 2:
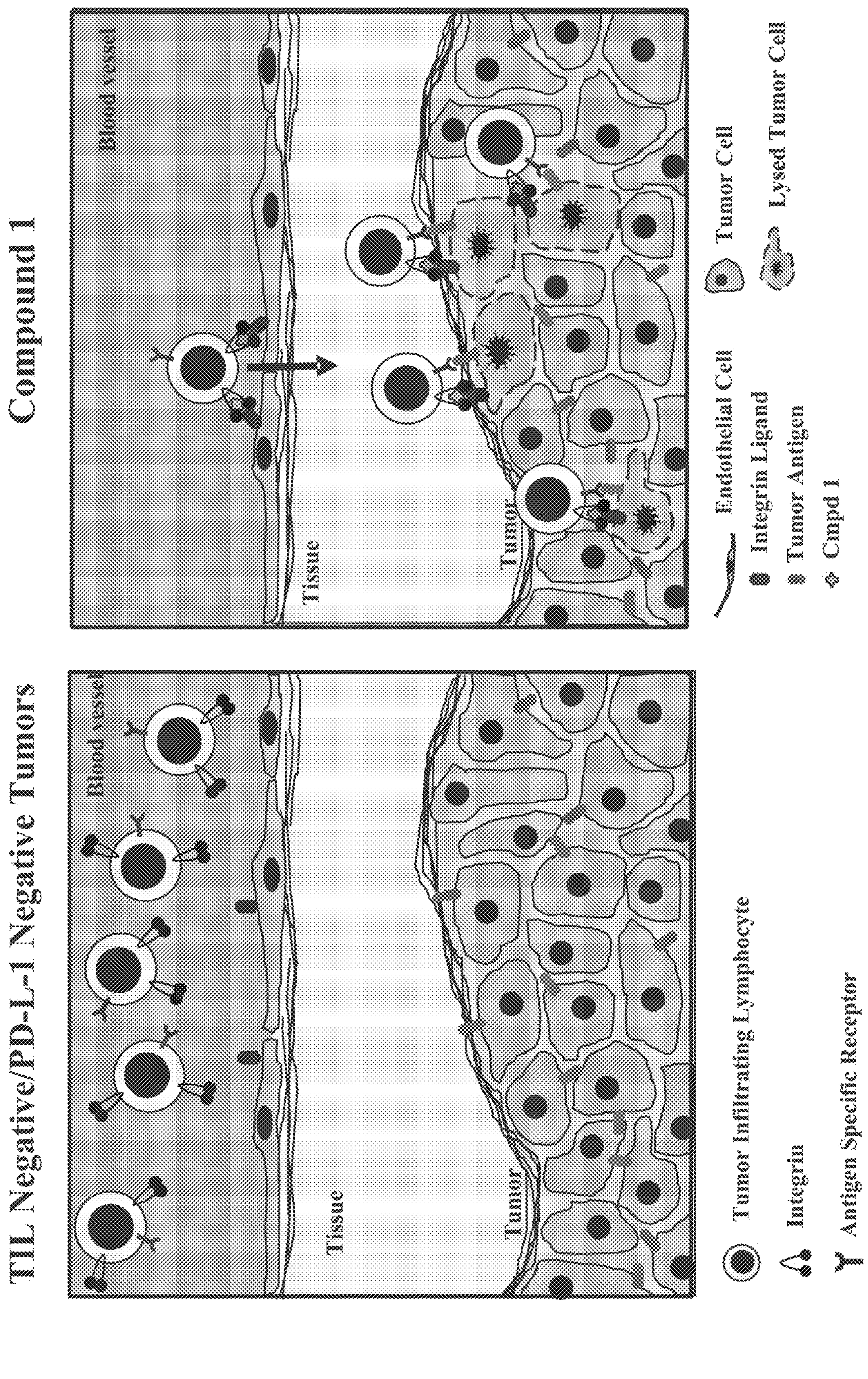
FIG. 2 depicts a schematic diagram of the effective of the effect of the compounds of this invention in conjunction with an anti-CTLA-4 agent.

Referring now to FIG. 2, a schematic diagram showing the activity of T-cells in TIL negative/PDL-1 negative tumors and the activity of T-cells in the presence of a mixture of an anti-CTLA-4 agent and a compound of Formula (I).

Test 1

Figure 3:
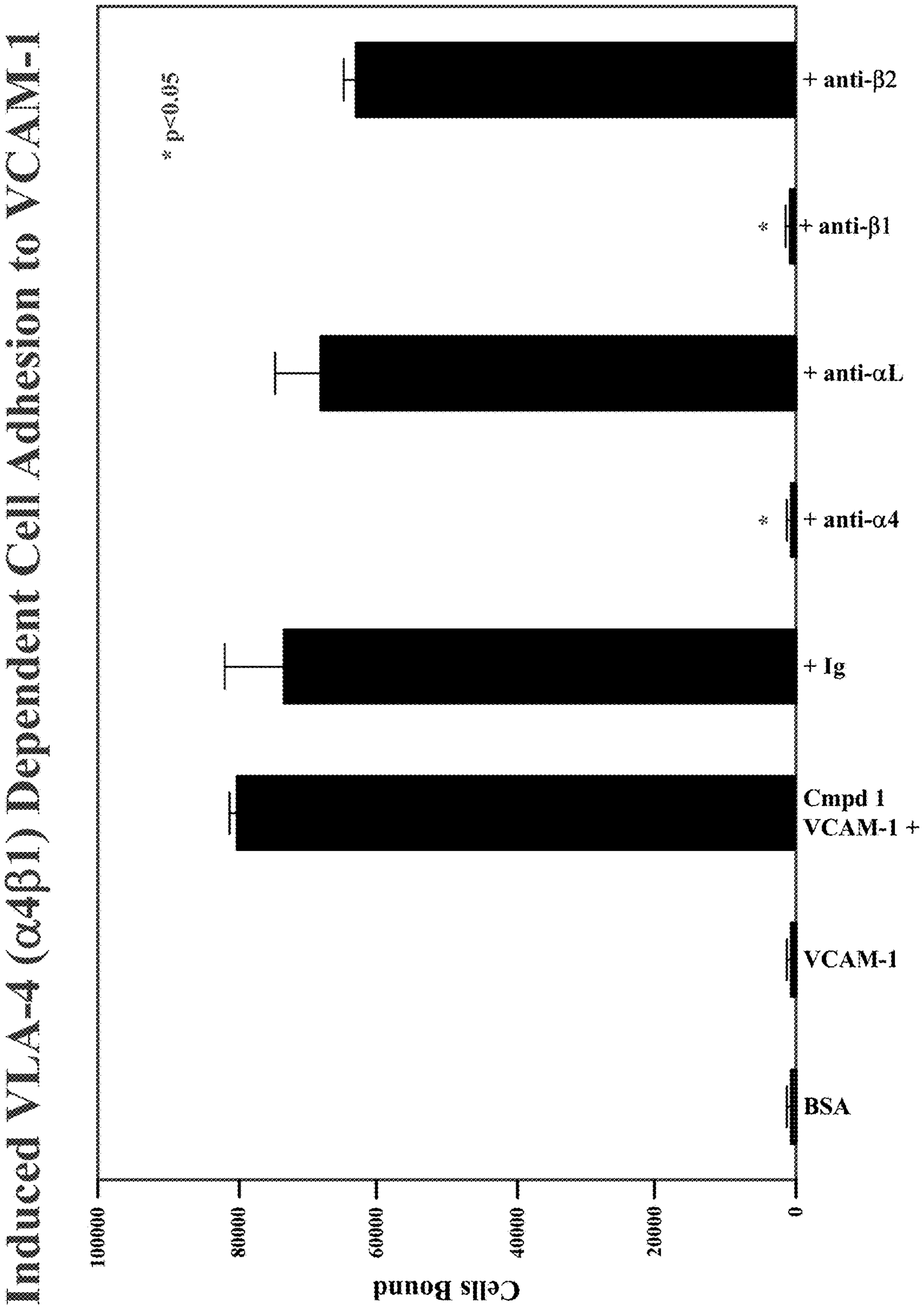
FIG. 3 depicts a histogram of induced VLA-4 (α4β1) Dependent Cell Adhesion to VCAM-1.

Referring now to FIG. 3, a histogram is shown of induced VLA-4 (α4β1) dependent cell adhesion to VCAM-1 in the presence of BSA, VCAM-1, VCAM-1 and a compound of Formula (I) (Cmpd 1), Ig, anti-α4, anti-αL, anti-β1, and anti-β2. The histogram clearly shows that the combination of VCAM-1 and a compound of Formula (I) had the highest bound cells.

Test 2

Figure 4:
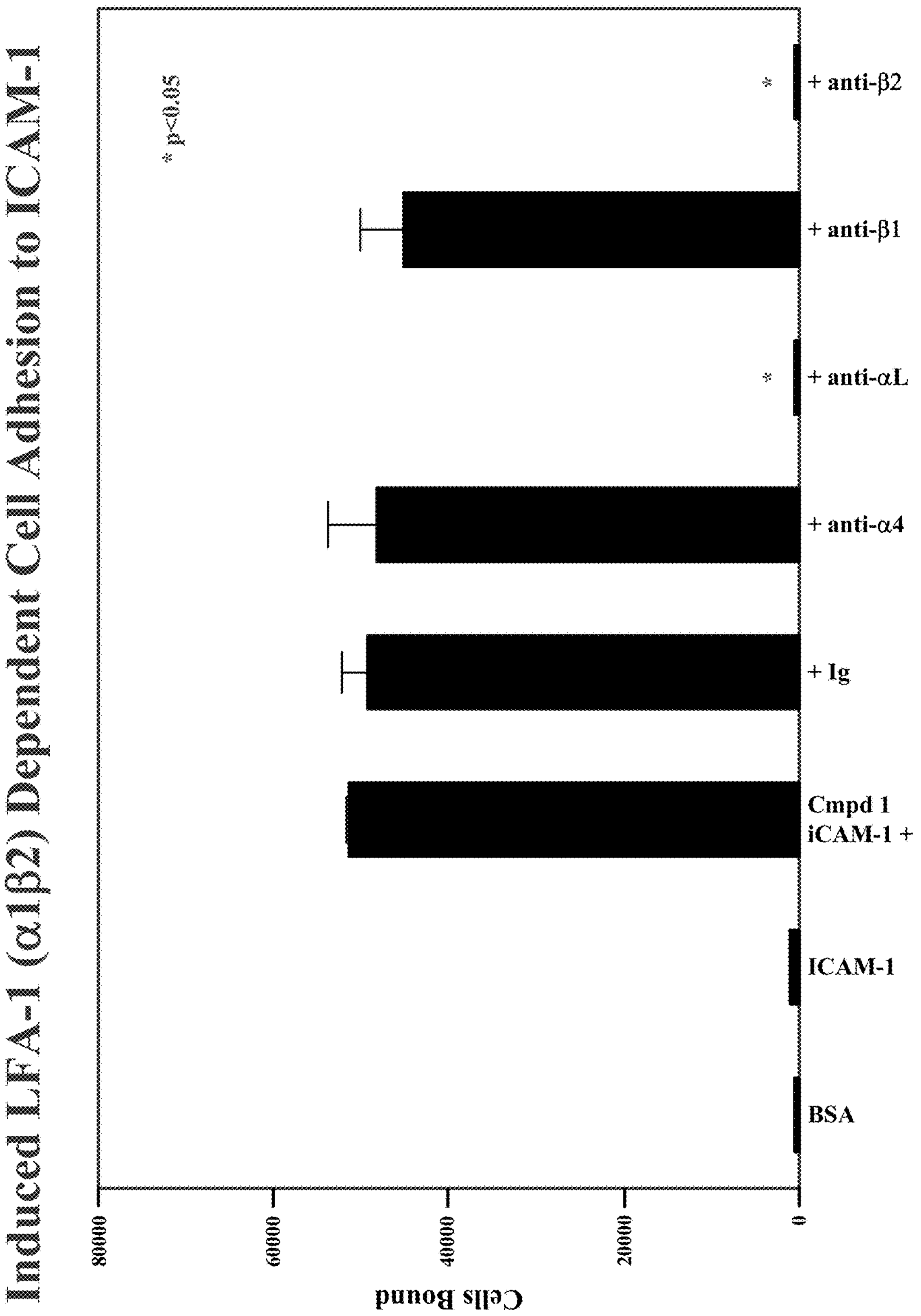
FIG. 4 depicts a histogram of induced LFA-1 (α1β2) Dependent Cell Adhesion to ICAM-1.

Referring now to FIG. 4, a histogram is shown of induced LFA-1 (α1β2) dependent cell adhesion to ICAM-1 in the presence of BSA, ICAM-1, ICAM-1 and a compound of Formula (I) (Cmpd 1), Ig, anti-α4, anti-αL, anti-β1, and anti-β2. The histogram clearly shows that the combination of ICAM-1 and a compound of Formula (I) had the highest bound cells.

Test 3

Figure 5:
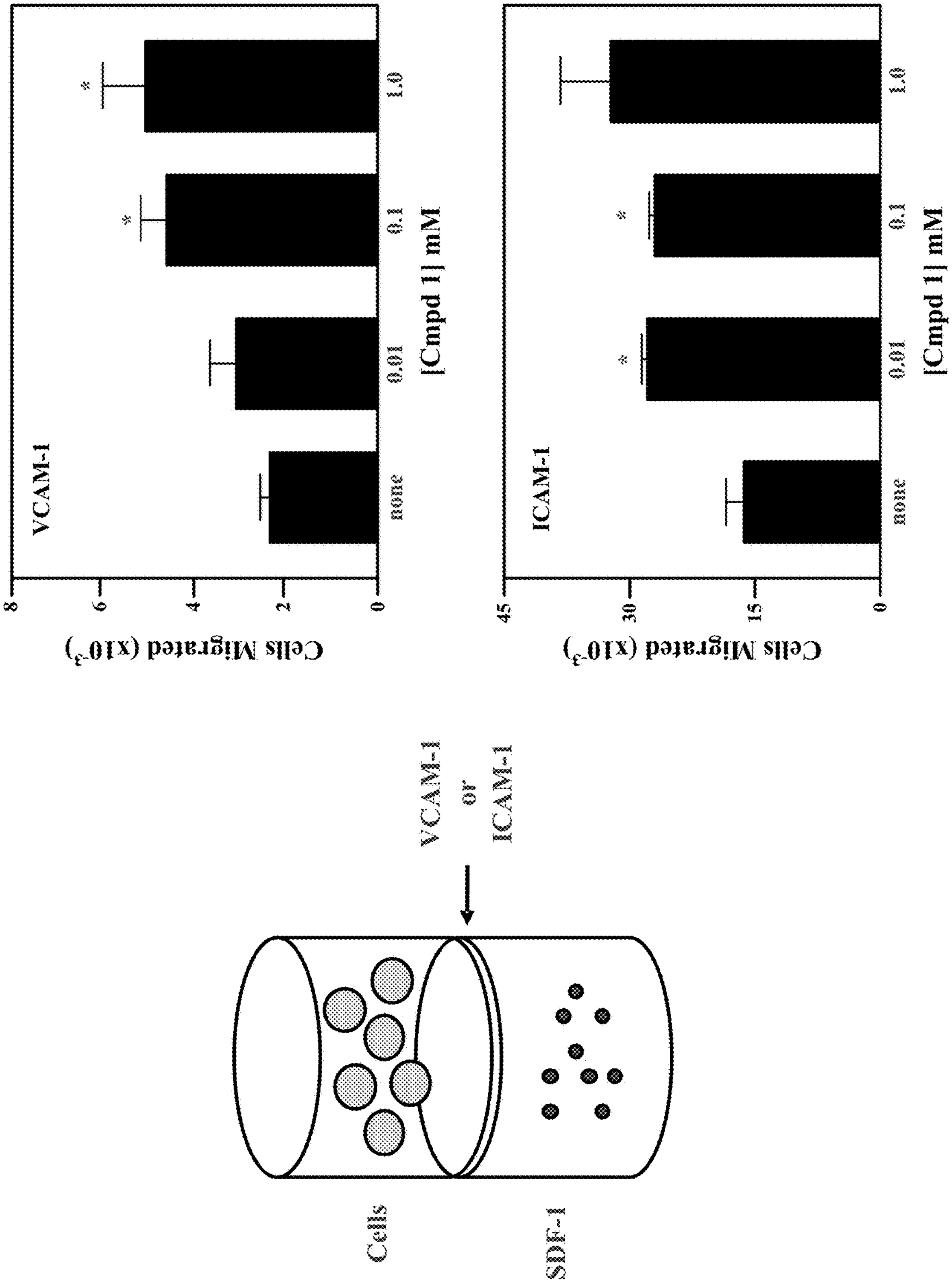
FIG. 5 depicts an apparatus for detecting VCAM-1 and ICAM-1 adhesion and histograms evidencing concentration dependent activation of cells to VCAM-1 and ICAM-1 using a compound of the Formula (I).

Referring now to FIG. 5, an apparatus for testing VCAM-1 and ICAM-1 cell migration, where the cells are initially placed in the top part of the apparatus including a member including VCAM-1 or ICAM-1, with the bottom part of the apparatus initially including SDF-1. Cell migration is then measured from top part to the bottom part for different concentration of CDPD 1, a compound of Formula (I) of VCAM-1 and ICAM-1 impregnated membrane. The plots clearly show a CDPD 1 dependent migration enhancement for both VCAM-1 and ICAM-1.

Test 4

Compound 1, 3-oxo-1-(2-thienyl)-2-(2-thienylmethyl)-4,7,10-trioxa-2-azadodecan-12-yl bis(2-thienylmethyl)carbamate or N,N,N',N'-tetrakis(2-thienylmethyl)-2,5,8,11-tetraoxa-dodecanediamide, a compound of Formula (I) has been tested in the examples set forth below:

Compound 1 was tested for its activity in activating different integrins, especially to determine if the compounds showed collagen and Fibrinogen integrin activity. Activating all integrins is necessary for firm endothelial cell adhesion for extravasation. The results are shown in Table I.

TABLE I

Integrin Selectivity [$EC_{50}$ (μM)*] for Four Compounds of Formula (I)

| CDPD | VLA-4/ VCAM-1 | LFA-1/ ICAM-1 | α4β7/ MAcDAM-1 | α5β1/ Fibronectin | α1b1/ Collagen IV | α2b1/ Collagen I | aiibb3/ Fibrinogen |
|---|---|---|---|---|---|---|---|
| 1 | 11.0 ± 0.5 | 11.0 ± 1.6 | 10.0 ± 2.1 | 7.7 ± 2.3 | Not Active | Not Active | Not Active |

*All assays performed in 50% serum; n = 3; Not active: ≤2 fold increase in adhesion Compound 1, which is a representative compound of Formula (I), shows a unique mechanism of action as VLA-4 and LFA-1 integrin allosteric activators. The present compounds have been found to have unexpectedly anti-tumor activity as single agents when systemically administered alone with a high safety margin. Compound 1 administered orally, as a single agent, or intraperiotoneally once daily for up to 30 days delayed the growth in established CT26 tumors and appeared to increase the density of $CD8^+$ T-cells as indicated by an increase $CD8^+/CD4^+$ ratio. The plasma concentrations associated with such activity were 52.2 nM (32.4 ng/mL) and 105.0 nM (65.2 ng/mL). Even more unexpectedly, Compound 1 had a safety margin (STD 10) greater than (>) 300 times therapeutic exposure and showed no autoimmune toxicity. Compound 1 also showed no adverse clinical symptoms in monkeys at greater than (>) 50 times therapeutic exposure. Compound 1 further showed no clinical symptoms up to about (~) 50 times therapeutic exposure in monkeys.

LIST OF ABBREVIATIONS

The following abbreviations are used in these examples:
ATCC means American type culture collection;
PEG means polyethyleneglycol;
p.o. or PO means per oral;
i.p. or IP means intraperitoneal;
SEM means standard error mean;
TGI means tumor growth inhibition; and
TIL means tumor infiltrating lymphocytes.

Objectives

The following examples are designed to test the anti-tumor efficacy of Compound 1 in a CT26 colon cancer syngeneic tumor model based on three separate studies: Study 1, Study 2, and Study 3.

Materials and Methods

The following examples used these materials from the indicated suppliers:

| Material | Supplier |
|---|---|
| Compound 1 | 7 Hills Pharma/Advinus |
| RPMI-1640 medium | Sigma |
| Foetal Bovine Serum (FBS) | Life Technologies |
| Phosphate Buffer Saline (PBS) | Life Technologies |
| Trypsin-EDTA | Life Technologies |
| Penicillin-streptomycin | Life Technologies |
| Matrigel (Cat # 354234) | Corning |
| Individually ventilated animal cages | Tecniplast, UK |
| Rodent Diet | Nutrilab Rodent Feed, India |
| 1 mL Syringe | BD- Biosciences |

Animals

The experiments were performed using female Balb/c mice obtained from Vivo Bio Tech (Taconic), Hyderabad, India. The animals were housed in individually ventilated cages (maximum 5 animals/cage) with 12 hour dark, 12 hour light conditions. The animals were fed food and water ad libitum. Temperature and relative humidity were maintained at 20±2° C. and 65%, respectively.

Cell Line and Tumor Model

Mouse colon carcinoma CT26 cells were obtained from American Type Culture Collection (ATCC), USA. Cells were grown in RPMI-1640 medium (Sigma, Cat # R6504) supplemented with 10% FBS (Invitrogen, Cat #10438-026), and 1% penicillin streptomycin (Thermo Fisher Scientific, Cat #15140-122). To establish allografts, 1 million CT26 cells were suspended in 50 μL of serum-free medium and mixed at 1:1 ratio with matrigel before implanting subcutaneously into the right flank of mice.

Scale-Up of Tumor Cells

CT26 cells were grown in RPMI-1640 medium (Sigma, Cat # R6504) supplemented with 10% FBS (Invitrogen, Cat #10438-026), and 1% penicillin streptomycin (Thermo Fisher Scientific, Cat #15140-122). The cells were harvested by trypsinization when they reach around 70 to 80% confluence. The cells were re-suspended in serum free medium before inoculating into the animals.

Tumor Cell Inoculation

Prior to inoculation, the skin on the injection site was swabbed with alcohol. To establish allografts, CT26 cells were suspended in serum free medium at a concentration of $(1\times10^6)/50$ μL, mixed with equal volume of matrigel (1:1 ratio) and 100 μL of this mixture was injected to each mouse by subcutaneous implantation using a 1 mL BD syringe attached to a 24 gauge needle.

Randomization

CT26 tumor xenografts were measured after approximately 1 week of cell inoculation when they become palpable. When the average tumor volume reaches around 110 $mm^3$, animals were randomized into treatment groups group maintaining the average tumor volume of each group similar across groups for Study 1 and Study 2. In Study 3, the animals were randomized on the basis of body weights +1 day post cell implantation.

Animal Management

The facility where the experimentation was carried out is AAALAC (Association for Assessment and Accreditation of Lab Animal Care International) accredited.

Test System

| | |
|---|---|
| Species | Mouse (*Mus musculus*) |
| Strain | Balb/c |
| Gender | Female |
| Source | Taconic |
| Number of Animals per Group | 10 to 20 (Across 3 different studies) |
| Body Weight at Start of Treatment | ~18 g |
| Age of Animals at Start of Treatment | 6-9 weeks |

Health Status

On arrival, all animals were examined in detail for their general health condition and body weight measurement was noted down. These mice will also be screened free for infections.

Housing

The animals were housed in groups of six in individually ventilated cages in quarantine area for a week. Healthy animals were selected and transported into the study room. Each cage was clearly labeled with the following information on a cage card: Project/Study number; Group, Animal strain; and Gender; Prescribed dose concentration; Route of administration and Dose volume of Test items administered.

Identification

Each animal was numbered and identified by ear punching.

Room Environment

The animals were kept in a controlled environment (targeted ranges: temperature 22±2° C., humidity 60±2%, 60 air changes per hour), with a 12 hour light/dark cycle, and under barrier (quarantine) conditions. Temperature and relative humidity was monitored continuously. Entire facility was routinely monitored for any air-borne infections.

Diet and Water

Animals were given an autoclaved commercial diet (Nutrilab Rodent Feed, cylindrical shaped pellets) and autoclaved water ad libitum.

Animal Delivery and Acclimation

Two weeks prior to initiating the study, animals were delivered to study sight. Animals were quarantined for a week upon arrival prior to releasing them for the study.

Animal Care Compliance

Procedures involving the care and use of animals in the study was reviewed and approved by the Institutional Animal Care and Use Committee (IAEC/JDC/2017-120) prior to conduct. During the study, the care and use of animals was in accordance with the principles outlined in the Guide for the Care and Use of Laboratory Animals, $8^{th}$ Edition, 2010 (National Research Council).

In-Life Observation and Measurements

Data Acquisition

Each animal's number was recorded manually by checking the ear marking. All tumor measurements were acquired with digital calipers (Mitutoyo).

Mortality

Mortality checks were performed daily during the study.

Clinical Observations

Animals were monitored for clinical signs (such as illness and behavioral changes) daily throughout the study.

Body Weights

Body weights were recorded on days 0 (animal randomization based on tumor volume) and thrice weekly thereafter until study termination.

Tumor Measurements

Tumor dimensions (length and breadth) were measured on days 0 (animal randomization based on tumor volume) and thrice weekly thereafter until study termination. Tumor volumes were calculated using the formula $(b^2*l)*0.52$ where l=length, b=breadth (Dusan Djokovic et al., BMC Cancer, 2010, 10:641). Tumor growth inhibition was calculated after normalizing the tumor volume on a given day to that on day 1.

Isolation and Analysis of Tumor Infiltrating Lymphocytes (TILs) by FACS

On day 19 of treatment initiation tumors were isolated from study mice aseptically (n=5/group).

Tumor (TILs)

Tumor tissue was minced devoid of dead and necrotic tissue was mechanically disaggregated aseptically in RPMI medium without proteolytic enzymes in gentleMACS C-tubes using gentleMACS Octo Dissociator under the program 37C_m_TDK_1_30m (Miltenyi Biotec). Cell suspension was enriched for single cells by filtering the disaggregated mix through 70 μm cell strainer. Cells were pelleted at 300 g for 7 min at 4° C., washed twice with fresh complete media followed by FACS buffer containing PBS w/o calcium and magnesium (pH 7.4), 2% FBS and 0.05% sodium azide. Note: Proteolytic enzymes may chew up the antigen epitopes, therefore enzymatic dissociation is not performed.

Cytotoxic T-Cells ($CD3^+$ $CD8^+$) and Activated T-Cells ($CD3^+$ $CD4^+$)

Five million total viable cells were used as input for staining with the following fluorochrome conjugated antibodies for 30 min on ice in dark. Unbound stain was removed by washing cells in FACS buffer twice. The results

TABLE II

Antibody Protocol

| Antibody-Fluorochrome Direct Conjugates | Antibody Clone | Antibody Concentration | Source |
|---|---|---|---|
| CD3e - PE (Rat Anti-Mouse) | 145-2C11 | 2.5 μg/test | BD |
| CD4 - FITC (Rat Anti-Mouse) | RM4-5 | 2.0 μg/test | BD |
| CD8a - APC (Rat Anti-Mouse) | 53-6.7 | 2.5 μg/test | BD |

Unstained cells were used for setting up gates and focus single cells using INSPIRE acquisition software in Amnis FlowSight flow cytometer (Amnis Corporation, Seattle, WA) with 405, 488, 642 nm excitation lasers. Bright field signals were collected in channel 1 and 9, FITC in channel 2, PE in channel 3, 7AAD (dead cell marker) in channel 4, and APC in channel 11. R1 gate (frequency vs. gradient RMS or bright field) was used to collect focused cells; R2 gate (area vs. channel 4 intensity scatter plot) was used to collect viable cells; and R3 gate (area vs. aspect ratio) was used to collect singlets. A total of 50,000 events were collected/sample with a maximum limit of raw pixel intensity of 4094 to eliminate saturating signals. Hierarchical gating strategy was created following compensation using single color controls and data analysis performed in IDEAS cell analysis software for identifying cells of interest.

Before proceeding for FACS acquisition, we have recorded the total viable cell yield for each tumor sample. For the FACS acquisition, we have taken 5 million cell input per tumor sample across all samples for staining with antibodies. After stained cells acquired in FACS, single cells (in $R^2$ gate) were further gated for 7AAD negative viable cells to obtain percent viability. From the CD3 positive population gated out of viable 7AAD-ve population, the percentage of viable cells displaying CD3 positive signal was recorded using the statistics option in FACS software. Based on 5 million cell input and the percent viability, we have computed the yield of CD3 positive viable cells per 5 million cell input. Similarly, the percentage of viable cells displaying CD4 or CD8 positive signals was obtained using specific cell gating created out of CD3 positive gate. By knowing the CD3 positive viable cell yield and the percentage of CD3+CD4+ or CD3+CD8+, a total yield of viable CD3+CD4+ or CD3+CD8+ was computed for the 5 million cell input. Based on this information, yield per million cells was calculated and reported in results.

Termination Policy for Individual Animals

Treatment of animals at any dose levels was terminated and animals euthanized if animals are found moribund with severe clinical signs or more than 20% drop in body weight or tumor volume exceeding 2500 $mm^3$.

TABLE III

Study 1 Design

| Group | Treatments | Mice/group |
|---|---|---|
| 1 | Untreated control | 10 |
| 2 | Compound 1 (20 mg/kg PO QD) | 10 |
| 3 | Compound 1 (1 mg/kg IP QD) | 10 |

Rationale for Dose and Schedule

The 1 mg/kg, IP QD for 30 days is based synergistic studies in combination with CTLA-4 conducted by the sponsor. The effective oral dose and schedule Compound 1 is unknown.

TABLE IV

IP and PO Vehicles

| Route | Vehicle | Dose (mg/kg) | C (mg/mL) | V (mL) |
|---|---|---|---|---|
| IP | 17% Tween 80 + 16% | 1 | 0.4 | 75 |
| | glycerol + PBS pH 7.4 Q.s | 0 | 0 | 75 |
| PO | 50% Corn oil + 40% PEG | 10 | 2 | 75 |
| | 400 + 10% Cremophor EL | 20 | 4 | 75 |
| | | 0 | 0 | 75 |

Dosing volume for IP and oral formulations: 2.5 mL/kg and 5 mL/kg, respectively.

TABLE V

Study 2 Design

| Group | Treatment | Route, Dosing Frequency | Dose | Mice/Group |
|---|---|---|---|---|
| 2 | vehicle control | IP QD | 2.5 mL/kg | 12 |
| 3 | Compound 1 | IP QD | 1 mg/kg | 12 |

TABLE VI

Study 3 Design

| Group | Treatments | Route Dosing Frequency | Dose | Mice/Group |
|---|---|---|---|---|
| 1 | Vehicle control | | 2.5 mL/kg | 20 |
| 2 | Compound 1 | IP QD | 1 mg/kg | 20 |
| 3 | Compound 1 | IP BID | 1 mg/kg | 20 |

Data Analysis and Statistical Evaluation

Mean body weight loss and percent changes were calculated for each group. Similarly, mean tumor volume and percent tumor growth inhibition were calculated. The percent tumor growth inhibition (% TGI) as a function of anti-tumor efficacy were computed with respect to untreated vehicle control by comparing to the tumor volumes of day 1 using formula described below:

$$\% \text{ TGI}=[1-(\text{Treatment } TV_{Final}-\text{Treatment } TV_{Initial})/(\text{Control } TV_{Final}-\text{Control } TV_{Initial})]*100$$

Changes in percent body weight (BW) were calculated according to the formula below:

$$\% \text{ Change BW}=(BW_{Final}-BW_{Initial})/(BW_{Initial})*100$$

All statistical calculations were performed using Prism 5.0 (GraphPad Software Inc, USA). Comparisons of tumor size and animals weight measurements during and at the termination of the study were made between the treatment groups and respective vehicle control groups by two-way ANOVA, followed by Bonferroni's multiple comparison tests. A p value less than 0.05 were considered significant.

In Vivo Efficacy

Study 1

The test agent, Compound 1 was evaluated in CT26 syngeneic tumor model in Balb/c mice. Compound 1 was administered in mice when the starting tumor volume reached 109±7.1 $mm^3$ eight days after implantation of CT26 cells. Two dosage regimens were tested: Compound 1 PO QD (20 mg/kg) or Compound 1 IP QD (1 mg/kg) that accounted for a significant 36.2% ($p<0.01$) and 55.4% ($p<0.0001$) inhibition in tumor volume (TGI), respectively on day 13. Compound 1 administration by intraperitoneal route at 1 mg/kg dose resulted in a higher TGI compared to administration by oral route at 20 mg/kg. Administration of Compound 1 through both, oral and intraperitoneal routes was well tolerated in term of body weights of animals.

Study 2

The test agent, Compound 1 was evaluated in CT26 syngeneic tumor model in Balb/c mice. Compound 1 was administered in mice when the starting tumor volume reached 110±6.9 $mm^3$ seven days after implantation of CT26 cells. Compound 1 was administered through i.p. route at 1 mg/kg body weight that accounted for a significant 46.0% ($p<0.0001$) inhibition in tumor volume (TGI) on day 13.

Study 3

The test agent, Compound 1 was evaluated in CT26 syngeneic tumor model in Balb/c mice. Compound 1 was administered in mice +1 day after CT26 cell implantation. Tumors were not measurable at this time, however, tumors became palpable on day 7 and tumors were measured from that point. Two dosage regimens were tested: Compound 1 IP QD (1 mg/kg) or Compound 1 IP BID (1 mg/kg) that accounted for a significant 46.1% ($p<0.05$) and 57.6% ($p<0.01$) inhibition in tumor volume (TGI), respectively on day 14.

In addition, tumors were allowed to grow up to day 18 with continued Compound 1 dose, that decreased tumor growth resulting in a significant inhibition $p<0.01$ in the q.d. group compared to $p<0.0001$ in BID group. However, the IP BID treatment regimen had given a slightly better (not significant) efficacy in compare to IP QD treatment regimen. On day 19, animals were sacrificed to obtain tumor grafts. Upon non-enzymatic dissociation, cell viability was assessed and subjected to enumeration of $CD3^+$, $CD4^+$ or $CD8^+$ tumor infiltrating T-cells (detailed method, refer section 11). In response to treatment, there was a decreased trend in $CD3^+$ and $CD4^+$ double positive cells compared to Compound 1 vehicle control. Interestingly, this trend was opposite for $CD3^+$ and $CD8^+$ double positive T-cells. The net effect in a progressive increase in the ratio of $CD8^+/CD4^+$ T-cells in tumors was observed in response to treatment. A significant increase in the ratio of $CD8^+/CD4^+$ T-cells was obtained for Compound 1 QD+ PD-1 antibody combination treatment ($p<0.05$). In conclusion, our data indicate that Compound 1 has a single agent activity, such antitumor activity may be due increased infiltration of cytolytic T cells and an enhancement of this effect when co-treated with anti PD-1 antibody.

In this model whether the study started in established tumor or non-established tumor, the test agent had given a comparable results across all three independent studies. And it was found that Compound 1 at a dose of 1 mg/kg was most efficacious dose when it was administered in IP route. In conclusion, our data indicate that Compound 1 has a single agent activity, such antitumor activity may be due increased infiltration of cytolytic T cells and an enhancement of this effect when co-treated with anti PD-1 antibody.

The results of the three Studies 1-3, are set forth below.

TABLE VII

Study 1 - Average Tumor Volume ($mm^3$)

| Treatment | % Tumor Growth Inhibition Day 4 | 6 | 8 | 11 | 13 |
|---|---|---|---|---|---|
| Compound 1 (20 mg/kg PO QD at 4 h) | −6.1 | 16.5 | 38.2 | 42.2 | 36.2 |
| Compound 1 (1 mg/kg IP QD at 4 h) | 36.1 | 41.4 | 61.5 | 64.4 | 55.4 |

Figure 6:
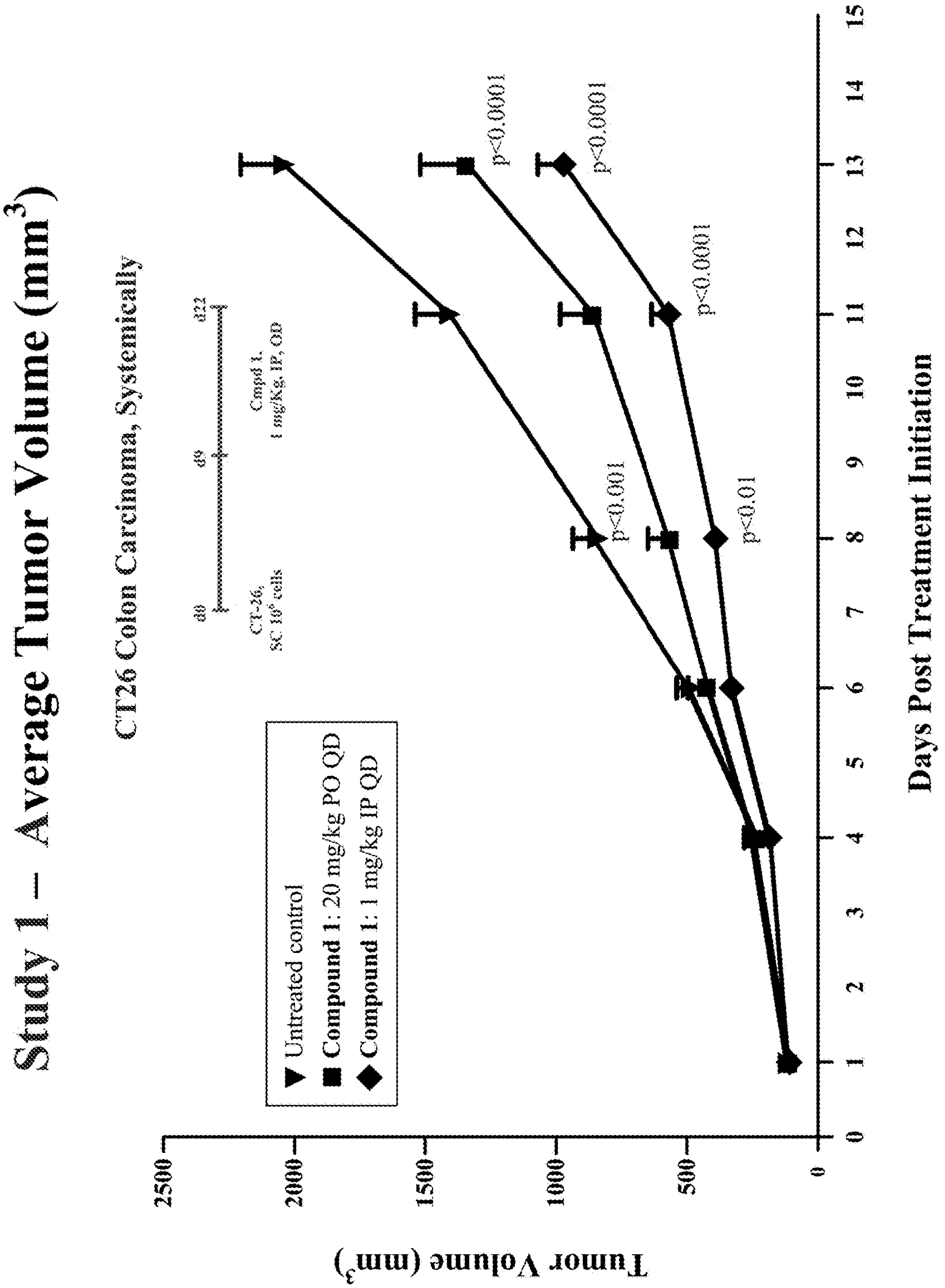
FIG. 6 depicts Study 1 plots of average tumor volumes ($mm^3$) in mice after different days of treatment of Compound 1 administered via PO route or IP route.

Referring now to FIG. 6, average tumor volume ($mm^3$) in mice after different days of treatment of Compound 1 administered via PO route or IP route.

TABLE VIII

Study 2 - Average Tumor Volume ($mm^3$)

| Group | Treatment | | Average Tumor Volume ($mm^3$) Day 1 | 2 | 4 | 6 | 8 | 10 | 13 |
|---|---|---|---|---|---|---|---|---|---|
| 1 | Vehicle Control | Mean | 111 | 167 | 310 | 491 | 746 | 1063 | 1828 |
| | | SEM | 7 | 13 | 28 | 51 | 57 | 93 | 150 |
| 2 | Compound 1 | Mean | 111 | 171 | 244 | 343 | 545 | 744* | 1038‡ |
| | (1 mg/kg IP QD) | SEM | 7 | 15 | 31 | 51 | 93 | 112 | 165 |

TABLE IX

| Study 2 - Average Tumor Volume ($mm^3$) | | | | | | |
|---|---|---|---|---|---|---|
| | % Tumor Growth Inhibition Day | | | | | |
| Treatment | 2 | 4 | 6 | 8 | 10 | 13 |
| Compound 1 (1 mg/kg IP QD at 4 h) | −6.6 | 33.0 | 38.9 | 31.6 | 33.5 | 46.0 |

Figure 7:
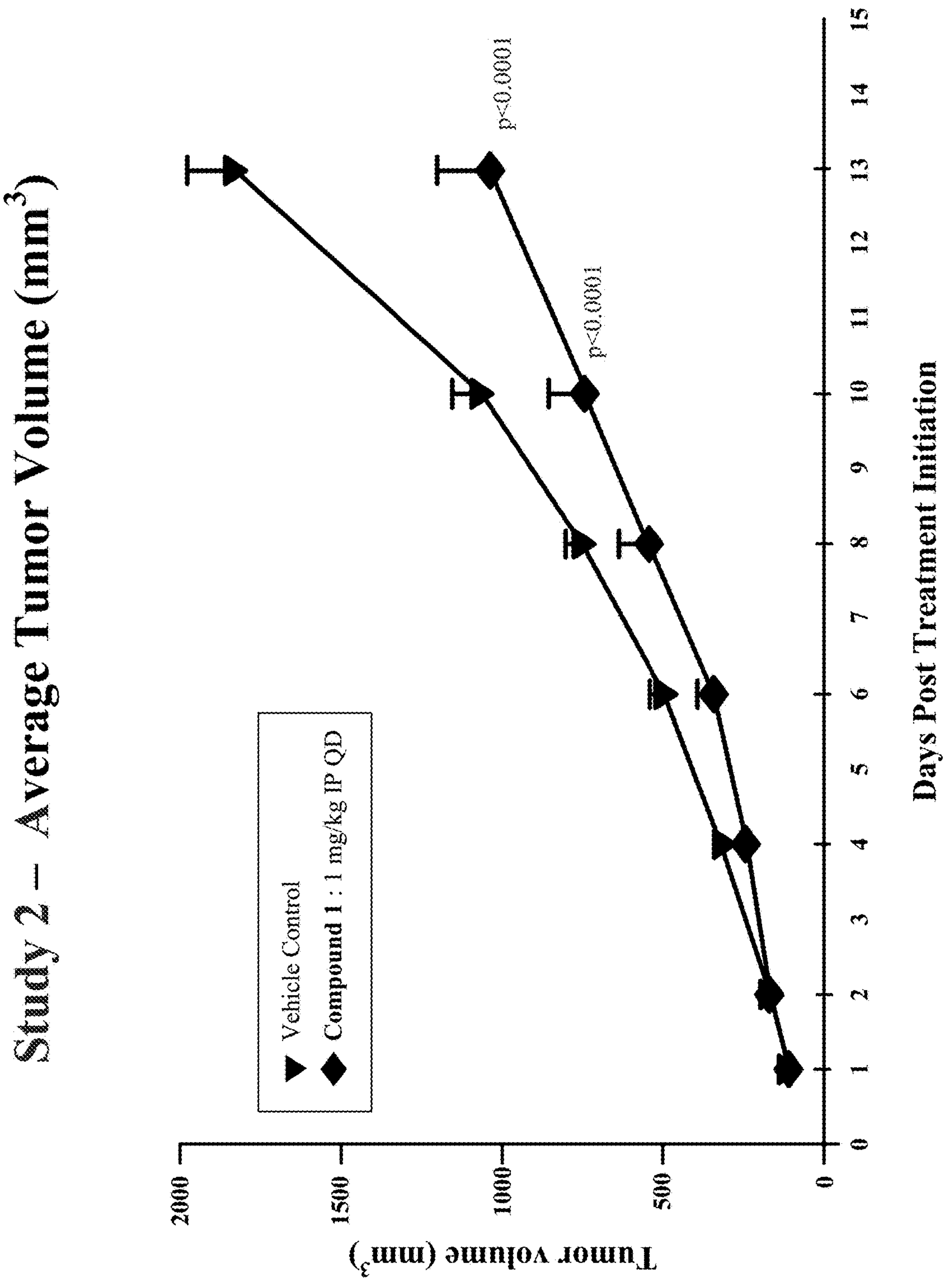
FIG. 7 depicts Study 2 plots of average tumor volume ($mm^3$) in mice after different days of treatment initiation. Compound 1 was administered via the IP route.

Referring now to FIG. 7, average tumor volume ($mm^3$) in mice after different days of treatment initiation. Compound 1 was administered via the IP route.

TABLE X

| Study 3 - Average Tumor Volume ($mm^3$) | | | | | | | | | |
|---|---|---|---|---|---|---|---|---|---|
| | | | Average Tumor Volume ($mm^3$) Day | | | | | | |
| Group | Treatment | | 7 | 10 | 12 | 14 | 16 | 18 |
| 1 | Vehicle Control | Mean | 97 | 270 | 443 | 689 | 896 | 1130 |
| | | SEM | 6 | 24 | 59 | 104 | 138 | 114 |
| 2 | Compound 1 (1 mg/kg IP QD) | Mean | 96 | 193 | 312 | 415† | 566†† | 768‡ |
| | | SEM | 6 | 19 | 30 | 47 | 66 | 69 |
| 3 | Compound 1 (1 mg/kg BID) | Mean | 91 | 159 | 269 | 342‡ | 512‡‡ | 689‡‡ |
| | | SEM | 6 | 12 | 22 | 46 | 75 | 83 |

†$p < 0.05$ compared to Group 1;
††$p < 0.01$ compared to Group 1;
‡$p < 0.0001$ compared to Group 1;
‡‡$p < 0.0001$ compared to Group 1

Figure 8:
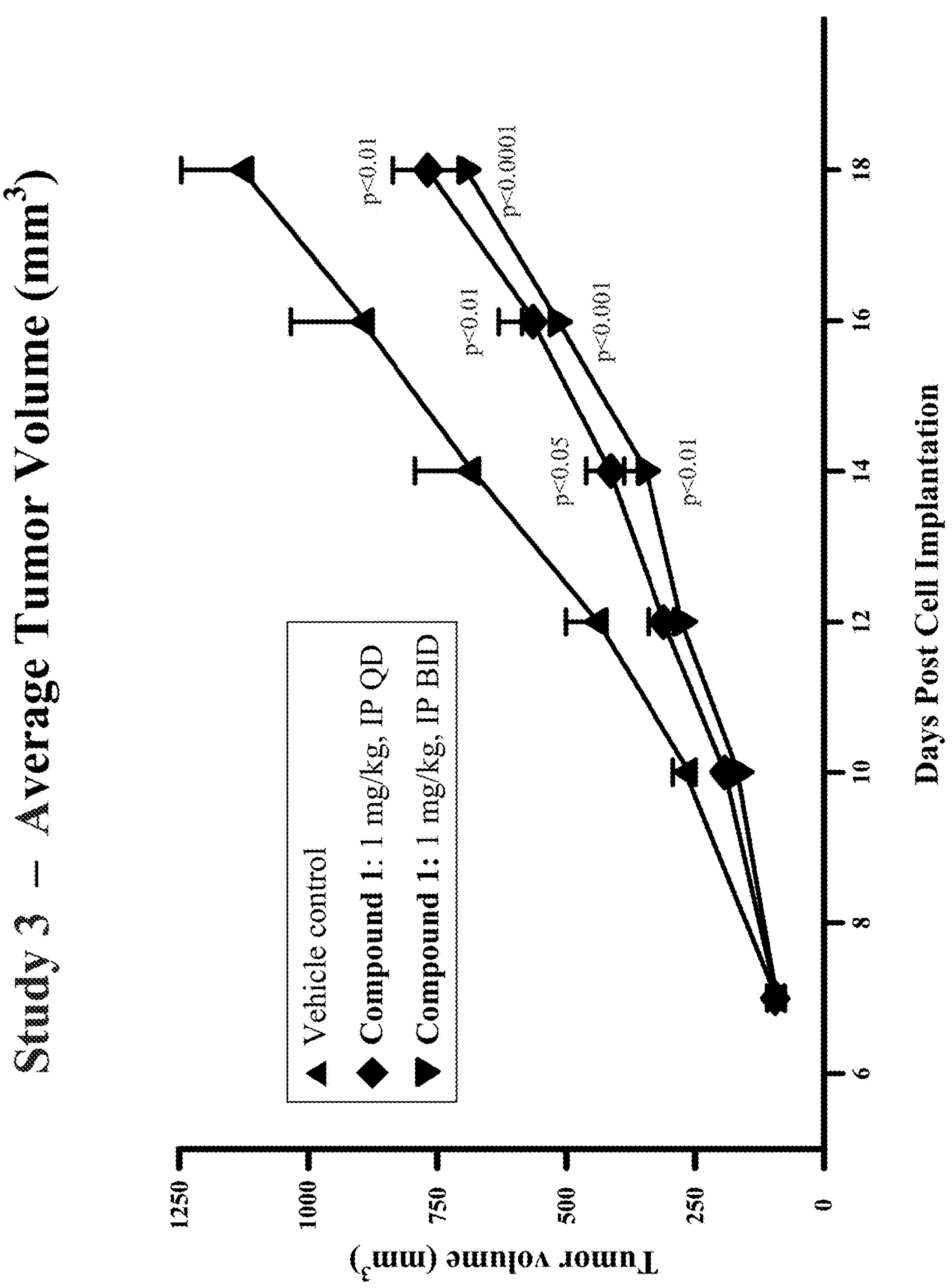
FIG. 8 depicts Study 3 plots of average tumor volume ($mm^3$) in mice after different days of treatment initiation. Compound 1 was administered in once QD route or twice BID route daily.

Referring now to FIG. 8, average tumor volume ($mm^3$) in mice after different days of treatment initiation. Compound 1 was administered in once QD route or twice BID route daily.

Figure 9:
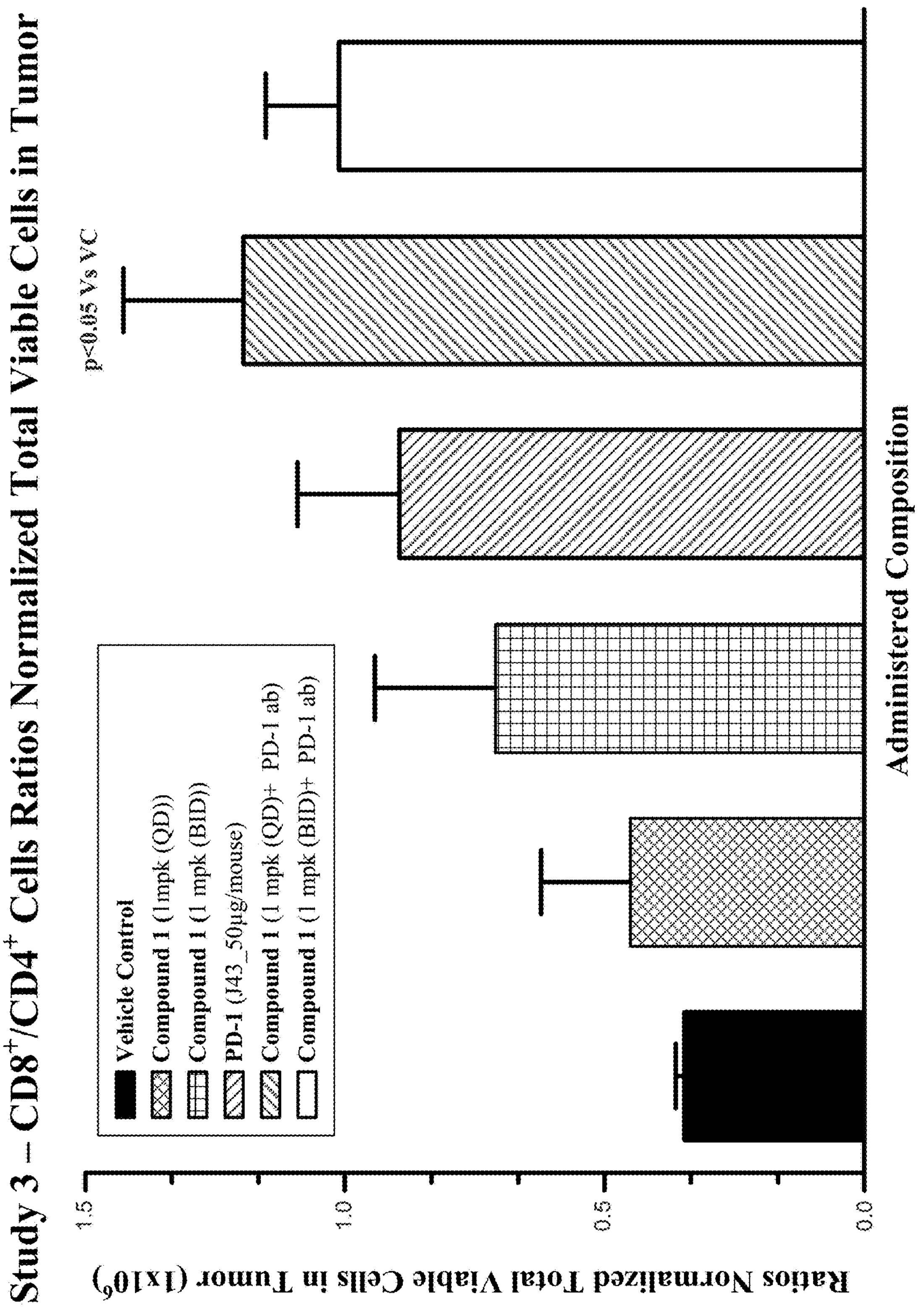
FIG. 9 depicts bar charts of ratios of $CD8^+$ to $CD4^+$ cells normalized to per million total viable cells in tumor after treatment.

Referring now to FIG. 9, ratios of $CD8^+$ to $CD4^+$ cells normalized to per million total viable cells in tumor after treatment.

The above data clearly shows that the compounds of Formula (I) for single agent anti-cancer activity when administered systemically, and especially orally, along with the ability for these compounds to synergistically interact with other anti-cancer agents to treat solid tumor cancers, promote immune response to the tumors, and to turn "cold" solid tumors (solid tumors having low infiltration propensity by T-cells) to "hot" tumor (solid tumors having high infiltration propensity by T-cells), i.e., reducing cancer growth and/or reducing the actual size of the tumor.

CLOSING PARAGRAPH OF THE DISCLOSURE

All references cited herein are incorporated by reference. Although the disclosure has been disclosed with reference to aspects and specific embodiments of the disclosure, from reading this description those of skill in the art may appreciate changes and modification that may be made which do not depart from the scope and spirit of the disclosure as described above and claimed hereafter.

I claim:

1. A method comprising:

administering an antitumor pharmaceutical composition comprising an effective amount of one or more integrin activators comprising one or more N,N-disubstituted amide compounds, N,N-disubstituted carbamate compounds, N,N-disubstituted urea compounds, N,N-disubstituted sulfonamide compounds, or combinations thereof to an animal or human, wherein the effective amount is sufficient to produce a plasma concentration of the one or more integrin activators in the animal or human of between about 1 nano molar (nM) and about 100 nM, wherein the effective amount is also sufficient for: (a) prompting an immune response to antigens from a solid tumor, (b) priming and activating antigen presenting cells and T-cells, (c) trafficking natural T-cells and the activated T-cells into the solid tumor, (d) prompting the infiltration of the nature T-cells and activated T-cells into the solid tumor and; the recognition of cancer cells in the solid tumor by the natural T-cells and the activated T-cells, and (e) prompting the killing of the cancer cells in the solid tumor via the natural T-cells and the activated T-cells resulting in a reduction in a size of the solid tumor, wherein the one or more integrin activators target integrins including α4β1, α4β7, α5β1, αLβ2, αVβ3, or combinations thereof, and the one or more integrin activators improve binding interactions between the integrins and their respective ligands including VCAM-1, fibronectin, MAdCAM-1, ICAM-1, ICAM-2, vitronectin, or combinations thereof.

2. The method of claim 1, further comprising:

administering one or more anticancer agents, wherein the one or more anticancer agents: (a) activate an anti-tumor immune T cell response; (b) prevent immune suppression by targeting inhibitory receptors including PD-1, CTLA-4, LAG-3, TIM-3, BLTA, or combinations thereof; (c) inhibit myeloid derived suppressor cells, tumor associated macrophages, regulatory T cells, or combinations thereof; or (d) any combination thereof.

3. The method of claim 1, wherein the administering of the pharmaceutical composition occurs over 30 days.

4. The method of claim 1, wherein the administering of the pharmaceutical composition occurs over 18 days.

5. The method of claim 1, wherein the administering of the pharmaceutical composition occurs over 13 days.

6. The method of claim 1, wherein, in the administering step, the plasma concentration is between about 25 nM and about 100 nM after each administration.

7. The method of claim 1, wherein, in administering step, the plasma concentration is between about 50 nM and about 100 nM after each administration.

8. The method of claim 1, wherein, in the administering step, the plasma concentration is between about 25 nM and about 75 nM after each administration.

9. The method of claim 1, wherein, in the administering step, the plasma concentration is between about 50 nM and about 75 nM after each administration.

10. The method of claim 1, wherein the administering comprises oral administering or intraperiotoneal administering.

11. The method of claim 1, wherein, in the administering step, the one or more N,N-disubstituted amide compounds, N,N-disubstituted carbamate compounds, N,N-disubstituted urea compounds, N,N-disubstituted sulfonamide compounds, or combinations thereof comprise one or more compounds of the general Formula (I):

$$R^1\text{-}M^1\text{-}N(R^2)\text{-}M^2\text{-}M^3\text{-}M^4\text{-}M^5\text{-}M^6\text{-}R^3 \quad (I)$$

wherein:

$R^1$ comprises alkyl, aryl, aralkyl, cycloalkyl, cycloalkylalkyl, haloalkyl, heterocylcyl, or heterocyclylalkyl, $R^2$ comprises alkyl, aryl, aralkyl, cycloalkyl, cycloalkylalkyl, haloalkyl, heterocylcyl, or heterocyclylalkyl, $M^1$ comprises $CH_2$, CO, $SO_2$, or $(CR^4R^5)_l$, $M^2$ is absent or comprises $CH_2$, CO, $SO_2$, or $(CR^4R)_l$, $M^3$ is absent or comprises $CH_2$, O, S, $NR^6$, or $(CR^7R^8)_m$, $M^4$ is absent or comprises $CH_2$, or $(CR^9R^{10})_n$, $M^5$ is absent or comprises O,$(CR^{11}R^{12})$, or $(CR^{11}R^{12})_p$, $M^6$ comprises $(CH_2)_q$, $(CH_2)_q$—CH═CH—$(CH_2)_r$, $(CH_2)_q$-arylene-$(CH_2)_r$, $(CH_2CH_2O)_q$, or $NR^{34}(CH_2)_q$, $R^3$ comprises hydrogen, alkyl, aryl, aralkyl, aryloxyalkyl, alkoxyalkyl, cycloalkyl, cycloalkylalkyl, hydroxyl, hydroxyalkyl, heterocyclyl, guanadino, $CONR^{13}R^{14}$, $NR^{15}COOR^{16}$, $NR^{15}COR^{16}$, $NR^{15}CONR^{13}R^{14}$, $NR^{15}SO_2R^{16}$, $OCOR^{16}$, $COOR^{16}$, $OR^{16}$, or $SR^{16}$, $R^4$, when present, comprises hydrogen, lower alkyl, or aralkyl, $R^5$, when present, comprises hydrogen, lower alkyl, or aralkyl, $R^6$, when present, comprises hydrogen, lower alkyl, or aralkyl, $R^7$, when present, comprises hydrogen, lower alkyl, or aralkyl, $R^8$, when present, comprises hydrogen, lower alkyl, or aralkyl, $R^9$, when present, comprises hydrogen, lower alkyl, or aralkyl, $R^{10}$, when present, comprises hydrogen, lower alkyl, or aralkyl, $R^{11}$, when present, comprises hydrogen, lower alkyl, or aralkyl, $R^{12}$, when present, comprises hydrogen, $NR^{21}CONR^{22}R^{23}$, $NR^{21}COR^{24}$, $NR^{21}SO_2R^{24}$, $NR^{21}COOR^{24}$, $OCOR^{24}$, $OR^{24}$, $O(CH_2CH_2O)_sR^{24}$, $COOR^{24}$, alkyl, and hydroxyalkyl, $R^{13}$, when present, is hydrogen, alkyl, aryl, aralkyl, cycloalkyl, cycloalkylalkyl, haloalkyl, heterocyclyl, heterocyclylalkyl, alkoxycarbonyl, or alkoxycarbonylalkyl, $R^{14}$, when present, is hydrogen, alkyl, aryl, aralkyl, cycloalkyl, cycloalkylalkyl, haloalkyl, heterocyclyl, heterocyclylalkyl, alkoxycarbonyl, or alkoxycarbonylalkyl, $R^{15}$, when present, is hydrogen, alkyl, aryl, aralkyl, cycloalkyl, cycloalkylalkyl, heterocyclyl, or heterocyclylalkyl, $R^{16}$, when present, comprises hydrogen, alkyl, aryl, aralkyl, cycloalkyl, cycloalkylalkyl, haloalkyl, heterocyclyl, heterocyclylalkyl, alkoxycarbonyl, or alkoxycarbonylalkyl, $R^{21}$, when present comprises is hydrogen, lower alkyl, or aralkyl, $R^{22}$, when present, comprises alkyl, aryl, aralkyl, cycloalkyl, cycloalkylalkyl, haloalkyl, heterocyclyl, heterocyclylalkyl, alkoxycarbonyl, alkoxycarbonylalkyl, $R^{23}$, when present, comprises hydrogen, alkyl, aryl, cycloalkyl, cycloalkylalkyl, heterocyclyl, heterocyclylalkyl, or aralkyl, $R^{24}$, when present, comprises hydrogen, alkyl, aryl, aralkyl, cycloalkyl, cycloalkylalkyl, heterocyclyl, heterocyclylalkyl, haloalkyl, alkoxycarbonyl, or alkoxycarbonylalkyl, $R^{34}$, when present, comprises alkyl, aralkyl, $COR^{35}$, or $SO_2R^{35}$, $R^{35}$, when present, comprises alkyl, aryl, or aralkyl l, m, n, and p are integers independently having values 0 and 1, q, r, and s, are integers independently having values ranging between 0 and 6 or any range therebetween, $R^1$, $R^2$, $R^3$, $R^4$, $R^5$, $R^6$, $R^7$, $R^8$, $R^9$, $R^1$, $R^{11}$, $R^{12}$, $R^{13}$, $R^{14}$, $R^{15}$, $R^{16}$, $R^{21}$, $R^{22}$, $R^{23}$, $R^{24}$, $R^{34}$ and $R^{35}$ when present may independently be either unsubstituted or substituted with one or more substituents comprises alkyl, aryl, aralkyl, cycloalkyl, cycloalkylalkyl, heterocyclyl, heterocyclylalkyl, heterocyclylaryl, hydroxy, alkoxy, azido, hydroxyalkyl, aryloxy, hydroxyaryl, alkoxyaryl, halo, haloalkyl, haloalkoxy, haloaryl, amino, alkylamino, dialkylamino, arylamino, diarylamino, alkoxycarbonyl, alkoxycarbonylalkyl, —NHCO(alkyl), —NHCO(aryl), —NHCO(aralkyl), —NHCO(haloalkyl), —$NHSO_2$(alkyl), —$NHSO_2$(aryl), —$NHSO_2$(aralkyl), —OCO(alkylamino), or —OCO(dialkylamino) provided that, in certain embodiments, when $M^3$ comprises $NR^6$, $M^4$ is absent, and $R^{12}$ comprises $CNR^{22}R^{23}$, then $R^{23}$ is not 1-(1,3-benzodioxol-5-yl)-3-ethoxy-3-oxopropyl, provided that, in certain embodiments, when $M^3$ and $M^4$ are absent, $R^{12}$ is not of the formula $AC(=J)EC(H)(MX)TLR^{25}$, A is selected from the group consisting of —O—, —S—, and —$NR^{26}$—, E is selected from the group consisting of —CH2-, —O—, —S—, and —$NR^{27}$—, J is selected from the group consisting of —O—, —S—, and —$NR^{28}$—, T is selected from the group consisting of CO and $(CH_2)_2$ b is an integer of zero to three, L is selected from the group consisting of —$(CH_2)_n$—, —O—, —S—, and —$NR^{29}$— n is an integer of zero to three,

M is selected from the group consisting of $CR^{30}R^{31}$ and $(CH_2)_u$ u is an integer of zero or one, X is selected from the group consisting of $CO_2B$, $PO_3H_2$, $SO_3H$, $OPO_3H_2$, $CONHCOR^{32}$, $CONHSO_2R^{33}$, oxazolyl, tetrazolyl and hydrogen, B, $R^{25}$, $R^{26}$, $R^{27}$, $R^{28}$, $R^{29}$, $R^3$, $R^{31}$, $R^{32}$ and $R^{33}$ are independently selected from the group consisting of hydrogen, halogen alkyl, alkenyl, alkynyl, alkoxy, alkenoxy, alkynoxy, thioalkoxy, aliphatic acyl, —$CF_3$, nitro, amino, cyano, $N(C_1\text{-}C_3\ alkyl)CO(C_1\text{-}C_3\ alkyl)$, $C_1$-$C_3$ alkylamino, alkenylamino, alkynylamino, di($C_1$-$C_3$ alkyl)amino, $CO_2$($C_1$-$C_3$ alkylamino), CONH($C_1$-$C_3$ alkylamino), CH═NOH, $PO_3H_2$, $OPO_3H_2$, CON($C_1$-$C_3$ alkyl)$_2$, haloalkyl, alkoxycarbonyl, alkoxyalkoxy, carboxaldehyde, carboxamide, cycloalkyl, cycloalkenyl, cycloalkynyl, aryl, aroyl, aryloxy, arylamino, biaryl, thioaryl, heterocyclyl, heterocycloyl, alkylaryl, aralkenyl, aralkyl, alkylheterocyclyc, heterocyclycalkyl, sulfonyl, sulfonamide, carbamate, aryloxyalkyl, carboxyl and CONH(benzyl), B, X, R25, R26, R27, R28, R29, R30, R31 and R32 are unsubstituted or substituted with at least one electron donating or electron withdrawing group, provided that, in certain embodiments, when $R^3$ comprises hydrogen, alkyl or aryl, $R^{12}$ is not hydrogen, provided that, in certain embodiments, when $R^1$ comprises phenyl, $R^3$ comprises benzyloxycarbonylamino, and $R^{12}$ comprises hydrogen, $R^2$ is not 2-methoxybenzyl, provided that, in certain embodiments, when $R^1$ comprises alkyl, $R^2$ comprises aralkyl, provided that, in certain embodiments, when $M^1$ comprises $SO_2$ and $R^1$ comprises phenyl, 4-methylphenyl or 2,4,6-trimethylphenyl, $R^2$ is not alkyl, 2-phenethyl, benzyl, or 2-methoxy-2-oxoethyl, provided that, in certain embodiments, when $M^1$ comprises CO and $R^1$ comprises 2-furyl, 4-pyridyl, or 3,5-dinitrophenyl, $R^2$ is not alkyl, benzyl or 2-(1H-indol-2-yl)ethyl, provided that, in certain embodiments, when $M^2$ comprises CO, then $M^6$ comprises $NR^{34}(CH_2)_q$, wherein q is not 0, provided that, in certain embodiments, when $M^2$ comprises CO, $M^3$ comprises O, S, $NR^6$ or $(CR^7R^8)_m$, or provided that, in certain embodiments, when $M^2$ comprises $SO_2$ or $(CR^4R^5)_1$, $M^3$ comprises $(CR^7R)_m$.

12. The method of claim 11, wherein, in the administering step, the one or more compounds of the general Formula (I) comprise:

one or more of a first class of the compounds of Formula (I) defined by:

$R^1$ is selected from the group consisting of aryl and aralkyl, $R^2$ is alkyl, aryl, or aralkyl, $M^1$ is $CH_2$, $M^2$ is CO, $M^3$ is O, S, or $NR^6$, $R^6$ when present is hydrogen or lower alkyl, $M^4$ is absent or $CH_2$, $M^5$ is $(CR^{11}R^{12})$, $R^{11}$ is hydrogen, $R^{12}$ is selected from the group consisting of hydrogen, $NR^{21}CONR^{22}R^{23}$, $NR^{21}COR^{24}$, $NR^{21}SO_2R^{24}$, $NR^{21}COOR^{24}$, $OCOR^{24}$, $OR^{24}$, $O(CH_2CH_2O)sR^{24}$, $COOR^{24}$, alkyl, and hydroxyalkyl, s is an integer of 1 to 6, $R^{21}$ and $R^{22}$ when present are independently selected from the group consisting of hydrogen or lower alkyl, $R^{23}$ when present is selected from the group consisting of hydroxyalkyl, alkoxyalkyl, alkyl, aryl, aralkyl and alkoxycarbonylalkyl, provided that when $M^3$ is $NR^6$ and $M^4$ is absent, then $R^{23}$ is not 1-(1,3-benzodioxol-5-yl)-3-ethoxy-3-oxopropyl, $R^{24}$ when present is selected from the group consisting of alkyl, aryl, aralkyl, heterocyclyl, cycloalkyl, cycloalkylalkyl, and heterocyclylalkyl, and mixtures thereof, $M^6$ is $(CH_2)_q$, where q is an integer from 0 to 6, $R^3$ is selected from the group consisting of hydrogen, $CONR^{13}R^{14}$, $NR^{15}COOR^{16}$, $NR^{15}COR^{16}$, $NR^{15}CONR^{13}R^{14}$, $NR^{15}SO2R^{16}$, $OCOR^{16}$, $COOR^{16}$, $OR^{16}$, $SR^{16}$, heterocyclyl, hydroxyl, hydroxyalkyl, guanadino, alkyl and aryl, $R^{13}$ and $R^{15}$ when present are independently hydrogen or lower alkyl, $R^{14}$ and $R^{16}$ when present are independently selected from the group consisting of hydrogen, alkyl, aryl, aralkyl, cycloalkyl, heterocyclyl, cycloalkylalkyl, and heterocyclylalkyl, $R^1$, $R^2$, $R^3$, $R^{12}$, $R^{14}$, $R^{16}$, $R^{23}$ and $R^{24}$ when present may independently be either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(aralkyl), —NHCO(haloalkyl), —$NHSO_2$(alkyl), —$NHSO_2$(aryl), —$NHSO_2$(aralkyl), alkoxycarbonyl, alkoxycarbonylalkyl, —OCO(alkylamino), —OCO(dialkylamino), and mixtures thereof;

or one or more of a second class of the compounds of Formula (I) defined by:

$R^1$ is aryl or aralkyl, $R^2$ is alkyl or aralkyl, $M^1$ is $CH_2$, $M^2$ is CO, $M^3$ is absent or is O or $CH_2$, $M^4$ is absent or is $CH_2$, $M^5$ is absent or is O or $(CR^{11}R^{12})$, $R^{11}$ is hydrogen, $R^{12}$ is selected from the group consisting of hydrogen, $NR^{21}CONR^{22}R^{23}$, $NR^{21}COR^{24}$, $NR^{21}SO2R^{24}$ and $NR^{21}COOR^{24}$, $R^{21}$ and $R^{22}$ each of which, when present is independently selected from the group of hydrogen and lower alkyl, $R^{23}$ and $R^{24}$, each of which, when present is independently selected from the group consisting of hydrogen, alkyl, aryl, cycloalkyl, cycloalkylalkyl, heterocyclyl, heterocyclylalkyl and aralkyl, $M^6$ is selected from the group consisting of $(CH_2)_q$, $(CH_2)_q$—CH═CH—$(CH_2)_r$, $(CH_2)_q$-arylene-$(CH_2)$, and $(CH_2CH_2O)_q$, where q and r are independently integers from 0 to 6, $R^3$ is $CONR^{13}R^{14}$, $R^{13}$ and $R^{14}$, each of which, when present is independently selected from the group consisting of hydrogen, alkyl, aryl, cycloalkyl, cycloalkylalkyl, heterocyclyl, heterocyclylalkyl and aralkyl, and $R^1$, $R^2$, $R^{13}$, $R^{14}$, $R^{23}$ and $R^{24}$, when present, independently either are unsubstituted or are substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(aralkyl), —NHCO(haloalkyl), —$NHSO_2$(alkyl), —$NHSO_2$(aryl), —$NHSO_2$(aralkyl), alkoxycarbonyl, alkoxycarbonylalkyl, —OCO(alkylamino), —OCO(dialkylamino), and mixtures thereof;

or one or more of a third class of the compounds of Formula (I) defined by:

$R^1$ is aryl or aralkyl, $R^2$ is alkyl or aralkyl, $M^1$ is $CH_2$, $M^2$ is $SO_2$ or CO, $M^3$ is absent or is $CH_2$, $M^4$ is absent or is $CH_2$, $M^5$ is absent or is ($CR^{11}R^{12}$), $R^{11}$, when present, is hydrogen, $R^{12}$, when present, is selected from the group consisting of hydrogen, alkyl, $NR^{21}CONR^{22}R^{23}$, $NR^{21}COR^{24}$, $NR^{21}SO2R^{24}$ and $NR^{21}COOR^{24}$, $R^{21}$ and $R^{22}$, each of which when present, is independently selected from the group of hydrogen, lower alkyl, and aralkyl, $R^{23}$ and $R^{24}$, each of which, when present is independently selected from the group consisting of hydrogen, alkyl, aryl, cycloalkyl, cycloalkylalkyl, heterocyclyl, heterocyclylalkyl and aralkyl, $M^6$ is $(CH_2)_q$, or $NR^{34}(CH_2)_q$, q is an integer from 0 to 6, $R^{34}$, when present, is selected form the group consisting of alkyl, aralkyl, $COR^{35}$, and $SO_2R^{35}$, $R^{35}$ when present, is selected form the group consisting of alkyl, aryl, and aralkyl, and $R^3$ is selected from the group consisting of $CONR^{13}R^{14}$, $SO_2NR^{13}R^{14}$, $NR^{15}COOR^{16}$, $NR^{15}COR^{16}$, $NR^{15}CONR^{13}R^{14}$, and $NR^{15}SO_2R^{16}$, $R^{13}$ and $R^{14}$, each of which, when present, is independently selected from the group consisting of hydrogen, alkyl, aryl, cycloalkyl, cycloalkylalkyl, heterocyclyl, heterocyclylalkyl and aralkyl, $R^{15}$ and $R^{16}$, each of which when present, is independently selected from the group of hydrogen, lower alkyl, and aralkyl, $R^1$, $R^2$, $R^{13}$, $R^{14}$, $R^{15}$, $R^{16}$, $R^{23}$, $R^{24}$, $R^{34}$ and $R^{35}$, when present, either are unsubstituted or are substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(aralkyl), —NHCO(haloalkyl), —$NHSO_2$(alkyl), —$NHSO_2$(aryl), —$NHSO_2$(aralkyl), alkoxycarbonyl, alkoxycarbonylalkyl, —OCO(alkylamino), and —OCO(dialkylamino), with the proviso that when $M^2$ is CO, then $M^6$ is $NR^{34}(CH_2)_q$, q is not 0;

or one or more of a fourth class of the compounds of Formula (I) defined by:

$R^1$ is alkyl, aryl or aralkyl, $R^2$ is selected from the group consisting of aralkyl and alkyl, provided that when $R^1$ is alkyl, $R^2$ is aralkyl, $M^1$ is CO or $SO_2$, provided that when $M^1$ is $SO_2$ and $R^1$ is phenyl, 4-methylphenyl or 2,4,6-trimethylphenyl, $R^2$ is not alkyl, 2-phenethyl, benzyl, or 2-methoxy-2-oxoethyl, and when $M^1$ is CO and $R^1$ is 2-furyl, 4-pyridyl, or 3,5-dinitrophenyl, $R^2$ is not alkyl, benzyl or 2-(1H-indol-2-yl)ethyl, $M^2$ is absent or $CH_2$, $M^3$ and $M^4$ are absent, $M^5$ is ($CR^{11}R^{12}$), $R^{11}$ is hydrogen, $R^{12}$ is selected from the group consisting of hydrogen, $NR^{21}CONR^{22}R^{23}$, $NR^{21}COR^{24}$, $NR^{21}SO_2R^{24}$, $NR^{21}COOR^{24}$, $CONR^{22}R^{23}$, $COOR^{24}$, $O(CH_2CH_2O)_sR^{24}$, hydroxyalkyl, and alkoxyalkyl, $R^{21}$, and $R^{22}$, when present, are independently selected from the group consisting of hydrogen and $C_1$-$C_6$ alkyl, and $R^{23}$ and $R^{24}$, each of which, when present, is independently selected from the group consisting of hydrogen, alkyl, aryl, cycloalkyl, cycloalkylalkyl, heterocyclyl, heterocyclylalkyl and aralkyl, and s is an integer of 1 to 6, $M^6$ is $(CH_2)_q$, q is an integer of 0 to 6, $R^3$ is selected from the group consisting of $NR^{15}COOR^{16}$, $NR^{15}COR^{16}$, $NR^{15}CONR^{13}R^{14}$, and $NR^{15}SO_2R^{16}$, and $R^{13}$ when present, is independently selected from the group consisting of hydrogen and $C_1$-$C_6$ alkyl, and $R^{14}$, $R^{15}$, and $R^{16}$ each of which, when present, are independently selected from the group consisting of hydrogen, alkyl, aryl, cycloalkyl, cycloalkylalkyl, heterocyclyl, heterocyclylalkyl and aralkyl, and $R^1$, $R^2$, $R^3$, $R^{12}$, $R^{14}$, $R^{15}$, $R^{16}$, $R^{23}$, and $R^{24}$, when present, independently either are unsubstituted or are substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(aralkyl), —NHCO(haloalkyl), —$NHSO_2$(alkyl), —$NHSO_2$(aryl), —$NHSO_2$(aralkyl), alkoxycarbonyl, alkoxycarbonylalkyl, —OCO(alkylamino) and —OCO(dialkylamino);

pharmaceutically acceptable salts thereof; or mixtures thereof.

13. The method of claim 12, wherein, in the administering step, the one or more compounds of the general Formula (I) comprise:

one or more of the first class of the compounds of Formula (I).

14. The method of claim 12, wherein, in the administering step, the one or more compounds of the general Formula (I) comprise:

one or more of the second class of the compounds of Formula (I).

15. The method of claim 12, wherein, in the administering step, the one or more compounds of the general Formula (I) comprise:

one or more of the third class of the compounds of Formula (I).

16. The method of claim 12, wherein, in the administering step, the one or more compounds of the general Formula (I) comprise:

one or more of the fourth class of the compounds of Formula (I).

17. The method of claim 12, wherein, in the administering step:

$R^1M^1$ and $R^2$ independently comprising 2-thienylmethyl, 3-methoxybenzyl, 4-methoxybenzyl, 2-(2-thienyl) ethyl, pyridin-4-ylmethyl, 4-dimethylaminobenzyl, or pyridin-3-ylmethyl; and when $R^3$ comprising $CONR^{13}R^{14}$ or $SO_2NR^{13}R^{14}$, then $R^{13}$ and $R^{14}$ independently comprise 2-thienylmethyl, 3-methoxybenzyl, 4-methoxybenzyl, 2-(2-thienyl) ethyl, pyridin-4-ylmethyl, 4-dimethylaminobenzyl, or pyridin-3-ylmethyl.

18. The method of claim 11, wherein, in the administering step:

the one or more of the first class compounds of Formula (I) include:

N,N,N',N'-tetrakis(2-thienylmethyl)pentanediamide; N-(3-methoxybenzyl)-N,N',N'-tris(2-thienylmethyl) pentanediamide; N,N,N'-tris(2-thienylmethyl)pentanediamide; N'-[2-(2-thienyl)ethyl]-N,N-bis(2-thienylmethyl)pentanediamide; N-[2-(2-thienyl) ethyl]-N,N',N'-tris(2-thienylmethyl)pentanediamide; N,N-bis(pyridin-4-ylmethyl)-N',N'-bis(2-thienylmethyl) pentanediamide; N,N-bis(pyridin-3-ylmethyl)-N',N'-bis(2-thienylmethyl)pentanediamide; N,N-bis(3-methoxybenzyl)-N',N'-bis(2-thienylmethyl) pentanediamide; N,N,N',N'-tetrakis(4-methoxy benzyl)pentanediamide; N,N,N',N'-tetrakis(2-thienylmethyl)hexanediamide; N,N,N',N'-tetrakis(4-methoxybenzyl)hexanediamide; N,N,N',N'-tetrakis (3-methoxy benzyl)hexanediamide; N,N,N',N'-tetrakis(2-thienylmethyl)heptanediamide; 2,2'-(1,3-phenylene)bis[N,N-bis(2-thienylmethyl)acetamide]; N,N,N',N'-tetrakis (4-methoxybenzyl)heptanediamide; N,N,N',N'-tetrakis(2-thienylmethyl)octane diamide; (3E)-N,N,N',N'-tetrakis(2-thienylmethyl) hex-3-enediamide; 2,2'-oxybis [N,N-bis(2-thienylmethyl)acetamide]; 3-oxo-1-(2-thienyl)-2-(2-thienyl methyl)-4,7,10-trioxa-2-azadodecan-12-ylbis(2-thienylmethyl)carbamate; N,N,N',N'-tetrakis(4-methoxybenzyl)succinamideethane-1,2-diyl bis[bis (2-thienylmethyl) carbamate]; N,N,N',N'-tetrakis(4-methoxybenzyl)octanediamide; N,N,N',N'-tetrakis (2-thienylmethyl)pyridine-3,5-dicarboxamide; N,N,N',N'-tetrakis (2-thienylmethyl)pyridine-2,6-dicarboxamide; N,N,N',N'-tetrakis(2-thienyl methyl) pyridine-2,4-dicarboxamide; 2,2'-(1,4-phenylene)bis [N,N-bis(2-thienylmethyl) acetamide]; 8-{2-[bis(2-thienylmethyl)amino]-2-oxoethoxy}-N,N-bis(2-thienyl methyl)quinoline-2-carboxamide; N,N'-bis (4-methoxybenzyl)-N,N'-bis(2-thienylmethyl)

hexanediamide; tert-butyl{(2S)-1,6-bis[bis(2-thienyl methyl)amino]-1,6-dioxohexan-2-yl}carbamate; or mixture thereof;

the one or more of the second class compounds of Formula (I) include:

1,2-bis(bis(thiophen-2-ylmethyl)carbamate)ethane; 1,2-bis(bis(3-methyloxybenzyl) carbamate)ethane; 1,2-bis(bis(4-methyloxybenzyl)carbamate)ethane; 1,2-bis((thiophen-2-ylmethyl)(3-methyloxybenzyl) carbamate)ethane; 1,2-bis((thiophen-2-ylmethyl)(4-methyloxybenzyl)carbamate)ethane; 1,2-bis((3-methyloxybenzyl)(4-methyloxybenzyl)carbamate) ethane; 1,5-bis(bis(thiophen-2-ylmethyl)carbamate)-3-oxapentane; 1,5-bis(bis(3-methyloxybenzyl) carbamate)-3-oxapentane; 1,5-bis(bis(4-methyloxybenzyl)carbamate)-3-oxapentane; 1,5-bis ((thiophen-2-ylmethyl)(3-methyloxybenzyl) carbamate)-3-oxapentane; 1,5-bis((thiophen-2-ylmethyl)(4-methyloxybenzyl)carbamate)-3-oxapentane; 1,5-bis((3-methyloxybenzyl)(4-methyloxybenzyl)carbamate)-3-oxapentane;(ethane-1,2-diylbis(oxy))bis(ethane-2,1-diyl)bis(bis (thiophen-2-ylmethyl)carbamate); 1,8-bis(bis (thiophen-2-yl methyl)carbamate)-3,6-dioxaoctane; 1,8-bis(bis(3-methyloxybenzyl)carbamate)-3,6-dioxaoctane; 1,8-bis(bis(4-methyloxybenzyl)carbamate)-3,6-dioxaoctane; 1,8-bis ((thiophen-2-ylmethyl) (3-methyloxybenzyl)carbamate)-3,6-dioxaoctane; 1,8-bis ((thiophen-2-ylmethyl)(4-methyloxybenzyl) carbamate)-3,6-dioxaoctane; 1,8-bis((3-methyloxybenzyl)(4-methyloxybenzyl)carbamate)-3,6-dioxaoctane; 1,11-bis(bis (thiophen-2-ylmethyl) carbamate)-3,6,9-trioxaundecane; 1,11-bis(bis(3-methyloxy benzyl)carbamate)-3,6,9-trioxaundecane; 1,11-bis(bis(4-methyloxybenzyl) carbamate)-3,6,9-trioxaundecane; 1,11-bis((thiophen-2-ylmethyl)(3-methyloxy benzyl)carbamate)-3,6,9-trioxaundecane; 1,11-bis((thiophen-2-ylmethyl)(4-methyloxybenzyl) carbamate)-3,6,9-trioxaundecane; 1,11-bis((3-methyloxybenzyl)(4-methyloxybenzyl)carbamate)-3,6,9-trioxaundecane; 1,14-bis(bis(thiophen-2-yl methyl) carbamate)-3,6,9,12-tetraoxatetradecane; 1,14-bis (bis(3-methyloxy benzyl)carbamate)-3,6,9,12-tetraoxatetradecane; 1,14-bis(bis(4-methyloxy benzyl)carbamate)-3,6,9,12-tetraoxatetradecane; 1,14-bis((thiophen-2-ylmethyl)(3-methyloxybenzyl) carbamate)-3,6,9,12-tetraoxatetradecane;1,14-bis ((thiophen-2-yl methyl)(4-methyloxybenzyl)carbamate)-3,6,9,12-tetraoxatetradecane; 1,14-bis((3-methyloxybenzyl)(4-methyloxybenzyl)carbamate)-3,6,9,12-tetraoxatetradecane; 1,17-bis(bis(thiophen-2-ylmethyl)carbamate)-3,6,9,12,15-pentaoxatetradecane; 1,17-bis(bis(3-methyloxybenzyl)carbamate)-3,6,9,12,15-pentaoxatetradecane; 1,17-bis(bis(4-methyloxybenzyl)carbamate)-3,6,9,12,15-pentaoxatetradecane; 1,17-bis((thiophen-2-ylmethyl)(3-methyloxybenzyl)carbamate)-3,6,9,12,15-pentaoxatetradecane; 1,17-bis((thiophen-2-ylmethyl)(4-methyloxybenzyl)carbamate)-3,6,9,12,15-pentaoxatetradecane; 1,17-bis((3-methyloxybenzyl)(4-methyloxybenzyl)carbamate)-3,6,9,12,15-pentaoxatetradecane; or mixtures thereof;

the one or more of the third class compounds of Formula (I) include:

methyl (6S,10S)-10-(1,3-benzodioxol-5-yl)-6-butyl-3,8-dioxo-1-(2-thienyl)-2-(2-thienylmethyl)-4-oxa-2,7,9-triazadodecan-12-oate; methyl (6S,10R)-10-(1,3-benzodioxol-5-yl)-6-butyl-3,8-dioxo-1-(2-thienyl)-2-(2-thienylmethyl)-4-oxa-2,7,9-triazadodecan-12-oate;methyl(6S,10S)-10-(1,3-benzodioxol-5-yl)-6-butyl-7-methyl-3,8-dioxo-1-(2-thienyl)-2-(2-thienylmethyl)-4-oxa-2,7,9-triazadodecan-12-oate; methyl (6S,10S)-10-(1,3-benzodioxol-5-yl)-6-butyl-9-methyl-3,8-dioxo-1-(2-thienyl)-2-(2-thienylmethyl)-4-oxa-2,7,9-triazadodecan-12-oate; ethyl(6S,10R)-10-(1,3-benzodioxol-5-yl)-6-butyl-7-methyl-3,8-dioxo-11-(2-thienyl)-2-(2-thienylmethyl)-4-oxa-2,7,9-triazadodecan-12-oate; methyl (10S)-10-(1,3-benzodioxol-5-yl)-3,8-dioxo-1-(2-thienyl)-2-(2-thienylmethyl)-4-oxa-2,7,9-triazadodecan-12-oate; methyl 3,8-dioxo-1-(2-thienyl)-2-(2-thienylmethyl)-4-oxa-2,7,9-triazadodecan-12-oate;methyl(6S,10S)-10-(1,3-benzodioxol-5-yl)-6-butyl-2-methyl-3,8-dioxo-1-(2-thienyl)-4-oxa-2,7,9-triazadodecan-12-oate; methyl (6S)-6-butyl-3,8-dioxo-1-(2-thienyl)-2-(2-thienylmethyl)-4-oxa-2,7,9-triazadodecan-12-oate; (2S)-2-{[(1,3-benzodioxol-5-ylmethyl)carbamoyl]amino}hexyl bis(2-thienylmethyl) carbamate; methyl (6S,10S)-6-butyl-3,8-dioxo-10-phenyl-1-(2-thienyl)-2-(2-thienylmethyl)-4-oxa-2,7,9-triazadodecan-12-oate; (2S)-2-({[(1S)-1-(1,3-benzodioxol-5-yl)-3-hydroxypropyl] carbamoyl}amino)hexylbis(2-thienylmethyl) carbamate; (2S)-2-[(benzylcarbamoyl)amino] hexylbis(2-thienyl methyl)carbamate; (2S)-2-[(morpholin-4-ylcarbonyl)amino]hexylbis(2-thienyl methyl)carbamate; (2S)-2-{[(3-methoxypropyl)carbamoyl]amino}hexylbis(2-thienyl methyl)carbamate; (2S)-2-{[(2-methoxyethyl)carbamoyl] amino}hexylbis(2-thienylmethyl)carbamate; tert-butyl [(2S)-1-{[bis(2-thienylmethyl)carbamoyl] oxy}hexan-2-yl]carbamate; (2S)-2-[(tert-butylcarbamoyl)amino]hexylbis(2-thienyl methyl) carbamate; (2S)-2-[(isopropylcarbamoyl)amino] hexylbis(2-thienylmethyl) carbamate; (2S)-2-[(methylcarbamoyl)amino]hexylbis(2-thienylmethyl)carbamate; tert-butyl [(2R)-1-{[bis(2-thienylmethyl)carbamoyl]oxy}hexan-2-yl] carbamate; benzyl {(5S)-6-{[bis(2-thienylmethyl) carbamoyl]oxy}-5-[(tert-butoxycarbonyl) amino] hexyl}carbamate; methyl(9S,13S)-13-(1,3-benzodioxol-5-yl)-9-({[bis(2-thienylmethyl) carbamoyl]oxy}methyl)-3,11-dioxo-1-phenyl-2-oxa-4,10,12-triaza pentadecan-15-oate; (2S)-2-acetamidohexylbis(2-thienylmethyl)carbamate; methyl (6R,10S)-10-(1,3-benzodioxol-5-yl)-6-butyl-3,8-dioxo-1-(2-thienyl)-2-(2-thienyl methyl)-4-oxa-2,7,9-triazadodecan-12-oate;methyl(6R,10R)-10-(1,3-benzodioxol-5-yl)-6-butyl-3,8-dioxo-1-(2-thienyl)-2-(2-thienylmethyl)-4-oxa-2,7,9-triazadodecan-12-oate; methyl {[bis(2-thienylmethyl)carbamoyl](methyl)amino}acetate; methyl {[bis(2-thienylmethyl)carbamoyl](butyl) amino}acetate; tert-butyl {[bis(2-thienyl methyl)carbamoyl](butyl)amino}acetate; benzyl {(5S)-6-{[bis(4-methoxybenzyl) carbamoyl]oxy}-5-[(tert-butoxycarbonyl)amino]hexyl}carbamate; tert-butyl [(2S)-1-{[bis(4-methoxybenzyl)carbamoyl] oxy}hexan-2-yl]carbamate; methyl(6S,10S)-10-(1,3-benzodioxol-5-yl)-6-butyl-2-(4-methoxybenzyl)-1-(4-methoxyphenyl)-3,8-dioxo-4-oxa-2,7,9-triazadodecan-12-oate;(2S)-2-({[(1S)-1-(1,3-benzodioxol-5-yl)-3-hydroxypropyl] carbamoyl}amino)hexyl bis(4-methoxybenzyl) carbamate; (2S)-2-[(tertbutoxycarbonyl)amino] hexyldibenzylcarbamate; methyl (6S,10S)-10-(1,3-benzodioxol-5-yl)-2-benzyl-6-butyl-3,8-dioxo-1-phenyl-4-oxa-2,7,9-triazadodecan-12-oate; tert-butyl [(2S)-1-{[bis(4-methylbenzyl)carbamoyl] oxy}hexan-2-yl]carbamate;methyl(6S,10S)-10-(1,3-benzodioxol-5-yl)-6-butyl-2-(4-methylbenzyl)-1-(4-methylphenyl)-3,8-dioxo-4-oxa-2,7,9-triazadodecan-12-oate; tert-butyl [(2S)-1-{[bis(4-chlorobenzyl)carbamoyl]oxy}hexan-2-yl] carbamate; methyl (6S,10S)-10-(1,3-benzodioxol-5-yl)-6-butyl-2-(4-chlorobenzyl)-1-(4-chlorophenyl)-3,8-dioxo-4-oxa-2,7,9-triazadodecan-12-oate;(2S)-2-[(tertbutoxycarbonyl)amino]hexyl(4-bromo benzyl)(2-thienylmethyl)carbamate;methyl(6S,10S)-10-(1,3-benzodioxol-5-yl)-2-(4-bromobenzyl)-6-butyl-3,8-dioxo-1-(2-thienyl)-4-oxa-2,7,9-triazadodecan-12-oate; methyl(6S,10S)-2-(4-azidoobenzyl)-10-(1,3-benzodioxol-5-yl)-6-butyl-3,8-dioxo-1-(2-thienyl)-4-oxa-2,7,9-triazadodecan-12-oate; (2S)-2-[(tert-butoxycarbonyl)amino] hexylphenyl(2-thienylmethyl)carbamate;methyl(6S,10S)-10-(1,3-benzodioxol-5-yl)-6-butyl-3,8-dioxo-2-phenyl-1-(2-thienyl)-4-oxa-2,7,9-triazadodecan-12-oate; tert-butyl [(2S)-1-{[bis(3-thienylmethyl) carbamoyl]oxy}hexan-2-yl]carbamate; methyl (6S,10S)-10-(1,3-benzodioxol-5-yl)-6-butyl-3,8-dioxo-1-(3-thienyl)-2-(3-thienyl methyl)-4-oxa-2,7,9-triazadodecan-12-oate; benzyl [(5S)-5-[(tertbutoxycarbonyl) amino]-6-{[butyl (2-thienylmethyl)carbam oyl]oxy}hexyl]carbamate; (2S)-2-[(tert-butoxycarbonyl)amino]hexylbutyl(2-thienylmethyl)carbamate;methyl(3S,7S)-3-(1,3-benzodioxol-5-yl)-7-butyl-5,11-dioxo-11-(2-thienylmethyl)-9-oxa-4,6,11-triazapenta decan-1-oate; benzyl [(5S)-5-[(tert-butoxycarbonyl)amino]-6-{[(2-methoxyethyl)(2-thienylmethyl)carbamoyl] oxy}hexyl]carbamate; (2S)-2-[(tert-butoxycarbonyl) amino]hexyl(2-methoxyethyl)(2-thienylmethyl)carbamate;methyl(9S,13S)-13-(1,3-benzodioxol-5-yl)-9-butyl-6, 11-dioxo-5-(2-thienylmethyl)-2,7-dioxa-5,10,12-triazapentadecan-15-oate; (2S)-2-[({3-[(methylsulfonyl)amino]benzyl}carbamoyl) amino] hexyl(2-methoxyethyl)(2-thienylmethyl)carbamate; (2S)-2-{[(4-bromobenzyl)carbamoyl] amino}hexylbis(2-thienylmethyl)carbamate; (2S)-2-{[(4-azidobenzyl)carbamoyl]amino}hexylbis(2-thienylmethyl)carbamate; tert-butyl[(2S)-1-{[bis(2-thienylmethyl)carbamoyl]thio}hexan-2-yl] carbamate;methyl(6S,10S)-10-(1,3-benzodioxol-5-yl)-6-butyl-3,8-dioxo-1-(2-thienyl)-2-(2-thienylmethyl)-4-thia-2,7,9-triazadodecan-12-oate; or mixtures thereof;

the one or more of the fourth class compounds of Formula (I) include:

N-{2-[bis(2-thienylmethyl)sulfamoyl]ethyl}-N-(2-thienylmethyl)thiophene-2-sulfonamide; N-{2-[bis(2-thienylmethyl)sulfamoyl]ethyl}-N-(2-thienylmethyl) thiophene-2-carboxamide; 2-{butyl[(2-thienylmethyl)carbamoyl]amino}-N,N-bis(2-thienylmethyl)ethanesulfonamide; 2-{[bis(2-thienylmethyl)carbamoyl](butyl)amino}-N,N-bis(2-thienylmethyl)ethanesulfonamide; N-{3-[bis(2-thienyl methyl)sulfamoyl]propyl}-N-(2-thienylmethyl) thiophene-2-sulfonamide; 2-[(methylsulfonyl)(2-thienylmethyl)amino]-N,N-bis(2-thienylmethyl) ethanesulfonamide; 2-{[bis(2-thienylmethyl)carbamoyl]amino}-N,N-bis(2-thienylmethyl)ethanesulfonamide; N-{2-[bis(2-thienylmethyl)sulfamoyl] ethyl}thiophene-2-sulfonamide; N-{2-[bis(2-thienylmethyl)sulfamoyl]ethyl}-2-(2-thienyl) acetamide; N-{2-[bis(2-thienylmethyl)sulfamoyl] ethyl}thiophene-2-carboxamide; N,N-bis(2-thienylmethyl)-2-{[(2-thienylmethyl) carbamoyl] amino}ethanesulfonamide; 2-({2-[bis(2-thienylmethyl)sulfamoyl]ethyl}amino)-N,N-bis(2-thienylmethyl)acetamide; 3-[{2-[bis(2-thienyl methyl)amino]-2-oxoethyl}(butyl)amino]-N,N-bis (2-thienylmethyl)propanamide; 2-[{2-[bis(2-thienylmethyl)sulfamoyl]ethyl}(methyl)amino]-N,N-bis (2-thienyl methyl)acetamide; 2-[{2-[bis(2-thienylmethyl)sulfamoyl]ethyl}(butyl)amino]-N,N-bis(2-thienylmethyl)acetamide; 3-({2-[bis(2-thienylmethyl)sulfamoyl]ethyl}amino)-N,N-bis(2-thienylmethyl)propanamide; 3-({2-[bis(2-thienylmethyl) sulfamoyl]ethyl}amino)-N,N-bis(4-methoxybenzyl)propanamide; 3-({2-[bis(4-methoxybenzyl)sulfamoyl]ethyl}amino)-N,N-bis(2-thienylmethyl)pro panamide; 3-[{2-[bis(2-thienylmethyl)sulfamoyl]ethyl}(methyl)amino]-N, N-bis (2-thienylmethyl)propanamide; 3-[{2-[bis(4-methoxybenzyl)sulfamoyl]ethyl}(methyl)amino]-N, N-bis(2-thienylmethyl)propanamide; (2S)-2-({2-[bis (2-thienylmethyl) sulfamoyl]ethyl}amino)-N,N-bis(2-thienylmethyl)hexanamide; (2S)-2-({2-[bis(4-methoxybenzyl)sulfamoyl]ethyl}amino)-N,N-bis(2-thienylmethyl) hexanamide; 2-(acetyl{2-[bis(2-thienylmethyl)sulfamoyl]ethyl}amino)-N,N-bis (2-thienylmethyl)acetamide; 2-(acetyl{2-[bis(4-methoxybenzyl) sulfamoyl]ethyl}amino)-N,N-bis (2-thienyl-methyl)acetamide; or mixtures thereof;

pharmaceutically acceptable salts thereof; and mixtures thereof.

19. A method comprising:

administering an antitumor pharmaceutical composition comprising an effective amount of one or more integrin activators to an animal or human, and administering one or more anticancer agents, the one or more anticancer agents: (a) activate an anti-tumor immune T cell response; (b) prevent immune suppression by targeting inhibitory receptors including PD-1, CTLA-4, LAG-3, TIM-3, BLTA, or combinations thereof; (c) inhibiting myeloid derived suppressor cells, tumor associated macrophages, regulatory T cells, or combinations thereof; or (d) any combination thereof, wherein the one or more integrin activators comprise one or more N,N-disubstituted amide compounds, N,N-disubstituted carbamate compounds, N,N-disubstituted urea compounds, N,N-disubstituted sulfonamide compounds, or combinations thereof, wherein the effective amount is sufficient to produce a plasma concentration of the one or more integrin activators in the animal or the human of between about 1 nano molar (nM) and about nM after administrating, wherein the effective amount is also sufficient to prompt an immune response to antigens of a solid tumor by:

(a) priming and activating antigen presenting cells and T-cells to the solid tumor antigens;

(b) trafficking natural T-cells and the activated T-cells to the solid tumor;

(c) prompting infiltration of the nature T-cells and activated T-cells into the solid tumor and recognition of cancer cells in the solid tumor by the natural T-cells and the activated T-cells; and (d) prompting the killing of cancer cells in the solid tumor via the natural T-cells and the activated T-cells resulting in a reduction in a size of the solid tumor, wherein the one or more integrin activators target integrins including α4β1, α4β7, α5β1, αLβ2, αVβ3, or combinations thereof, and wherein the one or more integrin activators improve binding interactions between the integrins and their respective ligands including VCAM-1, fibronectin, MAdCAM-1, ICAM-1, ICAM-2, vitronectin, or combinations thereof.

20. The method of claim 19, wherein, in the administering step:

the one or more N,N-disubstituted amide compounds, N,N-disubstituted carbamate compounds, N,N-disubstitutedurea compounds, N,N-disubstituted sulfonamide compounds, or combinations thereof comprise one or more compounds of the general Formula (I):

$$R^1\text{-}M^1\text{-}N(R^2)\text{-}M^2\text{-}M^3\text{-}M^4\text{-}M^5\text{-}M^6\text{-}R^3 \qquad (I)$$

including:

a first class of the compounds of Formula (I) defined by:

$R^1$ is selected from the group consisting of aryl and aralkyl, $R^2$ is alkyl, aryl, or aralkyl, $M^1$ is $CH_2$, $M^2$ is CO, $M^3$ is O, S, or $NR^6$, $R^6$ when present is hydrogen or lower alkyl, $M^4$ is absent or $CH_2$, $M^5$ is $(CR^{11}R^{12})$, $R^{11}$ is hydrogen, $R^{12}$ is selected from the group consisting of hydrogen, $NR^{21}CONR^{22}R^{23}$, $NR^2COR^2$, $NR^{21}SO_2R^{24}$, $NR^{21}COOR^{24}$, $OCOR^{24}$, $OR^{24}$, $O(CH_2CH_2O)_sR^{24}$, $COOR^{24}$, alkyl, and hydroxyalkyl, s is an integer of 1 to 6, $R^{21}$ and $R^{22}$ when present are independently selected from the group consisting of hydrogen or lower alkyl, $R^{23}$ when present is selected from the group consisting of hydroxyalkyl, alkoxyalkyl, alkyl, aryl, aralkyl and alkoxycarbonylalkyl, provided that when $M^3$ is $NR^6$ and $M^4$ is absent, then $R^{23}$ is not 1-(1,3-benzodioxol-5-yl)-3-ethoxy-3-oxopropyl, $R^{24}$ when present is selected from the group consisting of alkyl, aryl, aralkyl, heterocyclyl, cycloalkyl, cycloalkylalkyl, and heterocyclylalkyl, and mixtures thereof, $M^6$ is $(CH_2)_q$, where q is an integer from 0 to 6, $R^3$ is selected from the group consisting of hydrogen, $CONR^{13}R^{14}$, $NR^{15}COOR^{16}$, $NR^{15}COR^{16}$, $NR^{15}CONR^{13}R^{14}$, $NR^{15}SO2R^{16}$, $OCOR^{16}$, $COOR^{16}$, $OR^{16}$, $SR^{16}$, heterocyclyl, hydroxyl, hydroxyalkyl, guanadino, alkyl and aryl, $R^{13}$ and $R^{15}$ when present are independently hydrogen or lower alkyl, $R^{14}$ and $R^{16}$ when present are independently selected from the group consisting of hydrogen, alkyl, aryl, aralkyl, cycloalkyl, heterocyclyl, cycloalkylalkyl, and heterocyclylalkyl, $R^1$, $R^2$, $R^3$, $R^{12}$, $R^{14}$, $R^{16}$, $R^{23}$ and $R^{2M}$ when present may independently be either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(aralkyl), —NHCO(haloalkyl), —$NHSO_2$(alkyl), —$NHSO_2$(aryl), —$NHSO_2$(aralkyl), alkoxycarbonyl, alkoxycarbonylalkyl, —OCO(alkylamino), —OCO(dialkylamino), and mixtures thereof;

or a second class of the compounds of Formula (I) defined by:

$R^1$ is aryl or aralkyl, $R^2$ is alkyl or aralkyl, $M^1$ is $CH_2$, $M^2$ is CO, $M^3$ is absent or is O or $CH_2$, $M^4$ is absent or is $CH_2$, $M^5$ is absent or is O or $(CR^{11}R^{12})$, $R^{11}$ is hydrogen, $R^{12}$ is selected from the group consisting of hydrogen, $NR^{21}CONR^{22}R^{23}$, $NR^{21}COR^{24}$, $NR^{21}SO2R^{24}$ and $NR^{21}COOR^{241}$, $R^{21}$ and $R^{22}$ each of which, when present is independently selected from the group of hydrogen and lower alkyl, $R^{23}$ and $R^{24}$, each of which, when present is independently selected from the group consisting of hydrogen, alkyl, aryl, cycloalkyl, cycloalkylalkyl, heterocyclyl, heterocyclylalkyl and aralkyl, $M^6$ is selected from the group consisting of $(CH_2)_q$, $(CH_2)_q$—CH═CH—$(CH_2)_r$, $(CH_2)_q$-arylene-$(CH_2)$, and $(CH_2CH_2O)_q$, where q and r are independently integers from 0 to 6, $R^3$ is $CONR^{13}R^{14}$, $R^{13}$ and $R^{14}$, each of which, when present is independently selected from the group consisting of hydrogen, alkyl, aryl, cycloalkyl, cycloalkylalkyl, heterocyclyl, heterocyclylalkyl and aralkyl, and $R^1$, $R^2$, $R^{13}$, $R^{14}$, $R^{23}$ and $R^{24}$, when present, independently either are unsubstituted or are substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(aralkyl), —NHCO(haloalkyl), —$NHSO_2$(alkyl), —$NHSO_2$(aryl), —$NHSO_2$(aralkyl), alkoxycarbonyl, alkoxycarbonylalkyl, —OCO(alkylamino), —OCO(dialkylamino), and mixtures thereof;

or a third class of the compounds of Formula (I) defined by:

$R^1$ is aryl or aralkyl, $R^2$ is alkyl or aralkyl, $M^1$ is $CH_2$, $M^2$ is $SO_2$ or CO, $M^3$ is absent or is $CH_2$, $M^4$ is absent or is $CH_2$, $M^5$ is absent or is $(CR^{11}R^{12})$, $R^{11}$, when present, is hydrogen, $R^{12}$, when present, is selected from the group consisting of hydrogen, alkyl, $NR^{21}CONR^{22}R^{23}$, $NRCOR^{24}$, $NR^{21}SO2R^{24}$ and $NR^{21}COOR^{24}$, $R^{21}$ and $R^{22}$, each of which when present, is independently selected from the group of hydrogen, lower alkyl, and aralkyl, $R^{23}$ and $R^{24}$, each of which, when present is independently selected from the group consisting of hydrogen, alkyl, aryl, cycloalkyl, cycloalkylalkyl, heterocyclyl, heterocyclylalkyl and aralkyl, $M^6$ is $(CH_2)_q$, or $NR^{34}(CH_2)_q$, q is an integer from 0 to 6, $R^{34}$, when present, is selected form the group consisting of alkyl, aralkyl, $COR^{35}$, and $SO_2R^{35}$, $R^{35}$ when present, is selected form the group consisting of alkyl, aryl, and aralkyl, and $R^3$ is selected from the group consisting of $CONR^{13}R^{14}$, $SO_2NR^{13}R^{14}$, $NR^{15}COOR^{16}$, $NR^{15}COR^{16}$, $NR^{15}CONR^{13}R^{14}$, and $NR^{15}SO_2R^{16}$, $R^{13}$ and $R^{14}$, each of which, when present, is independently selected from the group consisting of hydrogen, alkyl, aryl, cycloalkyl, cycloalkylalkyl, heterocyclyl, heterocyclylalkyl and aralkyl, $R^{15}$ and $R^{16}$, each of which when present, is independently selected from the group of hydrogen, lower alkyl, and aralkyl, $R^1$, $R^2$, $R^{13}$, $R^{14}$, $R^{15}$, $R^{16}$, $R^{23}$, $R^{24}$, $R^{34}$ and $R^{35}$, when present, either are unsubstituted or are substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(aralkyl), —NHCO(haloalkyl), —$NHSO_2$(alkyl), —$NHSO_2$(aryl), —$NHSO_2$(aralkyl), alkoxycarbonyl, alkoxycarbonylalkyl, —OCO(alkylamino), and —OCO(dialkylamino), with the proviso that when $M^2$ is CO, then $M^6$ is $NR^{34}(CH_2)_q$, q is not 0;

or a fourth class of the compounds of Formula (I) defined by:

$R^1$ is alkyl, aryl or aralkyl, $R^2$ is selected from the group consisting of aralkyl and alkyl, provided that when $R^1$ is alkyl, $R^2$ is aralkyl, $M^1$ is CO or $SO_2$, provided that when $M^1$ is $SO_2$ and $R^1$ is phenyl, 4-methylphenyl or 2,4,6-trimethylphenyl, $R^2$ is not alkyl, 2-phenethyl, benzyl, or 2-methoxy-2-oxoethyl, and when $M^1$ is CO and $R^1$ is 2-furyl, 4-pyridyl, or 3,5-dinitrophenyl, $R^2$ is not alkyl, benzyl or 2-(1H-indol-2-yl)ethyl, $M^2$ is absent or $CH_2$, $M^3$ and $M^4$ are absent, $M^5$ is $(CR^{11}R^{12})$, $R^{11}$ is hydrogen, $R^{12}$ is selected from the group consisting of hydrogen, $NR^{21}CONR^{22}R^{23}$, $NR^{21}COR^{24}$, $NR^{21}SO_2R^{24}$, $NR^{21}COOR^{24}$, $CONR^{22}R^{23}$, $COOR^{24}$, $O(CH_2CH_2O)_sR^{24}$, hydroxyalkyl, and alkoxyalkyl, $R^{21}$, and $R^{22}$, when present, are independently selected from the group consisting of hydrogen and $C_1$-$C_6$ alkyl, and $R^{23}$ and $R^{24}$, each of which, when present, is independently selected from the group consisting of hydrogen, alkyl, aryl, cycloalkyl, cycloalkylalkyl, heterocyclyl, heterocyclylalkyl and aralkyl, and s is an integer of 1 to 6, $M^6$ is $(CH_2)_q$, q is an integer of 0 to 6, $R^3$ is selected from the group consisting of $NR^{15}COOR^{16}$, $NR^{15}COR^{16}$, $NR^{15}CONR^{13}R^{14}$, and $NR^{15}SO_2R^{16}$, and $R^{13}$ when present, is independently selected from the group consisting of hydrogen and $C_1$-$C_6$ alkyl, and $R^{14}$, $R^{15}$, and $R^{16}$ each of which, when present, are independently selected from the group consisting of hydrogen, alkyl, aryl, cycloalkyl, cycloalkylalkyl, heterocyclyl, heterocyclylalkyl and aralkyl, and $R^1$, $R^2$, $R^3$, $R^{12}$, $R^{14}$, $R^{15}$, $R^{16}$, $R^{23}$, and $R^{24}$, when present, independently either are unsubstituted or are substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(aralkyl), —NHCO(haloalkyl), —$NHSO_2$(alkyl), —$NHSO_2$(aryl), —$NHSO_2$(aralkyl), alkoxycarbonyl, alkoxycarbonylalkyl, —OCO(alkylamino) and —OCO(dialkylamino);

or pharmaceutically acceptable salts thereof;

or mixtures thereof; and the administering occurs over 30 days, over 18 days, or over 13 days;

the plasma concentration is between about 25 nM and about 100 nM, between about 50 nM and about 100 nM, between about 25 nM and about 75 nM, or between about 50 nM and about 75 nM after each administration; and the administering comprises oral administering or intraperiotoneal administering.

* * * * *